(12) United States Patent
McIvor et al.

(10) Patent No.: US 12,121,567 B2
(45) Date of Patent: Oct. 22, 2024

(54) METHODS TO TREAT MUCOPOLYSACCHARIDOSIS TYPE II OR DEFICIENCY IN IDURONATE-2-SULFATASE USING A RECOMBINANT ADENO-ASSOCIATED VIRUS (AAV) VECTOR ENCODING IDURONATE-2-SULFATASE

(71) Applicants: Regents of the University of Minnesota, Minneapolis, MN (US); REGENXBIO Inc., Rockville, MD (US)

(72) Inventors: R. Scott McIvor, St. Louis Park, MN (US); Lalitha R. Belur, St. Paul, MN (US); Walter Low, Shorewood, MN (US); Carolyn Fairbanks, St. Paul, MN (US); Karen Kozarsky, Bala Cynwyd, PA (US)

(73) Assignees: Regents of the University of Minnesota, Minneapolis, MN (US); REGENXBIO Inc., Rockville, MD (US)

( * ) Notice: Subject to any disclaimer, the term of this patent is extended or adjusted under 35 U.S.C. 154(b) by 0 days.

(21) Appl. No.: 15/717,358

(22) Filed: Sep. 27, 2017

(65) Prior Publication Data
US 2018/0099030 A1 Apr. 12, 2018

Related U.S. Application Data

(62) Division of application No. 14/889,750, filed as application No. PCT/US2014/038209 on May 15, 2014, now Pat. No. 9,827,295.

(60) Provisional application No. 61/823,757, filed on May 15, 2013.

(51) Int. Cl.
| | |
|---|---|
| *C12N 15/11* | (2006.01) |
| *A61K 38/43* | (2006.01) |
| *A61K 38/47* | (2006.01) |
| *A61K 48/00* | (2006.01) |
| *C12N 7/00* | (2006.01) |
| *C12N 15/00* | (2006.01) |
| *C12N 15/113* | (2010.01) |
| *C12N 15/52* | (2006.01) |
| *C12N 15/85* | (2006.01) |
| *C12N 15/86* | (2006.01) |
| *C12N 15/861* | (2006.01) |

(52) U.S. Cl.
CPC .............. *A61K 38/47* (2013.01); *C12N 7/00* (2013.01); *C12N 15/86* (2013.01); *A61K 48/00* (2013.01); *C12N 2750/14143* (2013.01); *C12N 2750/14171* (2013.01); *C12N 2830/007* (2013.01); *C12Y 302/01076* (2013.01)

(58) Field of Classification Search
CPC .... A61K 9/0085; A61K 9/0019; A61K 35/76; A61K 35/761; A61K 48/00; C12Y 301/06013; C12Y 302/0105; C12Y 302/01045; C12Y 302/01076; C12Y 310/01001; C12N 15/86
See application file for complete search history.

(56) References Cited

U.S. PATENT DOCUMENTS

| | | | |
|---|---|---|---|
| 5,624,898 | A | 4/1997 | Frey, II |
| 6,180,603 | B1 | 1/2001 | Frey, II |
| 6,190,659 | B1 | 2/2001 | Pancholi et al. |
| 6,309,634 | B1 | 10/2001 | Bankiewicz et al. |
| 6,313,093 | B1 | 11/2001 | Frey, II |
| 6,342,478 | B1 | 1/2002 | Frey, II |
| 6,407,061 | B1 | 6/2002 | Frey, II |
| 6,569,661 | B1 | 5/2003 | Qin et al. |
| 6,858,206 | B2 | 2/2005 | Kakkis |
| 6,953,575 | B2 | 10/2005 | Bankiewicz et al. |
| 6,991,785 | B2 | 1/2006 | Frey, II |
| 7,084,126 | B1 | 8/2006 | Frey, II et al. |
| 7,442,372 | B2 | 10/2008 | Kakkis |
| 7,446,098 | B2 | 11/2008 | Fan |
| 7,569,544 | B2 | 8/2009 | Zankel et al. |
| 7,592,321 | B2 | 9/2009 | Whitley et al. |
| 7,989,502 | B2 | 8/2011 | Greco et al. |
| 8,153,604 | B2 | 4/2012 | Deen et al. |
| 8,252,745 | B2 | 8/2012 | Yeomans et al. |
| 8,283,160 | B2 | 10/2012 | Frey, II et al. |
| 8,501,691 | B2 | 8/2013 | Yeomans et al. |

(Continued)

FOREIGN PATENT DOCUMENTS

| | | |
|---|---|---|
| BR | 112017024519 | 7/2018 |
| CA | 2500523 A1 | 11/2004 |

(Continued)

OTHER PUBLICATIONS

U.S. Appl. No. 16/461,271, filed May 2019, Podetz-Pedersen et al.*

(Continued)

*Primary Examiner* — Chang-Yu Wang

(74) *Attorney, Agent, or Firm* — Schwegman Lundberg & Woessner, P.A.

(57) ABSTRACT

A method to prevent, inhibit or treat one or more symptoms associated with a disease of the central nervous system by intrathecally, intracerebroventricularly or endovascularly administering a rAAV encoding a gene product associated with the disease, e.g., a mammal in which the gene product is absent or present at a reduced level relative to a mammal without the disease.

25 Claims, 23 Drawing Sheets

(56) References Cited

U.S. PATENT DOCUMENTS

| | | | |
|---|---|---|---|
| 8,545,837 B2 * | 10/2013 | Zhu | A61K 9/0085 424/94.3 |
| 8,609,088 B2 | 12/2013 | Wolf et al. | |
| 8,622,993 B2 | 1/2014 | Frey, II et al. | |
| 8,632,764 B2 | 1/2014 | Xiao et al. | |
| 8,715,661 B2 | 5/2014 | Pardridge et al. | |
| 8,796,236 B2 | 8/2014 | Dodge et al. | |
| 8,889,641 B2 | 11/2014 | Asokan et al. | |
| 8,920,801 B2 | 12/2014 | Pardridge et al. | |
| 8,999,948 B2 | 4/2015 | Tubert et al. | |
| 9,089,566 B2 * | 7/2015 | Kakkis | A61K 38/47 |
| 9,102,949 B2 | 8/2015 | Gao | |
| 9,133,482 B2 | 9/2015 | Harper et al. | |
| 9,186,419 B2 | 11/2015 | Xiao et al. | |
| 9,186,420 B2 | 11/2015 | Koeberl | |
| 9,220,677 B2 * | 12/2015 | Zhu | A61K 9/0085 |
| 9,249,424 B2 | 2/2016 | Wolf et al. | |
| 9,265,843 B2 | 2/2016 | During et al. | |
| 9,279,132 B2 | 3/2016 | Bosch et al. | |
| 9,283,181 B2 * | 3/2016 | Calias | A61K 9/0085 |
| 9,284,357 B2 | 3/2016 | Gao et al. | |
| 9,320,711 B2 * | 4/2016 | Natoli | A61K 9/0085 |
| 9,402,921 B2 | 8/2016 | Xiao et al. | |
| 9,409,953 B2 | 8/2016 | Asokan et al. | |
| 9,415,121 B2 | 8/2016 | Kaspar et al. | |
| 9,469,851 B2 | 10/2016 | Harper et al. | |
| 9,572,870 B2 * | 2/2017 | Kakkis | A61K 38/47 |
| 9,670,507 B2 | 6/2017 | Xiao et al. | |
| 9,770,410 B2 * | 9/2017 | Salamat-Miller | A61K 9/0085 |
| 9,814,764 B2 * | 11/2017 | Concino | A61K 9/0085 |
| 9,821,114 B2 | 11/2017 | Cabrera Aquino et al. | |
| 9,827,295 B2 * | 11/2017 | McIvor | C12N 15/86 |
| 10,035,825 B2 | 7/2018 | Gao et al. | |
| 10,370,432 B2 | 8/2019 | Esteves et al. | |
| 10,912,804 B2 | 2/2021 | Byrne et al. | |
| 2001/0043915 A1 | 11/2001 | Frey, II | |
| 2002/0014242 A1 | 2/2002 | Scaria | |
| 2002/0072498 A1 | 6/2002 | Frey, II | |
| 2002/0082215 A1 | 6/2002 | Frey | |
| 2002/0110551 A1 | 8/2002 | Chen | |
| 2002/0169102 A1 | 11/2002 | Frey, II | |
| 2003/0072793 A1 | 4/2003 | Frey, II et al. | |
| 2003/0165434 A1 | 9/2003 | Reinhard et al. | |
| 2003/0215398 A1 | 11/2003 | Frey, II | |
| 2003/0219414 A1 | 11/2003 | Podsakoff et al. | |
| 2004/0009906 A1 | 1/2004 | Kakkis et al. | |
| 2004/0204379 A1 * | 10/2004 | Cheng | A61K 31/445 514/44 R |
| 2005/0026823 A1 | 2/2005 | Zankel et al. | |
| 2005/0032841 A1 | 2/2005 | Walkley | |
| 2005/0042227 A1 | 2/2005 | Zankel et al. | |
| 2005/0048047 A1 | 3/2005 | Kakkis | |
| 2005/0256059 A1 | 11/2005 | Benowitz | |
| 2006/0057114 A1 | 3/2006 | Whitley et al. | |
| 2006/0188496 A1 | 8/2006 | Bentz et al. | |
| 2006/0216317 A1 | 9/2006 | Reinhard et al. | |
| 2007/0092500 A1 | 4/2007 | Frey, II et al. | |
| 2008/0305077 A1 | 12/2008 | Frey, II et al. | |
| 2009/0068155 A1 | 3/2009 | Frey, II et al. | |
| 2009/0117156 A1 * | 5/2009 | Passini | A61K 48/0083 424/233.1 |
| 2009/0123451 A1 | 5/2009 | Dodge et al. | |
| 2009/0136505 A1 | 5/2009 | Bentz et al. | |
| 2009/0264506 A1 | 10/2009 | Reinhard et al. | |
| 2010/0061959 A1 | 3/2010 | Frey, II et al. | |
| 2010/0068183 A1 | 3/2010 | Whitley et al. | |
| 2010/0173979 A1 * | 7/2010 | Dodge | C12N 15/86 514/44 R |
| 2010/0199366 A1 | 8/2010 | Cooper et al. | |
| 2010/0221225 A1 | 9/2010 | Byrne et al. | |
| 2010/0221235 A1 | 9/2010 | Arranz | |
| 2011/0070220 A1 | 3/2011 | Koeberl | |
| 2011/0070241 A1 | 3/2011 | Yang | |
| 2011/0104120 A1 | 5/2011 | Xiao et al. | |
| 2011/0182875 A1 | 7/2011 | Fang et al. | |
| 2011/0288160 A1 | 11/2011 | During et al. | |
| 2012/0009268 A1 | 1/2012 | Asokan et al. | |
| 2012/0177605 A1 | 7/2012 | Kaspar et al. | |
| 2012/0288489 A1 | 11/2012 | Wolf et al. | |
| 2012/0315263 A1 | 12/2012 | Olmstead | |
| 2012/0322861 A1 | 12/2012 | Byrne et al. | |
| 2013/0039888 A1 | 2/2013 | Mccarty et al. | |
| 2013/0095092 A1 | 4/2013 | Quinn et al. | |
| 2013/0096488 A1 | 4/2013 | Frey, II | |
| 2013/0122591 A1 | 5/2013 | Cost et al. | |
| 2013/0195801 A1 * | 8/2013 | Gao | C12N 15/86 424/93.2 |
| 2013/0211380 A1 | 8/2013 | Cabrera et al. | |
| 2013/0225666 A1 | 8/2013 | Kaspar et al. | |
| 2013/0323207 A1 | 12/2013 | Mccarty et al. | |
| 2014/0045925 A1 | 2/2014 | Harper et al. | |
| 2014/0056854 A1 | 2/2014 | Asokan et al. | |
| 2014/0088179 A1 | 3/2014 | Davidson | |
| 2014/0161788 A1 | 6/2014 | Aoyagi-scharber et al. | |
| 2014/0171491 A1 | 6/2014 | Wolf | |
| 2014/0219974 A1 | 8/2014 | Pan | |
| 2014/0234274 A1 | 8/2014 | Xiao et al. | |
| 2014/0322169 A1 | 10/2014 | Harper et al. | |
| 2014/0335054 A1 | 11/2014 | Gao | |
| 2015/0066056 A1 | 3/2015 | Cabrera Aquino et al. | |
| 2015/0118201 A1 | 4/2015 | Xiao et al. | |
| 2015/0150799 A1 | 6/2015 | Kakkis | |
| 2015/0182637 A1 | 7/2015 | Barkats et al. | |
| 2015/0196671 A1 | 7/2015 | Byrne et al. | |
| 2015/0210771 A1 | 7/2015 | Crystal et al. | |
| 2015/0252384 A1 | 9/2015 | Kaspar et al. | |
| 2016/0038613 A1 | 2/2016 | Kaspar et al. | |
| 2016/0076028 A1 | 3/2016 | Flanigan et al. | |
| 2016/0120960 A1 | 5/2016 | Mcivor et al. | |
| 2016/0166709 A1 | 6/2016 | Davidson et al. | |
| 2016/0175406 A1 | 6/2016 | Mccarty et al. | |
| 2016/0208006 A1 | 7/2016 | Pardridge et al. | |
| 2016/0243260 A1 * | 8/2016 | Blits | C12N 15/86 |
| 2016/0272976 A1 | 9/2016 | Kaspar et al. | |
| 2016/0304904 A1 | 10/2016 | Xiao et al. | |
| 2016/0310548 A1 | 10/2016 | Harper et al. | |
| 2016/0369297 A1 | 12/2016 | Byrne et al. | |
| 2017/0028002 A1 | 2/2017 | Byrne et al. | |
| 2017/0029849 A1 | 2/2017 | Harper et al. | |
| 2017/0049887 A1 | 2/2017 | Byrne et al. | |
| 2018/0036388 A1 | 2/2018 | Mcivor et al. | |
| 2018/0051299 A9 | 2/2018 | Byrne et al. | |
| 2018/0071373 A1 * | 3/2018 | McIvor | A61K 38/47 |
| 2018/0245054 A1 | 8/2018 | Kawaoka et al. | |
| 2018/0264090 A1 | 9/2018 | Mcivor et al. | |
| 2018/0271955 A1 | 9/2018 | Mcivor et al. | |
| 2018/0271956 A1 | 9/2018 | Mcivor et al. | |
| 2018/0271957 A1 | 9/2018 | Mcivor et al. | |
| 2018/0289839 A1 | 10/2018 | Mcivor et al. | |
| 2019/0269799 A1 | 9/2019 | Laoharawee et al. | |
| 2019/0298812 A1 | 10/2019 | Mcivor et al. | |
| 2021/0085759 A1 | 3/2021 | Mcivor et al. | |
| 2021/0085760 A1 | 3/2021 | Mcivor et al. | |
| 2021/0346473 A1 * | 11/2021 | McIvor | A61P 25/00 |
| 2021/0369871 A1 | 12/2021 | Mcivor et al. | |
| 2022/0096659 A1 * | 3/2022 | Laoharawee | A61K 9/0085 |
| 2022/0125843 A1 | 4/2022 | Moriarity et al. | |
| 2022/0211875 A1 * | 7/2022 | McIvor | C12N 7/00 |

FOREIGN PATENT DOCUMENTS

| | | |
|---|---|---|
| CA | 2880653 A1 | 2/2014 |
| CN | 103037895 | 4/2013 |
| CN | 103037905 A | 4/2013 |
| CN | 105377039 | 3/2016 |
| CN | 106661591 | 5/2017 |
| CN | 108367055 A | 8/2018 |
| CN | 110913872 | 3/2020 |
| CN | 115120745 | 9/2022 |
| CN | 115120746 | 9/2022 |
| CN | 109863243 | 7/2023 |
| CN | 117440820 | 1/2024 |
| EP | 1658857 | 5/2006 |
| EP | 1915986 A1 | 4/2008 |

(56) References Cited

FOREIGN PATENT DOCUMENTS

| | | |
|---|---|---|
| EP | 3294323 B1 | 10/2021 |
| HK | 1252871 | 11/2022 |
| IN | 2017/17045072 A | 3/2018 |
| JP | S59-29648 A | 2/1984 |
| JP | 2006-503847 A | 2/2006 |
| JP | 2006-517980 A | 8/2006 |
| JP | 2018/515615 A | 6/2018 |
| JP | 2020-073559 A | 5/2020 |
| JP | 2021-167332 A | 10/2021 |
| JP | 2022-065134 A | 4/2022 |
| JP | 2022137261 | 9/2022 |
| JP | 2023022250 | 2/2023 |
| KR | 20160010526 | 1/2016 |
| KR | 102406615 | 6/2022 |
| MX | 397045 | 11/2022 |
| RU | 2452368 C2 | 6/2012 |
| RU | 2692251 C2 | 6/2019 |
| SG | 10201710448 A | 1/2018 |
| SG | 10202260321 T | 3/2023 |
| WO | WO-9107947 A1 | 6/1991 |
| WO | WO-9906562 A1 | 2/1999 |
| WO | WO-0033813 A1 | 6/2000 |
| WO | WO-0033814 A2 | 6/2000 |
| WO | WO-0141782 A2 | 6/2001 |
| WO | WO-0232449 A2 | 4/2002 |
| WO | WO-02086105 A1 | 10/2002 |
| WO | WO-03072056 A2 | 9/2003 |
| WO | WO-2008049588 A1 | 5/2008 |
| WO | WO-2008/103993 A2 | 8/2008 |
| WO | WO-2009/043936 A1 | 4/2009 |
| WO | WO-2009/097129 A1 | 8/2009 |
| WO | WO-2011133890 A1 | 10/2011 |
| WO | WO-2011/154520 A1 | 12/2011 |
| WO | WO-2011163649 A2 | 12/2011 |
| WO | WO-2014022582 A1 | 2/2014 |
| WO | WO-2014178863 A1 | 11/2014 |
| WO | WO-2014186579 A1 | 11/2014 |
| WO | WO-2015013148 A2 | 1/2015 |
| WO | WO-2016100575 A1 | 6/2016 |
| WO | WO-2016187017 A1 | 11/2016 |
| WO | WO-2017/136500 A1 | 8/2017 |
| WO | WO-2017136202 A1 | 8/2017 |
| WO | WO-2018/093925 A1 | 5/2018 |
| WO | WO-2018/209205 A1 | 11/2018 |
| WO | WO-2019/010335 A1 | 1/2019 |
| WO | 2022170082 | 8/2022 |

OTHER PUBLICATIONS

Clearley and Wolfe, Mol. Thera. 2006; 13:528-537.*
Cardone et al. Hum. Mol. Genet. 2006; 15:1125-1236. doi: 10.1093/hmg/ddl038.*
Calias et al. PLoS One, 2012; 7:e30341. doi: 10.1371/journal.pone.0030341.*
Dayton et al. Expert opin. Biol. Ther. 2012; 12:757-766. doi: 10.1571/14712598.2012.681463.*
"U.S. Appl. No. 15/574,432, Supplemental Preliminary Amendment Filed Nov. 15, 2017", 6 pgs.
"U.S. Appl. No. 15/574,432, Preliminary Amendmetn filed Nov. 15, 2017", 6 pgs.
"U.S. Appl. No. 15/717,450, Preliminary Amendment filed Oct. 3, 2017", 6 pgs.
"U.S. Appl. No. 15/717,450, Restriction Requirement mailed Feb. 22, 2018", 12 pgs.
"U.S. Appl. No. 15/717,450, Supplemental Preliminary Amendment filed Oct. 16, 2017", 3 pgs.
"U.S. Appl. No. 15/813,908, Restriction Requirement mailed Feb. 9, 2018", 6 pgs.
"U.S. Appl. No. 15/717,450, Second Supplemental Preliminary Amendment filed Nov. 27, 2017", 6 pgs.
"Australian Application Serial No. 2014265417, Response filed Jan. 4, 2018 to First Examination Report mailed Jul. 9, 2017", 21 pgs.
"Australian Application Serial No. 2014265417, Subsequent Examiners Report mailed Feb. 3, 2018", 5 pgs.
"Chinese Application Serial No. 201480027622.1, Response filed Dec. 12, 2017 to Office Action mailed Jul. 28, 2017", (w/ English Translation of Amended Claims), 16 pgs.
"European Application Serial No. 14798331.6, Office Action mailed Jan. 9, 2017", 1 pg.
"European Application Serial No. 14798331.6, Response filed Jul. 29, 2016 to Office Action mailed Jan. 19, 2016", 4 pgs.
"International Application Serial No. PCT/US2016/032392, International Preliminary Report on Patentability mailed Nov. 30, 2017", 7 pgs.
"International Application Serial No. PCT/US2017/061838, International Search Report mailed Mar. 5, 2018", 7 pgs.
"International Application Serial No. PCT/US2017/061838, Written Opinion mailed Mar. 5, 2018", 11 pgs.
"Japanese Application Serial No. 2016-514092, Office Action mailed Feb. 14, 2018", (w/ English Translation), 7 pgs.
Byrne, Barry J., et al., "Gene Therapy Approaches for Lysosomal Storage Disease: Next-Generation Treatment", Human Gene Therapy, 23(8), (2012), 808-815.
Christian, Hinderer, et al., "Delivery of an Adeno-Associated Virus Vector into Cerebrospinal Fluid Attenuates Central Nervous System Disease in Mucopolysaccharidosis Type II Mice", Human Gene Therapy, vol. 27 No. 11, (Nov. 1, 2016), 906-915.
Fraldi, A, et al., "SUMF1 enhances sulfatase activities in vivo in five sulfatase deficiencies", Biochemical Journal Portland Press Ltd GB vol. 403 No. 2, (Apr. 15, 2007), 305-312.
Gilkes, J A, et al., "Preferred transduction with AAV8 and AAV9 via thalamic administration in the Mps IIIb model: A comparison of four rAAV Serotype", Molecular Genetics and Metabolism Reports, vol. 6, (Mar. 1, 2016), 48-54.
Kanut, Laoharawee, et al., "Prevention of Neurocognitive Deficiency in Mucopolysaccharidosis Type II Mice by Central Nervous System-Directed, AAV9-Mediated Iduronate Sulfatase Gene Transfer", Human Gene Therapy vol. 28 No. 8, (Aug. 1, 2017), 626-638.
Meyer, Kathrin, et al., "Improving Single Injection CSF Delivery of AAV9-mediated Gene Therapy for SMA: A Dose-response Study in Mice and Nonhuman Primates", Molecular Therapy, 23(3), (Mar. 2015), 477-487.
Nash, L .. A., et al., "Spinal Muscular Atrophy: More than a Disease of Motor Neurons?", Current Molecular Medicine, 16, (2016), 779-792.
Sandra, Motas, et al., "CNS-directed gene therapy for the treatment of neurologic and somatic mucopolysaccharidosis type TI Hunter syndrom", JCI Insight vol. 1 No. 9, (Jun. 16, 2016).
Schuster, Daniel J., et al., "Visualization of spinal afferent innervation in the mouse colon by AAV8-mediated GFP expression", NIH Public Access, published in final format as: Neurogastroenterol Motil., 25(2): e89-e100 (2013), (2013), 19 pgs.
"U.S. Appl. No. 15/717,450, Response filed Apr. 23, 2018 to Restriction Requirement mailed Feb. 22, 2018", 7 pgs.
"U.S. Appl. No. 15/813,908, Response Filed Apr. 23, 2018 to Restriction Requirement mailed Feb. 9, 2018", 6 pgs.
"Australian Application Serial No. 2014265417, Response filed Apr. 26, 2018 to Subsequent Examiners Report mailed Feb. 3, 2018", 15 pgs.
"Australian Application Serial No. 2014265417, Response filed Jun. 29, 2018 to Subsequent Examiners Report mailed Jun. 6, 2018", 5 pgs.
"Australian Application Serial No. 2014265417, Subsequent Examiners Report mailed Jun. 6, 2018", 4 pgs.
"Chinese Application Serial No. 201480027622.1, Office Action mailed Apr. 8, 2018", (w/ English Translation), 25 pgs.
"European Application Serial No. 14798331.6, Communication Pursuant to Article 94(3) EPC mailed Apr. 20, 2018", 8 pgs.
"European Application Serial No. 16797013.6 Response filed Jul. 2, 2018 to Communication Pursuant toRules 161(2) EPC mailed Dec. 22, 2017", 9 pgs.
"Mexican Application Serial No. MX/a/2015/015560, Office Action mailed Jul. 2, 2018", (English Translation), 2 pgs.

(56) References Cited

OTHER PUBLICATIONS

"Russian Application Serial No. 2015152546, Office Action and Search Report mailed Apr. 11, 2018", (w/ English Translation), 13 pgs.

Bevan, Adam K, "Systemic Gene Delivery in Large Species for Targeting Spinal Cord, Brain, and Peripheral Tissues for Pediatric Disorders", *Molecular Therapy*, 19(11), (2011), 1971-1980.

Federici, T., et al., "Robust spinal motor neuron transduction following intrathecal delivery of AAV9 in pigs", *Gene Therapy*, 19(8), (Sep. 15, 2011), 852-859.

Jameson, E., et al., "Enzyme replacement therapy with laronidase (Aldurazyme®) for treating mucopolysaccharidosis type I (Review)", *Cochrane Database of Systematic Reviews 2013*, Issue 9. (2013), 1-19.

Mei, Xingguo, In: *Microcarrier Drug Delivery System*, Huazhong University of Science and Technology Press, (Nov. 30, 2009), p. 335 (a total of four pages).

Spampanato, Carmine, et al., "Efficacy of a Combined Intracerebral and Systemic Gene Delivery Approach for the Treatment of a Severe Lysosomal Storage Disorder", *Molecular Therapy*, 19(5), (2011), 860-869.

Su, Dingfeng, In: *Cardiovascular Pharmacology*, Science Press (w/ Examiner's Explanation), (Oct. 31, 2001), p. 415 (a total of four pages).

Wang, Binghe, et al., In: *Drug Delivery: Principles and Applications*, Chemical Industry Press, (w/ Examiner's Explanation), (Jan. 31, 2008), pp. 22-23 (a total of five pages).

U.S. Appl. No. 13/465,575 U.S. Pat. No. 8,609,088, filed May 7, 2012, Intranasal Delivery of Therapeutic Enzymes to The Central Nervous System for The Treatment of Lysosomal Storage Diseases.

U.S. Appl. No. 14/103,597 U.S. Pat. No. 9,249,424, filed Dec. 11, 2013, Intranasal Delivery of AAV Encoding Therapeutic Enzymes to The Central Nervous System for The Treatment of Lysosomal Storage Diseases.

U.S. Appl. No. 14/889,750, filed Nov. 6, 2015, Methods to Treat Mucopolysaccharide Type I or Deficiency in Alpha-L-Iduronidase Using a Recombinant Adeno-Associated Virus Encoding Alpha-L-Iduronidase.

U.S. Appl. No. 14/889,750, filed Nov. 6, 2015, Methods to Treat Mucopolusaccharide Type I of Deficiency in Alpha-L-Iduronidase Using a Recombinant Adeno-Associated Virus Encoding Alpha-L-Iduronidase.

U.S. Appl. No. 15/717,450, filed Sep. 27, 2017, Adeno-Associated Virus Mediated Gene Transfer to The Central Nervous System.

U.S. Appl. No. 15/987,490, filed May 23, 2018, Adeno-Associated Virus Mediated Gene Transfer to The Central Nervous System.

U.S. Appl. No. 15/989,405, filed May 25, 2018, Adeno-Associated Virus Mediated Gene Transfer to The Central Nervous System.

U.S. Appl. No. 15/995,045, filed May 31, 2018, Methods to Treat Pompe Disease Using a Recombinant Adeno-Associated Virus.

U.S. Appl. No. 15/813,908, filed Nov. 15, 2017, Adeno-Associated Virus for Therapeutic Delivery to Central Nervous System.

U.S. Appl. No. 15/574,432 filed Nov. 15, 2017, Intranasal Therapeutic Delivery of Adeno-Associated Virus to Central Nervous System.

"U.S. Appl. No. 12/463,575, Response filed Dec. 10, 2012 to Restriction Requirement mailed Nov. 9, 2012", 6 pgs.

"U.S. Appl. No. 13/465,575 , Response filed May 9, 2013 to Non Final Office Action mailed Feb. 11, 2013", 9 pgs.

"U.S. Appl. No. 13/465,575, Non Final Office Action mailed Feb. 11, 2013", 15 pgs.

"U.S. Appl. No. 13/465,575, Notice of Allowance mailed Aug. 8, 2013", 11 pgs.

"U.S. Appl. No. 13/465,575, Restriction Requirement mailed Nov. 9, 2012", 8 pgs.

"U.S. Appl. No. 14/103,597, Examiner Interview Summary mailed Dec. 4, 2015", 2 pgs.

"U.S. Appl. No. 14/103,597, Final Office Action mailed Jun. 25, 2015", 11 pgs.

"U.S. Appl. No. 14/103,597, Non Final Office Action mailed Jan. 5, 2015", 12 pgs.

"U.S. Appl. No. 14/103,597, Notice of Allowance mailed Sep. 11, 2015", 9 pgs.

"U.S. Appl. No. 14/103,597, Notice of Allowance mailed Oct. 7, 2015", 5 pgs.

"U.S. Appl. No. 14/103,597, Preliminary Amendment filed Dec. 12, 2013", 6 pgs.

"U.S. Appl. No. 14/103,597, Response filed Apr. 6, 2015 to Non Final Office Action mailed Jan. 5, 2015", 13 pgs.

"U.S. Appl. No. 14/103,597, Response filed Aug. 25, 2015 to Final Office Action mailed Jun. 25, 2015", 7 pgs.

"U.S. Appl. No. 14/103,597, Response filed Nov. 25, 2014 to Restriction Requirement mailed Sep. 25, 2014", 6 pgs.

"U.S. Appl. No. 14/103,597, Restriction Requirement mailed Sep. 25, 2014", 8 pgs.

"U.S. Appl. No. 14/889,750, Final Office Action mailed May 18, 2017", 24 pgs.

"U.S. Appl. No. 14/889,750, Non Final Office Action mailed Oct. 6, 2016", 26 pgs.

"U.S. Appl. No. 14/889,750, Notice of Allowance mailed Jul. 27, 2017", 14 pgs.

"U.S. Appl. No. 14/889,750, Preliminary Amendment filed Nov. 6, 2015", 7 pgs.

"U.S. Appl. No. 14/889,750, Response filed Feb. 6, 2017 to Non Final Office Action mailed Oct. 6, 2016", 10 pgs.

"U.S. Appl. No. 14/889,750, Response filed Jun. 27, 2017 to Final Office Action mailed May 18, 2017", 9 pgs.

"U.S. Appl. No. 14/889,750, Response filed Jul. 5, 2016 to Restriction Requirement mailed May 5, 2016", 7 pgs.

"U.S. Appl. No. 14/889,750, Restriction Requirement mailed May 5, 2016", 6 pgs.

"ASGCT—American Society of Gene & Cell Therapy. 16th Annual Meeting 2013, Abstracts", Retrieved from the Internet: <URL:http://www.asgct.orgjmeetings-educational-programsjasgct-annual-meetingsjarchived-annual-meetings/2013-annual-meetingjat-tendeejabstracts> [retrieved on Dec. 2, 2016], (Apr. 19, 2013).

"Australian Application Serial No. 2014265417, First Examination Report mailed Jul. 9, 2017", 6 pgs.

"Chinese Application Serial No. 201480027622.1, Office Action mailed Jul. 28, 2017", (w/ English Translation), 19 pgs.

"European Application Serial No. 14798331.6, Extended European Search Report mailed Dec. 13, 2016", 12 pgs.

"European Application Serial No. 14798331.6, Office Action mailed Jan. 19, 2016", 2 pgs.

"European Application Serial No. 14798331.6, Response filed Jul. 19, 2017 to Extended European Search Report mailed Dec. 13, 2016", 10 pgs.

"International Application Serial No. PCT/US2014/038209, International Preliminary Report on Patentability mailed Nov. 26, 2015", 7 pgs.

"International Application Serial No. PCT/US2014/038209, International Search Report mailed Sep. 26, 2014", 3 pgs.

"International Application Serial No. PCT/US2014/038209, Written Opinion mailed Sep. 26, 2014", 10 pgs.

"International Application Serial No. PCT/US2016/032392, International Search Report mailed Aug. 19, 2016", 3 pgs.

"International Application Serial No. PCT/US2016/032392, Written Opinion mailed Aug. 19, 2016", 5 pgs.

"Russian Application Serial No. 2015152546, Office Action mailed Feb. 11, 2016", (w/ English Translation), 3 pgs.

"Russian Application Serial No. 2015152546, Response filed May 11, 2016 to Office Action mailed Feb. 11, 2016", (w/ English Translation of Claims), 31 pgs.

Barone, R., et al., "Extraneurologic Symptoms as Presenting Signs of Sanfilippo Disease", Pediatr Neurol., 25(3), (Sep. 2001), 254-7.

Belur, Let, et al., "AAV Vector-Mediated Iduronidase Gene Delivery in a Murine Model of Mucopolysaccharidosis Type I: Comparing Different Routes of Delivery to the CNS", Abstracts for the ASGCT16th Annual Meeting. May 15-18, 2013. Salt Lake City. Utah, US, Retrieved from the Internet: <URL:http://www.nature.comjmtjournaljv21/n1s/pdf/mt201382a.pdf> [retrieved on Dec. 2, 2016], (Apr. 19, 2013).

(56) References Cited

OTHER PUBLICATIONS

Cherin, P., et al., "[Neurological manifestations of type 1 Gaucher's disease: Is a revision of disease classification needed?]", Rev Neurol (Paris), 162(11), [Article in French, w/ English Summary], (Nov. 2006), 1076-83.

Ciron, C, et al., "Human [alpha]-Iduronidase Gene Transfer Mediated by Adena-Associated Virus Types 1. 2. and 5 in the Brain of Nonhuman Primates: Vector Diffusion and Biodistribution", Human Gene Therapy, vol. 20. No. 4, (Apr. 1, 2009), 350-360.

Dhuria, S. V, et al., "Intranasal delivery to the central nervous system: mechanisms and experimental considerations", J Pharm Sci., 99(4), (Apr. 2010), 1654-73.

Donovan, M. D., et al., "Large molecule and particulate uptake in the nasal cavity: the effect of size on nasal absorption", Advanced Drug Delivery Reviews, vol. 29, (1998), 147-155.

Draghia, R., et al., "Gene delivery into the central nervous system by nasal instillation in rats", Gene Therapy, 2(6), (1995), 418-423.

Fu, et al., "Neurological correction of lysosomal storage in a mucopolysaccharidosis IIIB mouse model by adeno-associated virus-mediated gene delivery", Molecular Therapy, vol. 5, No. 1, (Jan. 1, 2002), 42-49 pgs.

Guo, Yansu, "A single injection of recombinant adeno-associated virus into the lumbar cistern delivers transgene expression throughout the whole spinal cord", HHS Public Access, Author manuscript, Mol Neurobiol., 53(5), (Jul. 2016), 3235-3248.

Han, I. K., et al., "Enhanced brain targeting efficiency of intranasally administered plasmid DNA: an alternative route for brain gene therapy", J. Mol. Med. (Berl), 85(1), (2006), 75-83.

Hartung, S. D, et al., "Correction of Metabolic, Craniofacial, and Neurologic Abnormalities in MPS I Mice Treated at Birth with Adeno-associated Virus Vector Transducing the Human A-L-Iduronidase Gene", Molecular Therapy, 9(6), (2004), 866-875.

Hoffmann, B., et al., "Neurological manifestations in lysosomal storage disorders—from pathology to first therapeutic possibilities", Neuropediatrics, 36(5), (Oct. 2005), 285-9.

Iwamoto, N, et al., "Global diffuse distribution in the brain and efficient gene delivery to the dorsal root ganglia by intrathecal injection of adena-associated viral vector serotype 1", Journal of Gene Medicine. John Wiley & Sons, Inc, US, vol. 11, No. 6, (Jun. 1, 2009), 498-505.

Janson, C, et al., "Comparison of intraventricular vs. endovascular AAV5 mediated IDUA gene delivery to the brain in the MPS-I mouse model", Molecular Genetics and Metabolism, vol. 102. No. 2, Amsterdam. N L, (Feb. 1, 2011), S22.

Janson, Christopher G., et al., "Comparison of Endovascular and Intraventricular Gene Therapy With Adeno-Associated Virus-alpha-L-Iduronidase for Hurler Disease", Neurosurgery, 74(1), (2014), 99-111.

Jerusalmi, A., et al., "Effect of Intranasal Administration of Semliki Forest Virus Recombinant Particles Expressing Reporter and Cytokine Genes on the Progression of Experimental Autoimmune Encephalomyelitis", Mol Therapy, 8(6), (2003), 886-894.

Kaback, M. M, et al., "Hexosaminidase A Deficiency", In: Pagon RA, Bird TD, Dolan CR, et al., editors. GeneReviews™ [Internet]. Seattle (WA): University of Washington, Seattle; 1993-. Available from: http://www.ncbi.nlm.nih.gov/books/NBK1218/, (Mar. 11, 1999 [Updated Aug. 11, 2011]), 13 pgs.

Kaemmerer, William F., et al., "In Vivo Transduction of Cerebellar Purkinje Cells Using Adeno-Associated Virus Vectors", Molecular Therapy, 2(5), (2000), 446-457.

Kakkis, E., et al., "Intrathecal enzyme replacement therapy reduces lysosomal storage in the brain and meninges of the canine model of MPS I", Molecular Genetics and Metabolism , vol. 83, (2004), 163-174.

Laing, J., "Intranasal administration of the growth compromised HSV-2 vector ?RR prevents kainate induced seizures and neuronal loss in rats and mice", Mol Therapy, 13(5), (2006), 870-881.

Lemiale, F., et al., "Enhanced Mucosal Immunoglobulin A Response of Intranasal Adenoviral Vector Human Immunodeficiency Virus Vaccine and Localization in the Central Nervous System", J. Vitol., 77(18), (2003), 10078-10087.

Martin, R., et al., "Recognition and diagnosis of mucopolysaccharidosis II (Hunter syndrome).", Pediatrics, 121(2), (Feb. 2008), e377-e386.

Martino, S., et al., "Absence of Metabolic Cross-correction in Tay-Sachs Cells", The Journal of Biological Chemistry, 277(23), (2002), 20177-20184.

McCarty, D M, et al., "Mannitol-facilitated CNS entry of rAAV2 vector significantly delayed the neurological disease progression in MPS IIIB mice", Gene Therapy, vol. 16, No. 11, (Jul. 9, 2009), 1340-1352.

Samaranch, et al., "", Gene Ther. 23, (2012), 382-389.

Samaranch, Lluis, et al., "Strong Cortical and Spinal Cord Transduction After AAV7 and AAV9 Delivery into the Cerebrospinal Fluid of Nonhuman Pirimates", Human Gene Therapy, 24, (May 2013), 526-532.

Talegaonkar, S., et al., "Intranasal delivery: An approach to bypass the blood brain barrier", Indian Journal of Pharmacology, vol. 36, (2004), 140-147.

Vulchanova, L, et al., "Differential adeno-associated virus mediated gene transfer to sensory neurons following intrathecal delivery by direct lumbar puncture", Molecular Pain, vol. 6. No. 1, (Jan. 1, 2010), 31.

Wang, Hongyan, et al., "Widespread spinal cord transduction by intrathecal injection of rAAV delivers efficacious RNAi therapy for amyotrophic lateral sclerosis", Human Molecular Genetics, vol. 23, No. 3, (2014), 668-681.

Watson, G., et al., "Intrathecal administration of AAV vectors for the treatment of lysosomal storage in the brains of MPS I mice", Gene Therapy, 13, (2006), 1-9.

Wolf, D. A., et al., "Lysosomal enzyme can bypass the blood-brain barrier and reach the CNS following intranasal administration", Molecular Genetics and Metabolism, 106(1), (2012), 131-134.

Wolf, Daniel A., et al., "Direct gene transfer to the CNS prevents emergence of neurologic disease in a murine model of mucopolysaccharidosis type I", HHS Public Access, published in final edited form as: Neurobiology of Disease, 43(1), 123-133, (2011), 26 pgs.

Zheng, Y., et al., "Treatment of the mouse model of mucopolysaccharidosis I with retrovirally transduced bone marrow", Molecular Genetics and Metabolism, 79(4), (2003), 233-244.

"U.S. Appl. No. 15/593,039, PTO Response to Rule 312 Communication mailed Oct. 9, 2018", 2 pgs.

"U.S. Appl. No. 15/717,450, Response filed Nov. 6, 2018 to Non-Final Office Action mailed Aug. 10, 2018", 11 pgs.

"U.S. Appl. No. 15/813,908, Response filed Nov. 12, 2018 to Non-Final Office Action mailed Aug. 10, 2018", 9 pgs.

"U.S. Appl. No. 15/995,045, Response filed Dec. 10, 2018 to Non-Final Office Action mailed Sep. 10, 2018", 7 pgs.

"U.S. Appl. No. 15/995,055, Response filed Nov. 19, 2018 to Non-Final Office Action mailed Aug. 31, 2018", 8 pgs.

"U.S. Appl. No. 15/170,556, Response filed Oct. 29, 2018 to Non-Final Office Action mailed Jul. 27, 2018", 9 pgs.

"Chinese Application Serial No. 201680037625.2, Voluntary Amendment filed Nov. 30, 2018", (w/ English Translation of Claims), 13 pgs.

"Chinese Application Serial No. 201480027622.1, Office Action mailed Oct. 29, 2018", (w/ English Translation), 20 pgs.

"Mexican Application Serial No. MX/a/2015/015560, Response filed Oct. 1, 2018 to Office Action mailed Jul. 2, 2018", (w/ English Translation of Claims), 14 pgs.

Brady, Roscoe O., "Enzyme Replacement for Lysosomal Diseases", *Annu. Rev. Med.*, 57, (2006), 283-296.

"U.S. Appl. No. 15/717,450, Non Final Office Action mailed Aug. 10, 2018", 19 pgs.

"U.S. Appl. No. 15/813,908, Non Final Office Action mailed Aug. 10, 2018", 26 pgs.

"U.S. Appl. No. 15/987,490, Non Final Office Action mailed Sep. 10, 2018", 11 pgs.

"U.S. Appl. No. 15/989,405, Non Final Office Action mailed Aug. 31, 2018", 16 pgs.

(56) References Cited

OTHER PUBLICATIONS

"U.S. Appl. No. 15/995,045, Non Final Office Action mailed Sep. 10, 2018", 13 pgs.
"U.S. Appl. No. 15/995,055, Non Final Office Action mailed Aug. 31, 2018", 16 pgs.
"Chinese Application Serial No. 201480027622.1, Response filed Jun. 22, 2018 to Office Action mailed Apr. 8, 2018", (w/ English Translation of Claims), 16 pgs.
"European Application Serial No. 14798331.6, Response filed Sep. 14, 2018 to Communication Pursuant to Article 94(3) EPC mailed Apr. 20, 2018", 18 pgs.
"Japanese Application Serial No. 2016-514092, Written Argument and Amendment filed Aug. 10, 2018 to Office Action mailed Feb. 14, 2018", (w/ English Translation), 19 pgs.
"Pompe Disease—Genetic Home Referencese", website: ghr.nlm.nih.gov/condition/pompe-disease U.S. National Library of Medicine, (Sep. 4, 2018), 1-5.
"Russian Application Serial No. 2015152546, Response filed Aug. 2, 2018 to Office Action and Search Report mailed Apr. 11, 2018", (w/ English Translation of Amended Claims), 9 pgs.
"The factsheet of Mucopolysaccharidosis type III", Genetics Home Reference from US National Library of Medicine, (Aug. 5, 18), 6 pgs.
"The factsheet of Mucopolysaccharidosis type III from OMIM", [Online]. [retrieved on Aug. 6, 2018]. Retrieved from the Internet: <URL: www.omim.org/entry/252900>, (Aug. 5, 2018), 10 pgs.
Bennett, Michael J., et al., "The Neuronal Ceroid-Lipofuscinoses", Dev. Disabil. Res. Rev. 17(1), (2013), 254-259.
Esposito, Sabrina, et al., "Heparan N-sulfatase gene: two novel mutations and transient expression of 15 defects", Biochimica et Biphysica Acta, 1501, (2000), 1-11.
Fietz, Micheal, et al., "Diagnosis of neuronal ceroid lipofuscinosis type 2 (CLN2 disease): Expert recommendations for early detection and laboratory diagnosis", Mol. Genet. Metab, 119, (2016), 160-167.
Sundhi, Dolan, et al., "Long-Term Expression and Safety of Administration of AAVrh. 10hCLN2 to the Brain of Rats and Nonhuman Primates for the Treatment of Late Infantile Neuronal Ceroid Lipofuscinosis", Hum. Gene Ther. Meth. 23(5), (2012), 324-335.
"Abstract List, American Society of Gene & Cell Therapy (ASGCT), 17th Annual Meeting May 21-24, 2014 Washington DC,", Mol. Ther., vol. 22, Suppl. 1, S1-S334, (Apr. 26, 2014), 134 pgs.
"U.S. Appl. No. 15/574,432, Non Final Office Action mailed May 2, 2019", 17 pgs.
"U.S. Appl. No. 15/717,450, Non Final Office Action mailed Feb. 25, 2019", 23 pgs.
"U.S. Appl. No. 15/813,908, Final Office Action mailed Feb. 25, 2019", 27 pgs.
"U.S. Appl. No. 15/995,045, Final Office Action mailed Jan. 2, 2019", 15 pgs.
"U.S. Appl. No. 15/995,055, Final Office Action mailed Mar. 7, 2019", 20 pgs.
"U.S. Appl. No. 16/461,271, Preliminary Amendment filed May 15, 2019", 6 pgs.
"Australian Application Serial No. 2014265417, Statement of Proposed Amendments filed Jan. 15, 2019", 12 pgs.
"Chinese Application Serial No. 201480027622.1, Response to OA due Chinese Application Serial No. 201480027622.1, Response filed Mar. 13, 2019 to Office Action mailed Oct. 28, 2018", w/English claims, 99 pgs.
"European Application Serial No. 14798331.6, Summons to Attend Oral Proceedings mailed Jan. 28, 2019", 9 pgs.
"European Application Serial No. 16797013.6, Extended European Search Report mailed Dec. 19, 2018", 9 pgs.
"European Application Serial No. 16797013.6, Office Action mailed Jan. 8, 2019", 1 pg.
"Indian Application Seria No. 11403/DELNP/2015, First Examination Report maild Jan. 9, 2019", 5 pgs.
"Japanese Application Serial No. 2016-514092, Notification of Reasons for Refusal/Rejection mailed Jan. 10, 2019", (w/ English Translation), 8 pgs.
"Mexican Application Serial No. MX/a/2015/015560, Office Action mailed Feb. 20, 2019", (English Translation), 2 pgs.
"Mexican Application Serial No. MX/a/2015/015560, Response filed Apr. 4, 2019 to Office Action mailed Feb. 20, 2019", w/ English Claims, 12 pgs.
"Russian Application Serial No. 2015152546, Office Action mailed Sep. 26, 2018", (w/ English Translation), 7 pgs.
"Russian Application Serial No. 2015152546, Response filed Mar. 26, 2019 to Office Action mailed Sep. 26, 2018", (w/ English Translation of Claims), 6 pgs.
"Singaporean Application Serial No. 11201709006T, Search Report mailed Jan. 22, 2019", 3 pgs.
"Singaporean Application Serial No. 11201709006T, Written Opinion mailed Jan. 22, 2019", 7 pgs.
Arruda, "Strategies to Modulate Immune Responses: A New Frontier for Gene Therapy", Molecular Therapy, (2009), 1492-1503.
Belur, L, et al., "High Level Expression of Human Iduronidase Throughout the Brain in a Murine Model of Mucpolysaccharidosis Type I After Non-Invasive AAV-Mediated Gene Delivery to the CNS", (Abstract 610), Molecular Therapy, vol. 22, Supplement 1, (May 2014), p. S236.
Dayton, R. D., et al., "The advent of AAV9 expands applications for brain and spinal cord gene delivery", NIH Public Access, Author Manuscript, published in final edited form as: Expert Opin Biol Ther. 12(6):757-766, (2012), 17 pages.
Gagliardi, et al., "Large Animal Models of Neurological Disorders for Gene Therapy", ILAR J. 50(2), (2009), 128-143.
Gray, S J, et al., "Global CNS gene delivery and evasion of anti-AAV-neutralizing antibodies by intrathecal AAV administration in non-human primates.", Gene Therapy, 20(4), (2013), 450-459.
Gray, S. J., "Gene therapy and neurodevelopmental disorders", Neuropharmacology, 68, (2013), 136-142.
Lykken, et al., "Recent progress and considerations for AAV gene therapies targeting the central nervous system", Journal of Neurodevelopmental Disorders, (2018), 1-10.
McIvor, R. S., et al., "Intrathecal and intranasal infusion of adeno-associated virus vector: non-invasive routes of administration achieving corrective levels of iduronidase expression throughout the brain for gene therapy of mucopolysaccharidosis type I", (Abstract 162), Mol. Gen. Metab., vol. 111, (2014), S75-S76.
Miyake, N., et al., "Gene Therapy of Adult MLD Model Mice by Intrathecal Administration of Type 9 AAV Vector", (Abstract 31), Molecular Therapy, vol. 20, Supplement 1, (May 2012), p. S13.
Miyake, Noriko, "Intrathecal Administration of Type 9 AAV Vector Expressing Arylsulfatase A is Effective for Reduction of Sulfatide Storage but Not for Correction of Neurological Deficits in Adult Metachromatic Leukodystrophy Model Mice with Overt Neurological Symptoms", Abstract 723, Molecular Therapy, 19(Suppl. 1), (May 2011), p. S276.
Pena, Ana, "Potential Therapeutic TargetAgains SMA is Identified", https:/smanewstoday.com/2018/03/14study-identified-therapeutic-target-against-spinal-m . . . , Study Identified New Therapeutic Target Against Spinal Muscular Atrophy, (Mar. 14, 2018).
Stanimirovic, et al., "Emerging Technologies for Delivery of Biotherapeutics and Gene Therapy Across the Blood-Brain Barrier", BioDrugs, 32, (2018), 547-559.
"U.S. Appl. No. 15/717,450, Response filed May 24, 2019 to Non-Final Office Action mailed Feb. 25, 2019", 11 pgs.
"U.S. Appl. No. 15/813,908, Advisory Action mailed Jul. 1, 2019", 5 pgs.
"U.S. Appl. No. 15/813,908, Response filed May 24, 2019 to Final Office Action mailed Feb. 25, 2019", 10 pgs.
"U.S. Appl. No. 15/995,045, Advisory Action mailed Jul. 1, 2019", 3 pgs.
"U.S. Appl. No. 15/995,045, Response filed Jun. 3, 2019 to Final Office Action mailed Jan. 2, 2019", 8 pgs.
"U.S. Appl. No. 15/995,055, Advisory Action mailed Jul. 1, 2019", 3 pgs.
"U.S. Appl. No. 15/995,055, Examiner Interview Summary mailed Jul. 16, 2019", 3 pgs.

(56) References Cited

OTHER PUBLICATIONS

"U.S. Appl. No. 15/995,055, Response filed Jun. 3, 2019 to Final Office Action mailed Mar. 7, 2019", 10 pgs.
"U.S. Appl. No. 16/438,143, Restriction Requirement mailed Jul. 1, 2019", 7 pgs.
"Chinese Application Serial No. 201480027622.1, Office Action mailed May 15, 2019", (w/ English Translation), 18 pgs.
"European Application Serial No. 16797013.6, Response filed Jul. 11, 2019 to Office Action mailed Jan. 8, 2019", 6 pgs.
"International Application Serial No. PCT/US2017/061838, International Preliminary Report on Patentability mailed May 31, 2019", 10 pgs.
"Japanese Application Serial No. 2016-514092, Response filed Jul. 4, 2019 to Notification of Reasons for Refusal/Rejection mailed Jan. 10, 2019", (w/ English Translation of Claims), 16 pgs.
"Singaporean Application Serial No. 11201709006T, Response filed Jun. 20, 2019 to Written Opinion mailed Jan. 22, 2019", 17 pgs.
Bailey, L., "An Overview of Enzyme Replacement Therapy for Lysosomal Storage Diseases", OJIN: The Online Journal of Issues in Nursing, 13(1), Manuscript 3, (2008), 1 pg.
Harding, T. C., et al., "AAV Serotype 8-Mediated Gene Delivery of a Soluble VEGF Receptor to the CNS for the Treatment of Glioblastoma", Mol. Ther., 13(5), (May 2006), 956-966.
Hicks, M. J., et al., "AAV-Directed Persistent Expression of a Gene Encoding Anti-Nicotine Antibody for Smoking Cessation", Sci. Transl. Med., 4(140): 140ra87, (2012), 1-7.
Jalanko, Anu, et al., "Neuronal ceroid lipofuscinoses", Biochimica et Biophysica Acta 1793, (2009), 697-709.
Mao, Yanxiong, et al., "Persistent Suppression of Ocular Neovascularization with Intravitreal Administration of AAVrh.10 Coding for Bevacizumab", Human Gene Ther., 22(12), (2011), 1525-1535.
Wang, Guoqing, et al., "Persistent Expression of Biologically Active Anti-HER2 Antiboy by AAVrh.10-mediated Gene Transfer", Cancer Gene Ther., 17(8), (2010), 559-570.
Watanabe, M., et al., "AAVrh.10-mediated genetic delivery of bevacizumab to the pleura to provide local anti-VEGF to suppress growth of metastatic lung tumors", Gene Therapy, 17(8), (2010), 1042-1051.
U.S. Appl. No. 16/438,143, filed Jun. 11, 2019, Adeno-Associated Virus Mediated Gene Transfer to The Central Nervous System.
U.S. Appl. No. 16/461,271, filed May 15, 2019, Method for Improving Neurological Function in MPSI and MPSII and Other Neurological Disorders.
"U.S. Appl. No. 15/574,432, Examiner Interview Summary mailed Jul. 6, 2020", 3 pgs.
"U.S. Appl. No. 15/813,908, Response filed Jun. 19, 2020 to Non-Final Office Action mailed Mar. 19, 2020", 12 pgs.
"U.S. Appl. No. 15/995,045, Final Office Action mailed Jun. 11, 2020", 22 pgs.
"U.S. Appl. No. 15/995,055, Non-Final Office Action mailed May 29, 2020", 39 pgs.
"U.S. Appl. No. 16/438,143, Final Office Action mailed Jun. 11, 2020", 21 pgs.
"U.S. Appl. No. 16/461,271, Restriction Requirement mailed Jun. 1, 2020", 5 pgs.
"Australian Application Serial No. 2018253615, Subsequent Examiners Report mailed May 20, 2020", 4 pgs.
"Korean Application Serial No. 10-2015-7035379, Request for Examination", (w/ English Translation of Claims), 18 pgs.
"Russian Application Serial No. 2017143640, Response filed May 22, 2020 to Office Action mailed Nov. 22, 2019", w/English Claims, 9 pgs.
"Singaporean Application Serial No. 11201709006T, Response filed Jun. 15, 2020 to Written Opinion mailed Jan. 14, 2020", 14 pgs.
"Singaporean Application Serial No. 11201709006T, Response filed Jun. 15, 2020 to Written Opinion mailed Jan. 22, 2019", 9 pgs.
Aharon-Peretz, Judith, et al., "Mutations in the glucocerebrosidase gene and Parkinson disease: Phenotype-genotype correlation", Neurology, 65, (2005), 1460-1461.
Byrne, Barry J., "Phase II Study of AAV9-GAA gene transfer in Pompe Disease", [online]. NIH website. [retrieved on Feb. 18, 2019]. Retrieved from the Internet: <URL: <grantome.com/grant/NIH/U01-HL121842-01A1>, (2015), 4 pgs.
Clearley, Cassia N., et al., "Transduction Characteristics of Adeno-associated Virus Vectors Expressing Cap Serotypes 7, 8, 9, and Rh10 in the Mouse Brain", Mol. Thera, 13, (2006), 528-537.
Sondhi, D, et al., "Survival Advantage of Neonatal CNS Gene Transfer for Late Infantile Neuronal Ceroid Lipofuscinosis", Exp Neurol., vol. 213, No. 1, (2008), 18-27.
"U.S. Appl. No. 15/717,450, Response filed Mar. 3, 2020 to Final Office Action mailed Sep. 3, 2019", 16 pgs.
"U.S. Appl. No. 15/813,908, Non-Final Office Action mailed Mar. 19, 2020", 24 pgs.
"U.S. Appl. No. 15/995,045, Response filed Mar. 3, 2020 to Non-Final Office Action mailed Sep. 3, 2019", 11 pgs.
"U.S. Appl. No. 16/438,143, Response filed Mar. 3, 2020 to Non-Final Office Action mailed Sep. 3, 2019", 9 pgs.
"European Application Serial No. 16797013.6, Communication Pursuant to Article 94(3) EPC mailed Mar. 10, 2020", 5 pgs.
Marco, Sara, et al., "In Vivo Gene Therapy for Mucopolysaccharidosis Type III (Sanfilippo Syndrome): A New Treatment Horizon", Human Gene Therapy, 30(10), (Oct. 2019), 1211-1221.
"U.S. Appl. No. 15/574,432, Response filed Jul. 15, 2020 to Advisory Action mailed May 5, 2020", 12 pgs.
"U.S. Appl. No. 16/461,271, Response filed Jul. 30, 2020 to Restriction Requirement mailed Jun. 1, 2020", 6 pgs.
"Canadian Application Serial No. 2,912,678, Response filed Aug. 21, 2020 to Office Action mailed Apr. 15, 2020", 53 pgs.
"European Application Serial No. 16797013.6, Response filed Jul. 17, 2020 to Communication Pursuant to Article 94(3) EPC mailed Mar. 10, 2020", 10 pgs.
"European Application Serial No. 17809124.5, Communication Pursuant to Article 94(3) EPC mailed Jul. 16, 2020", 7 pgs.
"Indian Application Serial No. 201918027115, Office Action mailed Aug. 31, 2020", 6 pgs.
"Korean Application Serial No. 10-2015-7035379, Office Action mailed Aug. 25, 2020", (w/ English Translation), 13 pgs.
"Singaporean Application Serial No. 11201904342Q, Written Opinion and Search Report mailed Sep. 1, 2020", 13 pgs.
"U.S. Appl. No. 15/574,432, Advisory Action mailed May 5, 2020", 6 pgs.
"U.S. Appl. No. 15/574,432, Response filed Apr. 20, 2020 to Final Office Action mailed Jan. 15, 2020", 11 pgs.
"Australian Application Serial No. 2018253615, Response filed Apr. 28, 2020 to First Examination Report mailed Feb. 14, 2020", 13 pgs.
"Canadian Application Serial No. 2,912,678, Office Action mailed Apr. 15, 2020", 8 pgs.
"Japanese Application Serial No. 2018-511353, Notification of Reasons for Rejection mailed Apr. 6, 2020", (w/ English Translation), 9 pgs.
Sukegawa, Kazuko, "Mucopolysaccharidosis (I-VII), Separate Volume besides Kazuko Sukegawa Syndrome", Series No. 34 Malformation Syndrome Dictionary Classified by Japanese (Beaming), (2001), 211-214 (6 pgs.).
Tanaka, Seiko, "Mucopolysacchari, and Japanese Clinical areas separate from the clinical Areas of Clinical districts", 13. Liver biliary disease (second edition) (I) liver assembly (Upper), (2010), 509-514 (8 pgs.).
"U.S. Appl. No. 15/574,432, Final Office Action mailed Jan. 15, 2020", 17 pgs.
"U.S. Appl. No. 15/574,432, Response filed Oct. 21, 2019 to Non-Final Office Action mailed May 2, 2019", 9 pgs.
"U.S. Appl. No. 15/717,450, Final Office Action mailed Sep. 3, 2019", 27 pgs.
"U.S. Appl. No. 15/813,908, Response filed Aug. 26, 2019 to Advisory Action mailed Jul. 1, 2019", 12 pgs.
"U.S. Appl. No. 15/995,045, Examiner Interview Summary mailed Oct. 8, 2019", 3 pgs.
"U.S. Appl. No. 15/995,045, Non-Final Office Action mailed Sep. 3, 2019", 18 pgs.

(56) References Cited

OTHER PUBLICATIONS

"U.S. Appl. No. 15/995,055, Response filed Sep. 6, 2019 to Advisory Action mailed Jul. 1, 2019", 10 pgs.
"U.S. Appl. No. 16/438,143, Non-Final Office Action mailed Sep. 3, 2019", 14 pgs.
"U.S. Appl. No. 16/438,143, Response filed Aug. 1, 2019 to Restriction Requirement mailed Jul. 1, 2019", 5 pgs.
"Australian Application Serial No. 2018253615, First Examination Report mailed Feb. 14, 2020", 5 pgs.
"Chinese Application Serial No. 201480027622.1, Response filed Aug. 29, 2019 to Office Action mailed May 15, 2019", (w/ English Translation of Claims), 17 pgs.
"European Application Serial No. 19202040.2, Communication pursuant to Rule 56(3) or (5) EPC mailed Nov. 19, 2019", 2 pgs.
"European Application Serial No. 19202040.2, Extended European Search Report mailed Dec. 12, 2019", 22 pgs.
"European Application Serial No. 17809124.5 Response filed Jan. 27, 2020 to Communication pursuant to Rules 161(1) and 162 EPC filed Jul. 16, 2019", 13 pgs.
"Gaucher Disease Clinical Trials", [online]. © 2019 wcg CenterWatch. Retrieved from the Internet: <URL: https://www.centerwatch.com/clinical-trials/listings/condition/626/gaucher-disease/>, (2019), 3 pgs.
"Hunter Syndrome (MPS II) Clinical Trials", [online]. © 2019 wcg CenterWatch. Retrieved from the Internet: <URL: https://www.centerwatch.com/clinical-trials/listings/condition/769/hunter-syndrome-mps-ii/>, (2019), 4 pgs.
"Japanese Application Serial No. 2016-514092, Examiners Decision of Final Refusal mailed Sep. 9, 2019", (w/ English Translation), 10 pgs.
"Mexican Application Serial No. MX/a/2015/015560, Office Action mailed Aug. 1, 2019", (w/ English Translation), 6 pgs.
"Mexican Application Serial No. MX/a/2015/015560, Response filed Jan. 8, 2020 to Office Action mailed Aug. 1, 2019", (w English Translation of Amended Claims), 15 pgs.
"Motor Neuron Diseases Fact Sheet", [online]. NINDS. [archived on Jan. 5, 2017]. Retrieved from the Internet: <URL: https://web.archive.org/web/20170105003647/https://www.ninds.nih.gov/Disorders/Patient-Caregiver-Education/Fact-Sheets/Motor-Neuron-Diseases-Fact-Sheet>, (2017), 13 pgs.
"Russian Application Serial No. 2017143640, Office Action mailed Nov. 22, 2019", w/ English Translation, 9 pgs.
"Sigaporean Application Serial No. 11201709006T, Written Opinion mailed Jan. 14, 2020", 5 pgs.
"Spinal Muscular Atrophy Clinical Trials", [online]. © 2019 wcg CenterWatch. Retrieved from the Internet: <URL: https://www.centerwatch.com/clinical-trials/listings/condition/721/spinal-muscular-atrophy/>, (2019), 3 pgs.
Cardone, M., et al., "Correction of Hunter syndrome in the MPSII mouse model by AAV2/8-mediated gene delivery.", Hum. Mol. Genet., 15(7), (2006), 1225-1236.
Ciron, Carine, et al., "Gene Therapy of the Brain in the Dog Model of Hurler's Syndrome", Annuals of Neurology, 60, (2006), 204-213.
Crystal, Ronald G., "Clinical Protocol—Administration of a Replication-Deficient Adeno-Associated Virus Gene Transfer Vector Expressing the Human CLN2 cDNA to the Brain of Children with Late Infantile Neuronal Ceroid Lipofuscinosis", Human Gene Therapy, 15, (Nov. 2004), 1131-1154.
Escolar, Maria, et al., "RGX-121 gene therapy for severe MPS II (Hunter Syndrome): Interim results of an ongoing first in human trial", 16th Annual WorldSymposium, (Feb. 12, 2020), 1 pg.
Fedele, Anthony O., "Sanfilippo syndrome: causes, consequences, and treatments", The Application of Clinical Genetics, 8, (2015), 269-281.
Haurigot, Virginia, et al., "Whole body correction of mucopolysaccharidosis IIIA by intracerebrospinal fluid gene therapy", Journal of Clinical Investigation; vol. 123, No. 8, 3254-3271, (Aug. 2013), 18 pgs.
Laoharawee, Kanut, et al., "Prevention of Neurocognitive Deficiency in Mucopolysaccharidosis Type II Mice by Central Nervous System-Directed, AAV9-Mediated Iduronate Sulfatase Gene Transfer", Human Gene Therapy, 28(8), (2017), 626-638.
Marco, Sara, et al., "In Vivo Gene Therapy for Mucopolysaccharidosis Type III (Sanfilippo Syndrome): A New Treatment Horizon", (Abstract), Human Gene Therapy, 30(10), 1211-1221, (Oct. 2019), 1 pg.
McArty, Douglas M., "Self-complementary AAV Vectors; Advances and Applications", Molecular Therapy, 16(10), (2008), 1648-1656.
Noreau, Anne, et al., "Clucocerebrosidase Mutations in a French-Canadian Parkinson's Disease Cohort", Can. J. Neurol. Sci., 38(5), (2011), 772-773.
Pena, Anna, "Potential Therapeutic Target Against SMA is Identified", SMA News Today Newsletter, (Mar. 14, 2018).
Salabarria, S. M., et al., "Advancements in AAV-mediated Gene Therapy for Pompe Disease", J. Neuromus. Dis., 7(1), (2019), 15-31.
Sardi, S. Pablo, et al., "Augmenting CNS glucocerebrosidase activity as a therapeutic strategy for parkinsonism and other Gaucher-related synucleinopathies", Proc. Natl. Acad. Sci. USA, 110(9), (2013), 3537-3542.
Schapira, Anthony H. V., et al., "Glucocerebrosidase in the pathogenesis and treatment of Parkinson disease", Proc. Natl. Acad. Sci. USA, 110(9), (2013), 3214-3215.
Schuster, Daniel J., et al., "Biodistribution of adeno-associated virus serotype 9 (AAV9) vector after intrathecal and intravenous delivery in mouse", Frontiers in Neuroanatomy, vol. 8, Article 42, (Jun. 2014), 1-14.
Sondi, Dolan, et al., "Long-Term Expression and Safety of Administration of AAVrh.10hCLN2 to the Brain of Rats and Nonhuman Primates for the Treatment of Late Infantile Neuronal Ceroid Lipofuscinosis", Human Gene Therapy, 23, (Oct. 2012), 324-335.
Supotnitsky, M V, et al., "Genotherapeutic Vector Systems Based on Viruses", Biopreparots, No. 3(43), 15-26, (2011), 24 pgs.
Tardieu, Marc, et al., "Intracerebral Administration of Adeno-Associated Viral Vector Serotype rh.10 Carrying Human SGSH and SUMF1 cDNAs in Children with Mucopolysaccharidosis Type IIIA Disease: Results of a Phase I/II Trial", Human Gene Therapy, 25, (Jun. 2014), 506-516.
Tardieu, Marc, "Intracerebral gene therapy in children with mucopolysaccharidosis type IIIB syndrome: an uncontrolled phase 1/2 clinical trial", Lancet Neurol., 16, (Sep. 2017), 712-720.
Whiteman, David AH, et al., "Development of idursulfase therapy for mucopolysaccharidosis type II (Hunter syndrome): the past, the present and the future", Drug Design Devel. Therapy, 11, (2017), 2467-2480.
Wolf, Daniel A., et al., "Gene therapy for neurologic manifestations of mucopolysaccharidoses", Expert Opinion on Drug Delivery, 12(2), (2015), 283-296.
Worgall, Stefan, et al., "Treatment of Late infantile Neuronal Ceroid Lipofuscinosis by CNS Administration of a Serotype 2 Adeno-Associated Virus Expressing CLN2 cDNA.", Human Gene Therapy, 19(5), (2008), 463-474.
Wraith, J. Edmond, et al., "Mucopolysaccharidosis type II (Hunter syndrome): a clinical review and recommendation for treatment in the era of enzyme replacemnet therapy", Eur. J. Ped. 167(3), (Mar. 2008), 267-277.
Zhang, H., et al., "Several rAAV Vectors Efficiently Cross The Blood-Brain Barrier and Transduce Neurons and Astrocytes in The Neonatal Mouse Central Nervous System", Mol Ther., 19(8), (2011), 1440-1448.
"U.S. Appl. No. 15/574,432, Non Final Office Action mailed Dec. 1, 2020", 18 pgs.
"U.S. Appl. No. 15/717,450, Non Final Office Action mailed Sep. 25, 2020", 33 pgs.
"U.S. Appl. No. 15/813,908, Final Office Action mailed Oct. 1, 2020", 24 pgs.
"U.S. Appl. No. 15/995,055, Final Office Action mailed Mar. 12, 2021", 34 pgs.
"U.S. Appl. No. 15/995,055, Response filed Nov. 25, 2020 to Non Final Office Action mailed May 29, 2020", 13 pgs.
"U.S. Appl. No. 16/461,271, Non Final Office Action mailed Nov. 17, 2020", 10 pgs.

(56) References Cited

OTHER PUBLICATIONS

"U.S. Appl. No. 16/461,271, Response filed Feb. 17, 2021 to Non Final Office Action mailed Nov. 17, 2020", 8 pgs.
"Australian Application Serial No. 2016263119, First Examination Report mailed Mar. 10, 2021", 3 pgs.
"Australian Application Serial No. 2018253615, Response filed Jan. 28, 2021 to Subsequent Examiners Report mailed Dec. 1, 2020", 2 pgs.
"Australian Application Serial No. 2018253615, Response filed Feb. 8, 2021 to Subsequent Examiners Report mailed Feb. 2, 2021", 2 pgs.
"Australian Application Serial No. 2018253615, Response Filed Oct. 20, 2020 to Subsequent Examiners Report mailed May 20, 2020", 9 pgs.
"Australian Application Serial No. 2018253615, Subsequent Examiners Report mailed Feb. 21, 2021", 4 pgs.
"Australian Application Serial No. 2018253615, Subsequent Examiners Report mailed Feb. 11, 2021", 4 pgs.
"Australian Application Serial No. 2018253615, Subsequent Examiners Report mailed Dec. 1, 2020", 4 pgs.
"Brazilian Application Serial No. BR112017024519-1, Petition filed Feb. 8, 2021 in response to Written Opinion mailed Nov. 4, 2020", (w/ English Translation of Petition and Claims), 244 pgs.
"Brazilian Application Serial No. BR112017024519-1, Written Opinion mailed Nov. 4, 2020", (w/ English Translation), 4 pgs.
"Brazilian Application Serial No. BR112019009902-6, Request for Examination", (w/ English Translation of Petition and Proposed Amended Claims), 171 pgs.
"Chinese Application Serial No. 201680037625.2, Office Action mailed Feb. 20, 2021", (w/ Concise Statement of Relevance), 18 pgs.
"Clinical Trial—RGX-121 Gene Therapy in Patients With MPS II (Hunter Syndrome)", NIH, U.S. National Library of Medicine, ClinicalTrials.gov, (First Posted: Jun. 21, 2018), 8 pgs.
"European Application Serial No. 16797013.6, Intention to Grant mailed Dec. 22, 2020", 105 pgs.
"European Application Serial No. 17809124.5, Response filed Nov. 20, 2020 to Communication Pursuant to Article 94(3) EPC mailed Jul. 16, 2020", 9 pgs.
"European Application Serial No. 19202040.2, Response filed Sep. 17, 2020 to Extended European Search Report mailed Dec. 12, 2019", 13 pgs.
"*Homo sapiens* CLN3 lysosomal/endosomal transmembrane protein, battenin (CLN3), RefSeqGene (LRG_689) on chromosome 16", GenBank Accession No. NG_008654 [online]. Retrieved from the Internet: www.ncbi.nlm.nih.gov/nuccore/NG_008654>, (Nov. 19, 2020), 14 pgs.
"*Homo sapiens* CLN6 transmembrane ER protein (CLN6), RefSeqGene on chromosome 15", GenBank Accession No. NG_008764 [online]. Retrieved from the Internet: <URL: www.ncbi.nlm.nih.gov/nuccore/NG_008764.2>, (Oct. 14, 2020), 16 pgs.
"*Homo sapiens* CLN8 transmembrane ER and ERGIC protein (CLN8, RefSeqGene (LRG_691) on chromosome 8", GenBank Accession No. NG_008656 [online]. Retrieved from the Internet: www.ncbi.nlm.nih.gov/nuccore/NG_008656.2>, (Sep. 11, 2020), 11 pgs.
"*Homo sapiens* palmitoyl-protein thioesterase 1 (PPT1), RefSeqGene (LRG_690) on chromosome 1", GenBank Accession No. NG_009192 [online]. Retrieved from the Internet: www.ncbi.nlm.nih.gov/nuccore/NG_009192.1>, (Nov. 23, 2020), 20 pgs.
"*Homo sapiens* tripeptidyl peptidase 1 (TPP1), RefSeqGene on chromosome 11", Accession No. NG_008653 [online]. Retrieved from the Internet: <URL: https://www.ncbi.nlm.nih.gov/nuccore/NG_008653.1>, (Oct. 14, 2020), 9 pgs.
"Human DNA sequence from clone RP11-115D7 on chromosome 1, complete sequence", GenBank Accession No. AL512599 [online]. Retrieved from the Internet: www.ncbi.nlm.nih.gov/nuccore/AL512599.33>, (Jan. 24, 2014), 34 pgs.
"Japanese Application Serial No. 2018-511353, Examiners Decision of Final Refusal mailed Mar. 3, 2021", (w/ English Translation), 6 pgs.
"Japanese Application Serial No. 2018-511353, Written Argument and Amendment filed Oct. 1, 2020 in response to Notification of Reasons for Rejection mailed Apr. 6, 2020", (w/ English Translation), 14 pgs.
"Japanese Application Serial No. 2019-547234, Request for Examination", (w/ English Translation), 11 pgs.
"Japanese Application Serial No. 2020-000741, Notification of Reasons for Refusal mailed Jan. 14, 2021", (w/ English Translation), 6 pgs.
"Korean Application Serial No. 10-2015-7035379, Notice of Preliminary Rejection mailed Feb. 10, 2021", (w/ English Translation), 10 pgs.
"Korean Application Serial No. 10-2015-7035379, Response filed Oct. 26, 2020 to Request for Examination", (w/ English Translation), 40 pgs.
"Korean Application Serial No. 10-2019-7017114, Request for Examination filed Nov. 16, 2020", (w/ English Translation), 22 pgs.
"Mexican Application Serial No. MX/a/2015/015560, Office Action mailed Jul. 27, 2020", (w/ English Translation), 18 pgs.
"Mexican Application Serial No. MX/a/2015/015560, Response filed Dec. 17, 2020 to Office Action mailed Jul. 27, 2020", (w/ English Translation), 15 pgs.
"News Releases—Regenxbio Announces Interim Data from Phase I/II Trial of Mucopolysaccharidosis Type II (MPS II)", (Dec. 18, 2019), 9 pgs.
"Regenxbio Presents Additional Positive Interim Data from Phase I/II Trial of RGX-121 for the Treatment of MPS II (Hunter Syndrome) at the 17th Annual World Symposium tm 2021", Press Release, (Feb. 2021), 4 pgs.
"Russian Application Serial No. 2017143640, Decision to Grant mailed Jun. 11, 2020", (w/ English Translation), 17 pgs.
"Russian Patent Application Serial No. 2019118583, Office Action mailed Jun. 27, 2019", (w/ English Translation), 6 pgs.
"Russian Patent Application Serial No. 2019118583, Response filed Sep. 27, 2019 to Office Action mailed Jun. 27, 2019", (w/ English Translation), 7 pgs.
"Singaporean Application Serial No. 11201904342Q, Response filed Feb. 1, 2021 to Written Opinion and Search Report mailed Sep. 1, 2020", 10 pgs.
"Toxin 2, partial [Bothrops jararaca]", GenBank Accession No. AC091564 [online]. Retrieved via the Internet: <www.ncbi.nlm.nih.gov/protein/AC091564>, (Jul. 24, 2016), 1 pg.
Aronovich, E. L., et al., "Lysosomal storage disease: gene therapy on both sides of the blood-brain barrier", Mol Genet Metab. 114(2), (Feb. 2015), 83-93.
Belur, Lalitha, "Comparative systemic and neurologic effectiveness of intravenous and intrathecal AAV9 delivered individually or combined in a murine model of mucopolysaccharidosis type I", Power Point Presentation, Center for Genome Engineering, University of Minnesota, (Feb. 8, 2021), 15 pgs.
Belur, Lalitha R., et al., "Intravenous delivery for treatment and mucopolysaccharidosis type I: A comparison a AAV serotypes 9 and rh10", Mol. Gen. and Metab. Rep., 24:e100604, (May 20, 2020), 1-8.
Braunlin, Elizabeth, "Cardiac Features of Mucopolysaccharidoses", WedsPres_03_Braunli_Cardiac Features inMPS (Dec. 19, 2011), (2019), 29 pgs.
Broomfield, A., et al., "Ten years of enzyme replacement therapy in paediatric onset mucopolysaccharidosis II in England", Molecular Genetics and Metabolism https://dot.org/10/1016/j.ymgme.219.07.016, Aricle in Press, 8 pgs.
Fraldi, Alessandro, et al., "Functional correction of CNS lesions in an MPS-IIIA mouse model by intracerebral AAV-mediated delivery of sulfamidase and SUMF1 genes", Hum. Mol. Genet, 16, (2007), 2693-2702.
Laoharawee, K., et al., "AAV9 Mediated Correction of Iduronate-2-Sulfatase Deficiency in the Central Nervous System of Mucopolysaccharidosis Type II Mice", Molecular Therapy vol. 23, Supplement 1, (May 2015), S146.

(56) References Cited

OTHER PUBLICATIONS

Lum, Su Han, et al., "Long term survival and cardiopulmonary outcome in children with Hurler syndrome after haematopoietic stem cell transplantation", J Inherit Metab Dis (2017) 40:455-460, (2017), 6 pgs.

Nevoret, Marie-Laure, et al., "RGX-121 Gene Therapy for Severe Mucopolysaccharidosis Type II (MPS II): Interim Results of an Ongoing First in Human Trial", Poster, World Symposium, (Feb. 2021), 1 pg.

Nevoret, Marie-Laure, "RGX-121 Gene Therapy for Severe Mucopolysaccharidosis Type II (MPS II): Interim Results of an Ongoing First in Human Trial", Power Point Presentation, (Feb. 11, 2021), 20 pgs.

Ruzo, Albert, et al., "Correction of Pathological Accumulation of Glycosaminoglycans in Central Nervous System and Peripheral Tissues of MPSIIIA Mice Through Systemic AAV9 Gene Transfer", Hum. Gene Therapy, 23, (2012), 1237-1246.

Sondhi, Dolan, et al., "Long-Term Expression and Safety of Administration of AAVrh.10hCLN2 to the Brain of Rats and Nonhuman Primates for the Treatment of Late Infantile Neuronal Ceroid Lipofuscinosis", Hum. Gene Thera. Methods, 23, (Oct. 2012), 324-335.

Taylor, Madeleine, et al., "Hematopoietic Stem Cell Transplantation for Mucopolysaccharidoses: Past, Present, and Future", Biol Blood Marrow Transplant 25 (2019) e226-e246, journal homepage: www.bbmt.org, (2019), 21 pgs.

Wang, Yanjiang, "Experimental Study of Aβ Clearance in the Brain of Alzheimer's Disease Mice and Epidemiological Study on Protective Factors of Cognitive Impairment", (w/ English Abstract), China Excellent Doctoral Dissertation Full-text Database (PhD)—Medical and Health Technology Series, Issue 11 / Nov. 15, 2005, (2006), 1-124 (129 pgs.).

Yund, B., et al., "Cognitive, Medical, and Neuroimaging Characteristics of Attenuated Mucopolysaccharidosis Type II", Mol Genet Metab. 114(2), (2014), 170-177.

"Indian Application Serial No. 201918027115, Response filed Feb. 22, 2021 to Office Action". (w/ English Translation), 40 pgs.

"U.S. Appl. No. 15/813,908, Response filed Mar. 15, 2022 to Non-Final Office Action mailed Sep. 15, 2021", 12 pgs.

"U.S. Appl. No. 17/574,118, Preliminary Amendment filed Jan. 12, 2022", 7 pgs.

"Brazilian Application Serial No. BR112015028605-4, Response filed Dec. 20, 2021 to Office Action mailed Sep. 6, 2021", (w/ English Translation of Claims), 106 pgs.

"Canadian Application Serial No. 2,912,678, Non Final Office Action mailed Mar. 17, 2022", 5 pgs.

"Chinese Application Serial No. 201480027622.1, Decision of Reexamination—Upholding Rejection mailed Jan. 24, 2022", (w/ English Translation), 35 pgs.

"Chinese Application Serial No. 201680037625.2, Office Action mailed May 5, 2022", (w/ English Translation, 21 pgs.

"Chinese Application Serial No. 201680037625.2, Response filed Feb. 22, 2022 to Office Action mailed Oct. 8, 2021", (w/ English Translation of Claims), 192 pgs.

"European Application Serial No. 17809124.5, Communication Pursuant to Article 94(3) EPC mailed Mar. 30, 2022", 5 pgs.

"European Application Serial No. 21201643.0, Extended European Search Report mailed Apr. 26, 2022", 10 pgs.

"International Application Serial No. PCT/US2022/015294, International Search Report mailed Jun. 3, 2022", 6 pgs.

"International Application Serial No. PCT/US2022/015294, Written Opinion mailed Jun. 3, 2022", 6 pgs.

"Japanese Application Serial No. 2019-547234, Response filed Apr. 7, 2022 to Notification of Reasons for Refusal mailed Oct. 13, 2021", (w/ English Translation of Claims), 97 pgs.

"Japanese Application Serial No. 2021-111318, Examiners Decision of Final Refusal mailed Mar. 17, 2022", (w/ English Translation), 8 pgs.

"Japanese Application Serial No. 2021-111318, Response filed Mar. 1, 2022 to Notification of Reasons for Rejection mailed Sep. 1, 2021", (w/ English Translation of Claims), 98 pgs.

"Japanese Application Serial No. 2022-024452, Notification of Reasons for Refusal mailed May 16, 2022", (w/ English Translation), 10 pgs.

"Japanese Application Serial No. 2022-024452, Voluntary Amendment filed Apr. 13, 2022", (w/ English Translation of Claims), 6 pgs.

"Korean Application Serial No. 10-2015-7035379, Notice of Preliminary Rejection mailed Feb. 14, 2022", (w/ English Translation), 10 pgs.

"Korean Application Serial No. 10-2015-7035379, Response filed Jan. 19, 2022 to Final Office Action mailed Oct. 20, 2021", (w/ English Translation of Claims), 21 pgs.

"Korean Application Serial No. 10-2017-7036062, Response filed Feb. 24, 2022 to Notice of Preliminary Rejection mailed Aug. 24, 2021", (w/ English Translation of Claims), 10 pgs.

"Mexican Application Serial No. MX/a/2017/014443, Response filed Feb. 4, 2022 to Office Action mailed Jun. 1, 2021", (w/ English Translation of Claims), 8 pgs.

"New Zealand Application Serial No. 738386, Response filed Mar. 23, 2022 to Subsequent Examiner Report mailed Dec. 15, 2021", 209 pgs.

"New Zealand Application Serial No. 738386, Subsequent Examiner Report mailed Feb. 8, 2022", 5 pgs.

"New Zealand Application Serial No. 738386, Subsequent Examiner Report mailed Dec. 15, 2021", 4 pgs.

"Singaporean Application Serial No. 10201710448S, Search Report and Written Opinion mailed Mar. 4, 2022", 7 pgs.

"Singaporean Application Serial No. 10201710448S, Search Report and Written Opinion mailed Mar. 8, 2022", 7 pgs.

Belur, L., "Non-Invasive Intranasal Administration of AAV9-Iduronidase Prevents Emergence of Neurologic Disease and Neurocognitive Dysfunction in a Murine Model of Mucopolysaccharidosis Type 1", Abstract 706, Genetic Disorders and Metabolic Liver Disease, vol. 23, Supp. 1, (2015), p. S281.

Polito, V. A., "IDS Crossing of the Blood-Brain Barrier Corrects CNS Defects in MPS II Mice", The American Journal of Human Genetics vol. 85, (2009), 296-301.

Wang, Raymond Y., "RGX-111 Gene Therapy for the Treatmnet of Severe Mucopolysaccharidosis Type I: Interim Anaylsis of the First in Human Study and a Single Patient IND", Division of Metabolic Disorders, CHOC Children's Hospital / Department of Pediatrics, University of California, Irvine, CA WORDLSymposium, Wednesday, Feb. 9, 2022.

"U.S. Appl. No. 15/574,432, Final Office Action mailed Jul. 12, 2021", 19 pgs.

"U.S. Appl. No. 15/574,432, Response filed Apr. 21, 2021 to Non-Final Office Action mailed Dec. 1, 2020", 10 pgs.

"U.S. Appl. No. 15/813,908, Non-Final Office Action mailed Sep. 15, 2021", 22 pgs.

"U.S. Appl. No. 15/813,908, Response filed Mar. 31, 2021 to Final Office Action mailed Oct. 1, 2020", 10 pgs.

"U.S. Appl. No. 16/461,271, Final Office Action mailed Apr. 23, 2021", 9 pgs.

"U.S. Appl. No. 17/212,516, Preliminary Amendment filed Sep. 1, 2021", 5 pgs.

"U.S. Appl. No. 17/344,308, Preliminary Amendment Filed Jun. 10, 2021", 3 pgs.

"U.S. Appl. No. 17/508,714, Preliminary Amendment filed Dec. 17, 2021", 5 pgs.

"Brazilian Application Serial No. BR112015028605-4, Office Action mailed Sep. 6, 2021", (w/ English Translation), 5 pgs.

"Canadian Application Serial No. 2,912,678, Office Action mailed Mar. 31, 2021", 6 pgs.

"Canadian Application Serial 2,912,678, Response filed Aug. 3, 2021 to Office Action mailed Mar. 31, 2021", 8 pgs.

"Canadian Application Serial 2,986,252, Voluntary Amendment filed May 11, 2021", 8 pgs.

"Canadian Application Serial 2,986,252, Office Action mailed Jun. 28, 2021", 5 pgs.

"Canadian Application Serial 2,986,252, Response filed Oct. 28, 2021 to Office Action mailed Jun. 28, 2021", 11 pgs.

(56) References Cited

OTHER PUBLICATIONS

"Chinese Application Serial No. 201480027622.1, Notice of Reexamination mailed Jul. 26, 2021", (w/ English Translation), 20 pgs.
"Chinese Application Serial No. 201480027622.1, Response filed Nov. 9, 2021 to Notice of Reeamination mailed Jul. 26, 2021", (w/ English Translation of Claims), 13 pgs.
"Chinese Application Serial No. 201680037625.2, Office Action mailed Oct. 8, 2021", (w/ English Translation), 16 pgs.
"Chinese Application Serial No. 201680037625.2, Response filed Jul. 7, 2021 to Office Action mailed Feb. 20, 2021", (w/ English Translation of Claims), 13 pgs.
"Indian Application Serial No. 201717045072, First Examination Report mailed Jun. 25, 2021", 7 pgs.
"Japanese Application Serial No. 2019-547234, Notification of Reasons for Refusal mailed Oct. 13, 2021", (w/ English Translation), 8 pgs.
"Japanese Application Serial No. 2020-000741, Examiners Decision of Final Refusal mailed Oct. 21, 2021", (w/ English Translation), 6 pgs.
"Japanese Application Serial No. 2020-000741, Response filed Jul. 13, 2021 to Notification of Reasons for Refusal mailed Jan. 14, 2021", (w/ English Translation of Claims), 33 pgs.
"Japanese Application Serial No. 2021-111318, Notification of Reasons for Rejection mailed Sep. 1, 2021", (w/ English Translation), 8 pgs.
"Korean Application Serial No. 10-2015-7035379, Final Office Action mailed Oct. 20, 2021", (w/ English Translation), 8 pgs.
"Korean Application Serial No. 10-2015-7035379, Written Opinion and Amendment filed Jun. 29, 2021 in response to Notice of Preliminary Rejection mailed Feb. 10, 2021", (w/ English Translation), 25 pgs.
"Korean Application Serial No. 10-2017-7036062, Notice of Preliminary Rejection mailed Aug. 24, 2021", (w/ English Translation), 7 pgs.
"Mexican Application Serial No. MX/a/2017/014443, Office Action mailed Feb. 16, 2021", (English Translation), 2 pgs.
"Mexican Application Serial No. MX/a/2017/014443, Office Action mailed Jun. 1, 2021", (English Translation), 2 pgs.
"Mexican Application Serial No. MX/a/2017/014443, Response filed Jun. 2, 2021 to Office Action mailed Feb. 16, 2021", (w/ English Translation of Claims), 67 pgs.
"MPS II Research Update: Conclusions", (2021), 1 pg.
"New Zealand Application Serial No. 738386, First Examiner Report mailed Jun. 2, 2021", 4 pgs.
"New Zealand Application Serial No. 738386, Response filed Dec. 2, 2021 to First Examiner Report mailed Jun. 2, 2021", 102 pgs.
"Shire Announces Top-Line Results for Phase II/III Clinical Trial in Children with Hunter Syndrome and Cognitive Impairment", (Shire Pharmaceuticals Group), GlobeNewswire, (Dec. 19, 2017), 10 pgs.
Annibali, R., et al., "Hunter syndrome (Mucopolysaccharidosis type II) severe phenotype: long term follow-up on patients undergone to hematopoietic stem cell transplatation", Minerva Pediatr, 65, (2013), 487-496.
Cearley, Cassia N., et al., "Transduction characteristics of adeno-associated virus vectors expressing cap serotypes 7, 8, 9, and Rh10 in the mouse brain", Molecular Therapy, 13(3), (2006), 528-537.
Ciron, C, et al., "Human [alpha]-Iduronidase Gene Transfer Mediated by Adeno-Associated Virus Types 1, 2, and 5 in the Brain of Nonhuman Primates: Vector Diffusion and Biodistribution", Human Gene Therapy, 20(4), (2009), 350-360.
Clarke, Lorne A., et al., "Pathogenesis of skeletal and connective tissue involvement in the mucopolysaccharidoses: glycosaminoglycan storage is merely the instigator", Rheumatology, 50, (2011), V13-V18.
Coletti, Hannah Y., et al., "Long-Term Functional Outcomes of Children with Hurler Syndrome Treated with Unrelated Umbilical Cord Blood Transplantation", BMD Reports, 20, (2015). 77-86.
Di Malta, Chiara, et al., "Autophagy in Astrocytes—A novel culprit in lysosomal storage disorders", Autophagy, 8(12), (2012), 1871-1872.
George, Lindsey, et al., "Multiyear Factor VIII Expression after AAV Gene Transfer for Hemophilia A", New England Journal of Medicine, 385, (2021), 1961-1973.
Giugliani, Roberto, "RGX-121 Gene Therapy for the Treatment of Severe Mucopolysaccharidosis Type II: Interim Analysis of the First in Human Study", ASGCT 2021 Annual Meeting, (2021), 15 pgs.
Hamano, Kimiko, et al., "Mechanisms of neurodegeneration in mucopolysaccharidoses II and IIIB: analysis of human brain tissue", Acta Neuropathol, 15, (2008), 547-559.
Hinderer, Christian, et al., "Delivery of an Adeno-Associated Virus Vector Into Cerebrospinal Fluid Attenuates Central Nervous System Disease in Mucopolysaccharidosis Type II Mice", Human Gene Therapy, 27(11), (2016), 906-915.
Hinderer, Christian, et al., "Intrathecal Gene Therapy Corrects CNS Pathology in a Feline Model of Mucopolysaccharidosis I", Molecular Therapy, 22(12), (Dec. 2014), 2018-2027.
McGlynn, Robert, et al., "Differential Subcellular Localization of Cholesterol, Gangliosides, and Glycosaminoglycans in Murine Models of Mucopolysaccharide Storage Disorders", The Journal of Comparative Neurology, 480, (2004), 415-426.
McKinnis, Elizbeth J. R., et al., "Bone marrow transplation in Hunter syndrome", The Journal of Pediatrics, 129(1), (1996), 145-148.
Muenzer, Joseph, et al., "Comparison of cognitive function in siblings with neuronopathic mucopolysaccharidosis II: evaluation of early treatment with intravenous idursulfase and intrathecal idursulfase-IT", Abstract eP222, Molecular Genetics and Metabolism 132S1, (2021), S142-S143.
Muenzer, Joseph, et al., "Intrathecal idursulfase-IT safety and efficacy in patients with neuronopathic mucopolysaccharidosis II: phase 2/3 extension study 3-year results", Abstract eP216, Molecular Genetics and Metabolism 132S1, (2021), S139-S140.
Muenzer, Joseph, et al., "Long-term safety and efficacy of intrathecal idursulfase-IT in patients with neuronopathic mucopolysaccharidosis type II: 2-year results from a phase 2/3 extension study", Abstract 165, Molecular Genetics and Metabolism 132, (2020), S73-S74.
Muenzer, Joseph, et al., "Safety and efficacy of intrathecal idursulfase-IT in patients <3 years old with neuronopathic mucopolysaccharidosis II: phase 2/3 substudy and extension", Abstract OP096, Molecular Genetics and Metabolim 132S1, (2021), p. S67.
Muenzer, Joseph, et al., "The role of enzyme replacement therapy in severe Hunter syndrome—an expert panel consensus", Eur. J. Pediatr., 171, (2012), 181-188.
Parini, Rossella, et al., "Open issues in Mucopolysaccharidpsos type I-Hurler", Orphanet Journal of Rare Diseases, 12: 112, (2017), 9 pgs.
Settembre, Carmine, et al., "Systemic inflammation and neurodegeneration in a mouse model of multiple sulfatase deficiency", Proc. Natl. Acad. USA, 104(11), (2007), 4506-4511.
Vitner, Einat B., et al., "Common and Uncommon Pathogenic Cascades in Lysosomal Storage Diseases", The Journal of Biological Chemistry, 285(27), (2010), 20423-20427.
Walkley, Steven U., et al., "Pathogenic Cascades in Lysosomal Disease—Why so Complex?", NIH Public Access, Author Manuscript, published in final edited form as: J. Inherit. Matab. Dis., 32(2), (2009), 181-189, (2009), 11 pgs.
Walkley, Steven U., et al., "Secondary lipid accumulation in lysosomal disease", Biochimica et Biophysica Acta, 1793, (2009), 726-736.
Wang, Raymond, et al., "First-in-human Intracisternal Dosing of RGX-111 (Adeno-associated Virus 9 / Human Alpha-I-Iduronidase) for a 20-month-old Child with Mucopolysaccharidosis Type I (MPSI): 1 Year Follow-up", Poster, World Symposium, Feb. 2021, (Feb. 2021), 1 pg.
Wijburg, Frits A., et al., "Long-term safety and clinical outcomes of intrathecal heparan-N-sulfatase in patients with Sanfilippo syndrome type A", Molecular Genetics and Metabolism, (2021), 6 pgs.
Wraith, J. Edmond, et al., "Enzyme Replacement Therapy in Patients Who Have Mucopolysaccharidosis I and are Younger Than 5 Years: Results of a Multinational Study of", Pediatrics, 120, (2007), e37-e46.
U.S. Appl. No. 17/118,395, filed Dec. 10, 2020, Adeno-Associated Virus Mediated Gene Transfer to The Central Nervous System.

(56) References Cited

OTHER PUBLICATIONS

U.S. Appl. No. 17/212,516, filed Mar. 25, 2021, Adeno-Associated Virus Mediated Gene Transfer to The Central Nervous System.
U.S. Appl. No. 18/181,449, filed Mar. 9, 2023, Methods to Treat Pompe Disease Using a Recombinant Adeno-Associated Virus.
U.S. Appl. No. 18/295,063, filed Apr. 3, 2023, Adeno-Associated Virus Mediated Gene Transfer to The Central Nervous System.
U.S. Appl. No. 17/344,308, filed Jun. 10, 2021, Adeno-Associated Virus Mediated Gene Transfer to The Central Nervous System.
U.S. Appl. No. 17/118,353, filed Dec. 10, 2020, Methods to Treat Pompe Disease Using a Recombinant Adeno-Associated Virus.
U.S. Appl. No. 17/574,118, filed Jan. 12, 2022, Intranasal Administration of Adeno-Associated Virus to Treat Central Nervous System Disorders.
U.S. Appl. No. 18/150,740, filed Jan. 5, 2023, Adeno-Associated Virus for Therapeutic Delivery to Central Nervous System.
U.S. Appl. No. 17/508,714, filed Oct. 22, 2021, Method for Improving Neurological Function in MPSI and MPSII and Other Neurological Disorders.
"U.S. Appl. No. 15/813,908, Final Office Action mailed Jul. 5, 2022", 25 pgs.
"Intranasal Administration of Adeno-Associated Virus to Treat Central Nervous System Disorders", U.S. Appl. No. 17/574,118, filed Jan. 12, 2022, 100 pgs.
"Canadian Application Serial No. 2,986,252, Examiner's Rule 86(2) Requisition mailed Jul. 18, 2022, 4 pgs.", 4 pgs.
"Canadian Application Serial No. 2,912,678, Response filed Jul. 18, 2022 to Non Final Office Action mailed Mar. 17, 2022", 86 pgs.
"U.S. Appl. No. 17/118,353, Non Final Office Action mailed Sep. 9, 2022", 24 pgs.
"The factsheet of route of administration from FDA", [Online]. Retrieved from the Internet: URL: www. fda.gov drugs data-standards-manual-monographs route-administration, 6 pgs.
"U.S. Appl. No. 17/118,395, Non Final Office Action mailed Oct. 3, 2022", 24 pgs.
"Singaporean Application Serial No. 11201709006T, Office Action mailed Oct. 5, 2022", (w English Translation), 8 pgs.
"Brazilian Application Serial No. BR112019009902-6, Office Action mailed Oct. 19, 2022", (English Translation), 5 pgs.
"Canadian Application Serial No. 2,986,252, Response filed Nov. 17, 2022 to Examiner's Rule 86(2) Requisition mailed Jul. 18, 2022, 26 pgs.", 26 pgs.
"U.S. Appl. No. 17/212,516, Non Final Office Action mailed Dec. 8, 2022", 28 pgs.
"The factsheet of lysosomal storage diseases from the Cleveland Clinic", my.clevelandclinic.org health diseases 23383-lysosomal-storage-diseases, (Dec. 3, 2022), 14 pgs.
"U.S. Appl. No. 17/344,308, Non Final Office Action mailed Dec. 8, 2022", 13 pgs.
"Brazil Application Serial No. BR 11 2015 028605 4, Office Action mailed Dec. 7, 2022", 6 pgs.
"Singapore Application Serial No. 11201904342Q, Supplementary Search Report mailed Feb. 11, 2022", 3 pgs.
"Singapore Application Serial No. 11201904342Q, Written Opinion mailed Jul. 1, 2022", 10 pgs.
"Brazilian Application Serial No. BR112019009902-6, Response filed Jan. 23, 2023 to Office Action mailed Oct. 19, 2022", w English Claims, 155 pgs.
"Chinese Application Serial No. 202210449484.2, Voluntary Amendment filed Jan. 29, 2023", w English Claims, 7 pgs.
"U.S. Appl. No. 17/344,308, Response filed Mar. 8, 2023 to Non Final Office Action mailed Dec. 8, 2022", 11 pgs.
"Korean Application Serial No. 10-2022-7028291, Response filed Feb. 27, 2023 to Notice of Preliminary Rejection mailed Oct. 27, 2022", w English Claims, 20 pgs.
"U.S. Appl. No. 18/181,1449, Preliminary Amendment Filed Mar. 9, 2023", 3 pgs.
"Indian Application Serial No. 201717045072, Hearing Notice mailed Mar. 15, 2023", 2 pgs.

Belur, Lalitha, "Comparative Effectiveness of Intracerebroventricular, Intrathecal, and Intranasal Routes of AAV9 Vector Administration for Genetic Therapy of Neurologic Disease in Murine Mucopolysaccharidosis Type I", Frontiers in Molecular Neuroscience vol. 14, Article 618360, (May 2021), 1-12.
Hinderer, Christian, "Delivery of an adeno-associated virus vector into cerebrospinal fluid attenuates central nervous system disease in mucopolysaccharidosis type II mice", Human Gene Therapy 27.11, (2016), 906-915.
"U.S. Appl. No. 17/344,308, Final Office Action mailed Mar. 31, 2023", 23 pgs.
"Chinese Application Serial No. 201680037625.2, Response filed Jan. 25, 2023 to Decision of Rejection mailed Oct. 10, 2022" w English Claims, 6 pgs.
"Brazil Application Serial No. BR 11 2015 028605 4, Response filed Mar. 24, 2023 to Office Action mailed Dec. 7, 2022", w English Claims, 163 pgs.
"Indian Application Serial No. 201717045072, Revised Hearing Notice mailed Apr. 13, 2023", 2 pgs.
"European Application Serial No. 19202040.2, Communication Pursuant to Article 94(3) EPC mailed Apr. 4, 2023", 9 pgs.
"Israeli Application Serial No. 266639, Response filed Apr. 30, 2023 to Notification of Defects in Patent Application mailed Oct. 30, 2022", w English Claims, 13 pgs.
"Australian Application Serial No. 2017362969, First Examination Report mailed Apr. 6, 2023", 4 pgs.
"Brazilian Application Serial No. BR112015028605 4, Opinion for non-patenteability (RPI 7.1) mailed May 10, 2023", W English Translation, 10 pgs.
"Indian Application Serial No. 201717045072, Revised Hearing Notice mailed May 19, 2023", 2 pgs.
"Korean Application Serial No. 10-2019-7017114, Response filed May 12, 2023 to Notice of Preliminary Rejection mailed Jan. 12, 2023", w English Claims, 16 pgs.
"Brazilian Application Serial No. BR112015028605-4, Office Action mailed Apr. 25, 2023", w English Translation, 10 pgs.
"Australian Application Serial No. 2017362969, Response filed Sep. 25, 2023 to Office Action mailed Apr. 6, 2023", 39 pgs.
"Australian Application Serial No. 2017362969, Subsequent Examiners Report mailed Oct. 18, 2023", 3 pgs.
"Australian Application Serial No. 2021200982, First Examination Report mailed Oct. 31, 2023", 3 pgs.
"European Application Serial No. 17809124.5, Communication Pursuant to Article 94(3) EPC mailed Oct. 11, 2023", 5 pgs.
"European Application Serial No. 16797013.6, Decision Rejecting the Opposition, mailed Oct. 20, 2023.", (Oct. 17, 2023), 19 pgs.
"Japanese Application Serial No. 2022-193375, Notification of Reasons for Rejection mailed Oct. 30, 2023", W/ English Translation, 6 pgs.
"Korean Application Serial No. 10-2019-7017114, Final Office Action mailed Sep. 25, 2023.", w/ English Translation, 11 pgs.
"Korean Application Serial No. 10-2022-7028291, Response filed Nov. 24, 2023 to Final Office Action mailed Jul. 26, 2023", w/ english claims, 17 pgs.
"Chinese Application Serial No. 202210454541.6, Office Action mailed Jun. 13, 2024", w English Translation, 18 pgs.
"Chinese Application Serial No. 202210449484.2, Office Action mailed Jun. 12, 2024", w English Translation, 19 pgs.
"Singapore Application Serial No. 11202202647X, Response Filed May 29, 2024 to Written Opinion mailed Jan. 17, 2024", 13 pgs.
"European Serial Application No. 22706950.7, Response to Communication pursuant to Rules 161(1) and 162 EPC Filed Jun. 12, 2024", 12 pgs.
Baoheng, Du, "Principles and Practice of Gene Therapy", Tianjin Science and Technology Press, w Machine English Translation, w Machine English Translation, (Jan. 31, 2000), 21 pgs.
Feng, Wei, "Diagnosis and Treatment of Mucopolysaccharidosis", Journal Ofhengyang Medical College (Medical Version), Issue 2, w Machine English Translation, (Jun. 25, 1999), 4 pgs.
Line, Banghe, "Progress in Basic and Clinical Research on Lysosomal Diseases", Journal of Anhui Traditional Chinese Medical College, Issue 2, w Machine English Translation, (Apr. 10, 1993), 12 pgs.

(56) References Cited

OTHER PUBLICATIONS

Wang, Binghe, "Drug Delivery: Principles and Applications", Chemical Industry Press, (Jan. 31, 2008), pp. 22 and 23.

Zheng, Min, "Analysis of clinical characteristics of mucopolysaccharidosis type II", Chinese Journal of Eugenics and Genetics, Issue 1, (Jan. 25, 2013), 2 pgs.

"Australian Application Serial No. 2021266344, Response filed Jul. 26, 2024 to First Examination Report mailed Mar. 22, 2024", 30 pgs.

"Japanese Application Serial No. 2024-113975, Voluntary Amendment filed Aug. 8, 2024", w English claims, 4 pgs.

"U.S. Appl. No. 18/150,740, Restriction Requirement mailed Jul. 18, 2024", 7 pgs.

* cited by examiner

| ROUTE OF ADM. | MICE | CP | AGE AT INJ. | SACRIFICED |
|---|---|---|---|---|
| 1. ICV | IMMUNODEFICIENT | NO | | 10 WKS POST INJ. |
| 2. ICV | IMMUNOCOMPETENT | YES | 4.5 MTHS | 8 WKS POST INJ. |
| 3. INTRATHECAL | IMMUNOCOMPETENT | YES | 4.5 MTHS | 11 WKS POST INJ. |
| 4. ICV | IMMUNOTOLERIZED | NO | 3 MTHS | 9 WKS POST INJ. |

FIG. 1

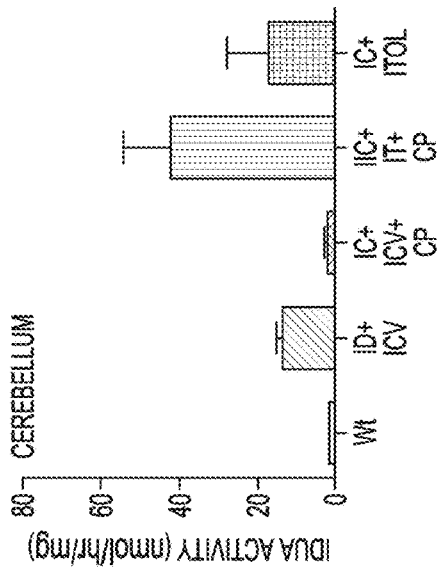
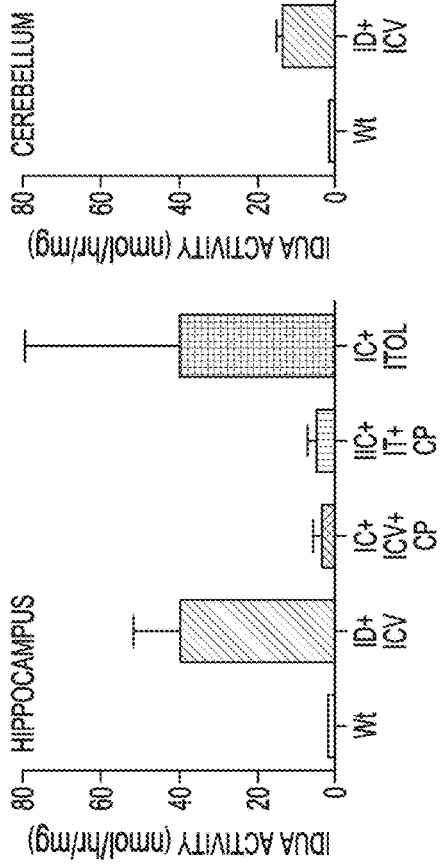
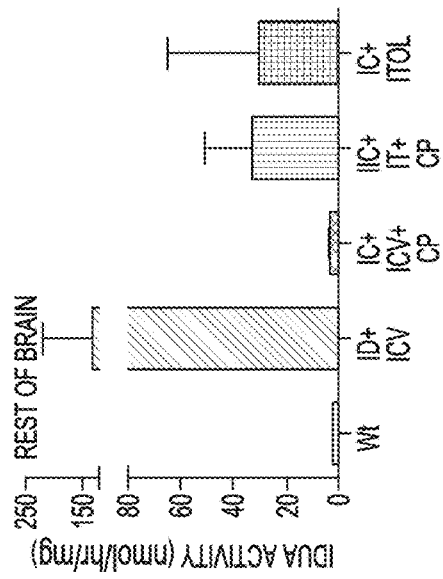
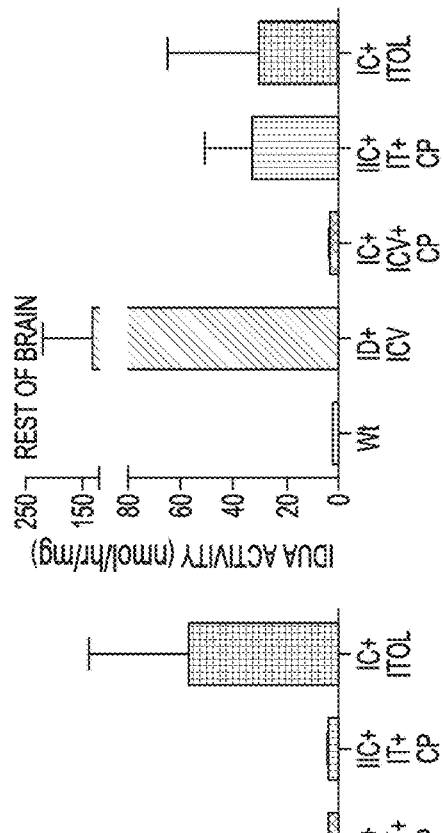
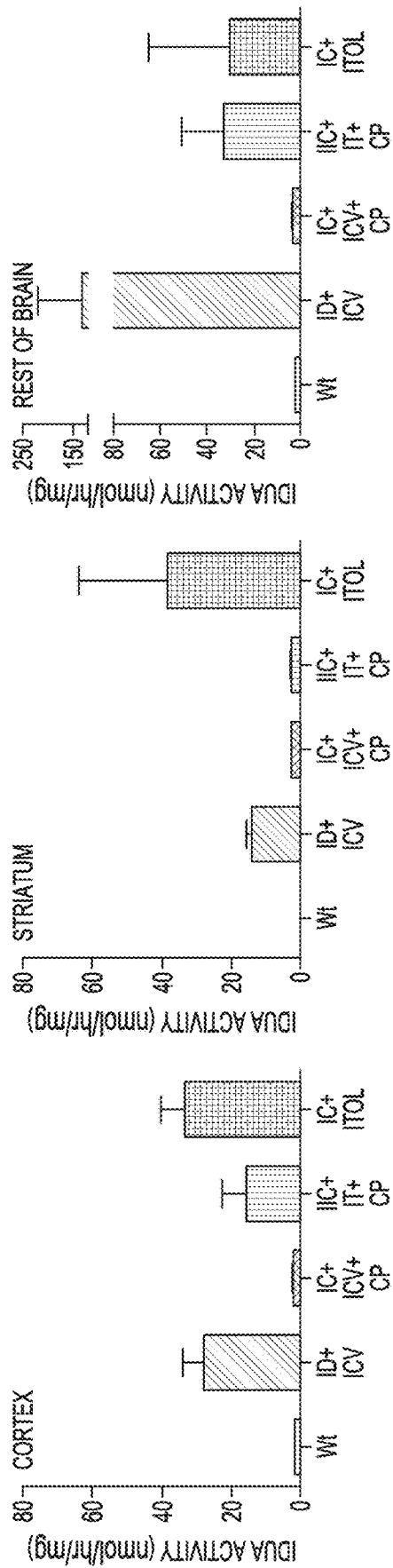

| ROUTE OF VECTOR ADMINISTRATION | IMMUNE COMPETENCY | IMMUNE MODULATION | AGE OF ANIMALS AT INJECTION | EXPT. END POINT (POST-INJECTION) |
|---|---|---|---|---|
| ICV | IMMUNODEFICIENT | NONE | | 10 WEEKS |
| ICV | IMMUNOCOMPETENT | IMMUNOSUPPRESSION W/CP (PARTIAL REGIMEN) | 4.5 MONTHS | 8 WEEKS |
| ICV | IMMUNOCOMPETENT | IMMUNOTOLERIZATION | 4.5 MONTHS | 11 WEEKS |
| ICV | IMMUNOCOMPETENT | NONE | 3 MONTHS | |
| ICV | IMMUNOCOMPETENT | IMMUNOSUPPRESSION W/CP (FULL REGIMEN) | 3 MONTHS | |
| IT | IMMUNOCOMPETENT | IMMUNOSUPPRESSION W/CP (FULL REGIMEN) | 3 MONTHS | 9 WEEKS |
| IT | IMMUNOCOMPETENT | ENZYME TOLERIZATION | 4.5 MONTHS | 10 WEEKS |
| IT | IMMUNOCOMPETENT | NONE | 4.5 MONTHS | 11 WEEKS |

FIG. 9

METHODS TO TREAT MUCOPOLYSACCHARIDOSIS TYPE II OR DEFICIENCY IN IDURONATE-2-SULFATASE USING A RECOMBINANT ADENO-ASSOCIATED VIRUS (AAV) VECTOR ENCODING IDURONATE-2-SULFATASE

CROSS-REFERENCE TO RELATED APPLICATIONS

This application is a divisional of U.S. patent application Ser. No. 14/889,750, filed Nov. 6, 2015, which issued as U.S. Pat. No. 9,827,295, which application is a U.S. National Stage filing under 35 U.S.C. 371 from International Application No. PCT/US2014/038209, filed on May 15, 2014 and published as WO 2014/186579 A1 on 20 Nov. 2014, which claims the benefit of the filing date of U.S. application Ser. No. 61/823,757, filed on May 15, 2013, the disclosure of which is incorporated by reference herein.

STATEMENT OF GOVERNMENT RIGHTS

This invention was made with government support under HD032652 and DK094538 awarded by National Institutes of Health. The Government has certain rights in the invention.

BACKGROUND

The mucopolysaccharidoses (MPSs) are a group of 11 storage diseases caused by disruptions in glycosaminoglycan (GAG) catabolism, leading to their accumulation in lysosomes (Muenzer, 2004; Munoz-Rojas et al., 2008). Manifestations of varying severity include organomegaly, skeletal dysplasias, cardiac and pulmonary obstruction and neurological deterioration. For MPS I, deficiency of iduronidase (IDUA), severity ranges from mild (Scheie syndrome) to moderate (Hurler-Scheie) to severe (Hurler syndrome), with the latter resulting in neurologic deficiency and death by age 15 (Muenzer, 2004; Munoz-Rojas et al., 2008). Therapies for MPSs have been for the most part palliative. However, there are some of the MPS diseases, including Hurler syndrome, for which allogeneic hematopoietic stem cell transplantation (HSCT) has exhibited efficacy (Krivit, 2004; Orchard et al., 2007; Peters et al., 2003). Additionally, for more and more of the MPS diseases, enzyme replacement therapy (ERT) is becoming available (Brady, 2006). In general, HSCT and ERT result in the clearing of storage materials and improved peripheral conditions, although some problems persist after treatment (skeletal, cardiac, corneal clouding). The primary challenge in these cellular and enzyme therapies is effectiveness in addressing neurological manifestations, as peripherally administered enzyme does not penetrate the blood-brain barrier and HSCT has been found to be of benefit for some, but not all, MPS's.

MPS I has been one of the most extensively studied of the MPS diseases for development of cellular and molecular therapies. The effectiveness of allogeneic HSCT is most likely the result of metabolic cross-correction, whereby the missing enzyme is released from donor-derived cells and subsequently taken up by host cells and trafficked to lysosomes, where the enzyme contributes to lysosomal metabolism (Fratantoni et al., 1968). Clearing of GAG storage materials is subsequently observed in peripheral organs such as liver and spleen, there is relief from cardiopulmonary obstruction and improvement in corneal clouding (Orchard et al., 2007). Of particular importance is the effect of allogeneic stem cell transplantation on the emergence of neurologic manifestations in the MPS diseases. In this regard, there is evidence for several MPS diseases that individuals engrafted with allogeneic stem cells face an improved outcome in comparison with untransplanted patients (Bjoraker et al., 2006; Krivit, 2004; Orchard et al., 2007; Peters et al., 2003). A central hypothesis explaining the neurologic benefit of allogeneic hematopoietic stem cell transplant is the penetration of donor-derived hematopoietic cells (most likely microglia) (Hess et al., 2004; Unger et al., 1993) into the central nervous system, where the missing enzyme is expressed by engrafted cells from which point the enzyme diffuses into CNS tissues and participates in clearing of storage materials. The level of enzyme provided to CNS tissues is thus limited to that amount expressed and released from donor-derived cells engrafting in the brain. While such engraftment is of great benefit for MPS I, recipients nonetheless continue to exhibit below normal IQ and impaired neurocognitive capability (Ziegler and Shapiro, 2007).

The phenomenon of metabolic cross correction also explains the effectiveness of ERT for several lysosomal storage diseases (Brady, 2006), most notably MPS I. However, due to the requirement for penetration of the blood-brain barrier (BBB) by the enzyme missing in the particular lysosomal storage disease (LSD) in order to effectively reach the CNS, effectiveness of enzyme therapy for neurologic manifestations of lysosomal storage disease (LSD) has not been observed (Brady, 2006). Enzymes are almost always too large and generally too charged to effectively cross the BBB. This has prompted investigations into invasive intrathecal enzyme administration (Dickson et al., 2007), for which effectiveness has been demonstrated in a canine model of MPS I (Kakkis et al., 2004) and for which human clinical trials are beginning for MPS I (Pastores, 2008; Munoz-Rojas et al., 2008). Key disadvantages of enzyme therapy include its great expense (>$200,000 per year) and the requirement for repeated infusions of recombinant protein. Current clinical trials of intrathecal IDUA administration are designed to inject the enzyme only once every three months, so the effectiveness of this dosing regimen remains uncertain.

SUMMARY OF THE INVENTION

Methods of preventing, inhibiting, and/or treating one or more symptoms associated with a disease of the central nervous system (CNS) in a mammal in need thereof are described. The methods involve delivering to the CNS of a mammal in need of treatment a composition comprising an effective amount of a recombinant adeno-associated virus (rAAV) vector comprising an open reading frame encoding a gene product, e.g., a therapeutic gene product. Target gene products that may be encoded by an rAAV vector include, but are not limited to, alpha-L-iduronidase, iduronate-2-sulfatase, heparan sulfate sulfatase, N-acetyl-alpha-D-glucosaminidase, beta-hexosaminidase, alpha-galactosidase, betagalactosidase, beta-glucuronidase or glucocerebrosidase. Diseases that may be prevented, inhibited or treated using the methods disclosed herein include, but are not limited to, mucopolysaccharidosis type I disorder, a mucopolysaccharidosis type II disorder, or a mucopolysaccharidosis type VII disorder. The AAV vector can be administered in a variety of ways to ensure that it is delivered to the CNS/brain, and that the transgene is successfully transduced in the subject's CNS/brain. Routes of delivery to the CNS/ brain include, but are not limited to intrathecal administration, intracranial administration, e.g., intracerebroventricular administration, or lateral cerebro ventricular administration), intranasal administration, endovascular administration, and intraparenchymal administration.

In one embodiment, the methods involve delivering to the CNS of an adult mammal in need of treatment a composition comprising an effective amount of a rAAV-9 vector comprising an open reading frame encoding a gene. In one embodiment, the methods involve delivering to the CNS of an adult mammal in need of treatment a composition comprising an effective amount of a rAAV-9 vector comprising an open reading frame encoding IDUA. These methods are based, in part, on the discovery that an AAV-9 vector can efficiently transduce the therapeutic transgene in the brain/CNS of adult subjects, restoring enzyme levels to wild type levels. (see FIG. 15, infra). The results achieved using AAV-9 are surprising in view of previous work which demonstrated that intravascular delivery of AAV-9 in adult mice does not achieve widespread direct neuronal targeting (see Foust et al., 2009), as well as additional data showing that direct injection of AAV8-IDUA into the CNS of adult IDUA-deficient mice resulted in poor transgene expression (FIG. 18). As proof of principle, the working examples described herein use a pre-clinical model for the treatment of MPSI, an inherited metabolic disorder caused by deficiency of the lysosomal enzyme alpha-L-iduronidase (IDUA). The working examples surprisingly demonstrate that direct injection of AAV9-IDUA into the CNS of immunocompetent adult IDUA-deficient mice resulted in IDUA enzyme expression and activity that is the same or higher than IDUA enzyme expression and activity in wild-type adult mice (see FIG. 15, infra).

In an additional embodiment of the invention, the working examples also demonstrate that co-therapy to induce immunosuppression or immunotolerization, or treatment of immunodeficient animals, can achieve even higher levels of IDUA enzyme expression and activity. In an embodiment, patients with genotypes that promote an immune response that neutralizes enzyme activity (see, e.g., Barbier et al., 2013) are treated with an immunosuppressant in addition to the rAAV vector comprising an open reading frame encoding a gene product, such as IDUA.

Neonatal IDUA$^{-/-}$ mice are not immunocompetent. However administration of IDUA expressing AAV-8 to neonatal IDUA$^{-/-}$ mice resulted in IDUA expression (Wolf et al., 2011), thus tolerizing the animals to IDUA. As described herein, the applicability of AAV-mediated gene transfer to adult (immunocompetent) mice by direct infusion of AAV to the central nervous system was shown using different routes of administration. For example, AAV-IDUA serotype 9 was administered by direct injection into the lateral ventricles of adult IDUA-deficient mice that were either immunocompetent, immunodeficient (NODSCID/IDUA-/-), immunosuppressed with cyclophosphamide (CP), or immunotolerized by weekly injection of human iduronidase protein (Aldurazyme) starting at birth. CP immunosuppressed animals were also administered AAV9-IDUA by intranasal infusion, by intrathecal injection, and by endovascular infusion with and without mannitol to disrupt the blood-brain barrier. Animals were sacrificed at 8 weeks after vector administration, and brains were harvested and microdissected for evaluation of IDUA enzymatic activity, tissue glycosaminoglycans, and IDUA vector sequences in comparison with normal and affected control mice. Results from these studies show that numerous routes for AAV vector administration directly to the CNS may be employed, e.g., so as to achieve higher levels of protein delivery and/or enzyme activity in the CNS. In addition, although the brain is an immunopriviledged site, administration of an immunosuppressant or immunotolerization may increase the activity found in the brain after MV administration. Higher levels of expression per administration and/or less invasive routes of administration are clinically more palatable to patients.

Thus, the invention includes the use of recombinant AAV (rAAV) vectors that encode a gene product with therapeutic effects when expressed in the CNS of a mammal. In one embodiment, the mammal is an immunocompetent mammal with a disease or disorder of the CNS (a neurologic disease). An "immunocompetent" mammal as used herein is a mammal of an age where both cellular and humoral immune responses are elicited after exposure to an antigenic stimulus, by upregulation of Th1 functions or IFN-γ production in response to polyclonal stimuli, in contrast to a neonate which has innate immunity and immunity derived from the mother, e.g., during gestation or via lactation. An adult mammal that does not have an immunodeficiency disease is an example of an immunocompetent mammal. For example, an immunocompetent human is typically at least 1, 2, 3, 4, 5 or 6 months of age, and includes adult humans without an immunodeficiency disease. In one embodiment, the AAV is administered intrathecally. In one embodiment, the MV is administered intracranially (e.g., intracerebroventricularly). In one embodiment, the AAV is administered intranasally, with or without a permeation enhancer. In one embodiment, the AAV is administered endovascularly, e.g., carotid artery administration, with or without a permeation enhancer. In one embodiment, the mammal that is administered the AAV is immunodeficient or is subjected to immunotolerization or immune suppression, e.g., to induce higher levels of therapeutic protein expression relative to a corresponding mammal that is administered the MV but not subjected to immunotolerization or immune suppression. In one embodiment, an immune suppressive agent is administered to induce immune suppression. In one embodiment, the mammal that is administered the AAV is not subjected to immunotolerization or immune suppression (e.g., administration of the AAV alone provides for the therapeutic effect).

The invention provides a method to prevent, inhibit or treat one or more symptoms associated with a disease or disorder of the central nervous system in a mammal in need thereof. The method includes intrathecally, e.g., to the lumbar region, or intracerebroventricularly, e.g., to the lateral ventricle, administering to the mammal a composition comprising an effective amount of a rAAV vector comprising an open reading frame encoding a gene product, the expression of which in the central nervous system of the mammal prevents, inhibits or treats the one or more symptoms. In one embodiment, the gene product is a lysosomal storage enzyme. In one embodiment, the mammal is an immunocompetent adult. In one embodiment, the rAAV vector is an AAV-1, MV-2, AAV-3, AAV-4, AAV-5, AAV-6, AAV-7, AAV-8, MV rh10, or AAV-9 vector. In one embodiment, the mammal is a human. In one embodiment, multiple doses are administered. In one embodiment, the composition is administered weekly, monthly or two or more months apart.

In one embodiment, the method includes intrathecally, e.g., to the lumbar region, administering to a mammal a composition comprising an effective amount of a rAAV vector comprising an open reading frame encoding a gene product, the expression of which in the central nervous system of the mammal prevents, inhibits or treats the one or more symptoms, and optionally administering a permeation enhancer. In one embodiment, the permeation enhancer is administered before the composition. In one embodiment, the composition comprises a permeation enhancer. In one embodiment, the permeation enhancer is administered after the composition. In one embodiment, the gene product is a lysosomal storage enzyme. In one embodiment, the mammal is an immunocompetent adult. In one embodiment, the rAAV vector is an AAV-1, AAV-3, AAV-4, AAV-5, AAV-6, AAV-7, AAV-8, AAV rh10, or AAV-9 vector. In one embodiment, the mammal is a human. In one embodiment, multiple doses are administered. In one embodiment, the composition is administered weekly, monthly or two or more months apart. In one embodiment, the mammal that is intrathecally administered the AAV is not subjected to immunotolerization or immune suppression (e.g., administration of the AAV alone provides for the therapeutic effect). In one embodiment, the mammal that is intrathecally administered the AAV is immunodeficient or is subjected to immunotolerization or immune suppression, e.g., to induce higher levels of therapeutic protein expression relative to a corresponding mammal that is intrathecally administered the AAV but not subjected to immunotolerization or immune suppression.

In one embodiment, the method includes intracerebroventricularly, e.g., to the lateral ventricle, administering to an immunocompetent mammal a composition comprising an effective amount of a rAAV vector comprising an open reading frame encoding a gene product, the expression of which in the central nervous system of the mammal prevents, inhibits or treats the one or more symptoms. In one embodiment, the gene product is a lysosomal storage enzyme. In one embodiment, the rAAV vector is an AAV-1, AAV-2, AAV-3, AAV-4, AAV-5, AAV-6, AAV-7, AAV rh10, or AAV-9 vector. In one embodiment, the rAAV vector is not a rAAV-5 vector. In one embodiment, the mammal is a human. In one embodiment, multiple doses are administered. In one embodiment, the composition is administered weekly, monthly or two or more months apart. In one embodiment, the mammal that is intracerebroventricularly administered the AAV is not subjected to immunotolerization or immune suppression (e.g., administration of the AAV alone provides for the therapeutic effect). In one embodiment, the mammal that is intracerebroventricularly administered the AAV is immunodeficient or is subjected to immunotolerization or immune suppression, e.g., to induce higher levels of therapeutic protein expression relative to a corresponding mammal that is intracerebroventricularly administered the AAV but not subjected to immunotolerization or immune suppression In one embodiment, the mammal is immunotolerized to the gene product before the composition comprising the AAV is administered.

Further provided is a method to prevent, inhibit or treat one or more symptoms associated with a disease or disorder of the central nervous system in a mammal in need thereof. The method includes endovascularly administering to the mammal a composition comprising an effective amount of a rAAV vector comprising an open reading frame encoding a gene product, the expression of which in the central nervous system of the mammal prevents, inhibits or treats the one or more symptoms, and an effective amount of a permeation enhancer. In one embodiment, the composition comprises the permeation enhancer. In one embodiment, the permeation enhancer comprises mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA. In one embodiment, the gene product is a lysosomal storage enzyme. In one embodiment, the mammal is an immunocompetent adult. In one embodiment, the rAAV vector is an AAV-1, AAV-2, AAV-3, AAV-4, AAV-5, AAV-6, AAV-7, AAV-8, MV rh10, or AAV-9 vector. In one embodiment, the rAAV vector is not a rAAV-5 vector. In one embodiment, the mammal is a human. In one embodiment, multiple doses are administered. In one embodiment, the composition is administered weekly. In one embodiment, the composition is administered weekly, monthly or two or more months apart. In one embodiment, the mammal that is endovascularly administered the AAV is not subjected to immunotolerization or immune suppression (e.g., administration of the MV provides for the therapeutic effect). In one embodiment, the mammal that is endovascularly administered the AAV is immunodeficient or is subjected to immunotolerization or immune suppression, e.g., to induce higher levels of therapeutic protein expression relative to a corresponding mammal that is endovascularly administered the AAV but not subjected to immunotolerization or immune suppression.

In one embodiment, the method includes intranasally administering to a mammal a composition comprising an effective amount of a rAAV-9 vector comprising an open reading frame encoding a gene product, the expression of which in the central nervous system of the mammal prevents, inhibits or treats the one or more symptoms, and optionally administering a permeation enhancer. In one embodiment, intranasal delivery may be accomplished as described in U.S. Pat. No. 8,609,088, the disclosure of which is incorporated by reference herein. In one embodiment, the permeation enhancer is administered before the composition. In one embodiment, the composition comprises a permeation enhancer. In one embodiment, the permeation enhancer is administered after the composition. In one embodiment, the gene product is a lysosomal storage enzyme. In one embodiment, the mammal is an immunocompetent adult. In one embodiment, the mammal is a human. In one embodiment, multiple doses are administered. In one embodiment, the composition is administered weekly, monthly or two or more months apart. In one embodiment, the mammal that is intranasally administered the AAV is not subjected to immunotolerization or immune suppression. In one embodiment, the mammal that is intranasally administered the AAV is subjected to immunotolerization or immune suppression, e.g., to induce higher levels of IDUA protein expression relative to a corresponding mammal that is intranasally administered the AAV but not subjected to immunotolerization or immune suppression.

Also provided is a method to prevent, inhibit or treat one or more symptoms associated with a disease of the central nervous system in a mammal in need thereof. The method includes administering to the mammal a composition comprising an effective amount of a rAAV vector comprising an open reading frame encoding a gene product, the expression of which in the central nervous system of the mammal prevents, inhibits or treats the one or more symptoms, and an immune suppressant. In one embodiment, the immune suppressant comprises cyclophosphamide. In one embodiment, the immune suppressant comprises a glucocorticoid, cytostatic agents including an alkylating agent or an anti-metabolite such as methotrexate, azathioprine, mercaptopurine or a cytotoxic antibiotic, an antibody, or an agent active on immunophilin. In one embodiment, the immune suppressant comprises a nitrogen mustard, nitrosourea, a platinum compound, methotrexate, azathioprine, mercaptopurine, fluorouracil, dactinomycin, an anthracyclin, mitomycin C, bleomycin, mithramycin, IL2-receptor-(CD25-) or CD3-directed antibodies, anti-IL-2 antibodies, cyclosporin, tacrolimus, sirolimus, IFN-β, IFN-γ, an opioid, or TNF-α (tumor necrosis factor-alpha) binding agents such as infliximab (Remicade), etanercept (Enbrel), or adalimumab (Humira). In one embodiment, the rAAV and the immune suppressant are co-administered. In one embodiment, the rAAV is administered before and optionally after the immune suppressant. In one embodiment, the immune suppressant is administered before the rAAV. In one embodiment, the rAAV and the immune suppressant are intrathecally administered. In one embodiment, the rAAV and the immune suppressant are intracerebroventricularly administered. In one embodiment, the rAAV is intrathecally administered and the immune suppressant is intravenously administered. In one embodiment, the gene product is a lysosomal storage enzyme. In one embodiment, the mammal is an adult. In one embodiment, the rAAV vector is an AAV-1, AAV-2, AAV-3, AAV-4, AAV-5, AAV-6, AAV-7, AAV-8, AAV rh10, or AAV-9 vector. In one embodiment, the mammal is a human. In one embodiment, multiple doses are administered. In one embodiment, the composition is administered weekly. In one embodiment, the composition is administered weekly, monthly or two or more months apart.

The invention also provides a method to prevent, inhibit or treat one or more symptoms associated with a disease of the central nervous system in a mammal in need thereof. A mammal immunotolerized to a gene product that is associated with the disease is administered a composition comprising an effective amount of a rAAV vector comprising an open reading frame encoding a gene product, the expression of which in the central nervous system of the mammal prevents, inhibits or treats the one or more symptoms. In one embodiment, the gene product is a lysosomal storage enzyme. In one embodiment, the mammal is an adult. In one embodiment, the rAAV vector is an AAV-1, AAV-2, AAV-3, AAV-4, AAV-5, AAV-6, AAV-7, AAV-8, MV rh10, or AAV-9 vector. In one embodiment, the mammal is a human. In one embodiment, multiple doses are administered. In one embodiment, the composition is administered weekly.

Gene products that may be encoded by rAAV vectors include, but are not limited to, alpha-L-iduronidase, iduronate-2-sulfatase, heparan sulfate sulfatase, N-acetyl-alpha-D-glucosaminidase, beta-hexosaminidase, alpha-galactosidase, betagalactosidase, beta-glucuronidase, glucocerebrosidase, fibroblast growth factor-2 (FGF-2), brain derived growth factor (BDGF), neurturin, glial derived growth factor (GDGF), tyrosine hydroxylase, dopamine decarboxylase, or glutamic acid decarboxylase.

Diseases that have one or more neurologic symptoms that may be prevented, inhibited or treated using the methods disclosed herein include, but are not limited to, Adrenoleukodystrophy, Alzheimer disease, Amyotrophic lateral sclerosis, Angelman syndrome, Ataxia telangiectasia, Charcot-Marie-Tooth syndrome, Cockayne syndrome, Deafness, Duchenne muscular dystrophy, Epilepsy, Essential tremor, Fragile X syndrome, Friedreich's ataxia, Gaucher disease, Huntington disease, Lesch-Nyhan syndrome, Maple syrup urine disease, Menkes syndrome, Myotonic dystrophy, Narcolepsy, Neurofibromatosis, Niemann-Pick disease, Parkinson disease, Phenylketonuria, Prader-Willi syndrome, Refsum disease, Rett syndrome, Spinal muscular atrophy, Spinocerebellar ataxia, Tangier disease, Tay-Sachs disease, Tuberous sclerosis, Von Hippel-Lindau syndrome, Williams syndrome, Wilson's disease, or Zellweger syndrome. In one embodiment, the disease is a lysosomal storage disease, e.g., a lack or deficiency in a lysosomal storage enzyme. Lysosomal storage diseases include, but are not limited to, mucopolysaccharidosis (MPS) diseases, for instance, mucopolysaccharidosis type I, e.g., Hurler syndrome and the variants Scheie syndrome and Hurler-Scheie syndrome (a deficiency in alpha-L-iduronidase); Hunter syndrome (a deficiency of iduronate-2-sulfatase); mucopolysaccharidosis type III, e.g., Sanfilippo syndrome (A, B, C or D; a deficiency of heparan sulfate sulfatase, N-acetyl-alpha-D-glucosaminidase, acetyl CoA:alpha-glucosaminide N-acetyl transferase or N-acetylglucosamine-6-sulfate sulfatase); mucopolysaccharidosis type IV e.g., mucopolysaccharidosis type IV, e.g., Morquio syndrome (a deficiency of galactosamine-6-sulfate sulfatase or beta-galactosidase); mucopolysaccharidosis type VI, e.g., Maroteaux-Lamy syndrome (a deficiency of arylsulfatase B); mucopolysaccharidosis type II; mucopolysaccharidosis type III (A, B, C or D; a deficiency of heparan sulfate sulfatase, N-acetyl-alpha-D-glucosaminidase, acetyl CoA:alpha-glucosaminide N-acetyl transferase or N-acetylglucosamine-6-sulfate sulfatase); mucopolysaccharidosis type IV (A or B; a deficiency of galactosamine-6-sulfatase and beta-galatacosidase); mucopolysaccharidosis type VI (a deficiency of arylsulfatase B); mucopolysaccharidosis type VII (a deficiency in beta-glucuronidase); mucopolysaccharidosis type VIII (a deficiency of glucosamine-6-sulfate sulfatase); mucopolysaccharidosis type IX (a deficiency of hyaluronidase); Tay-Sachs disease (a deficiency in alpha subunit of beta-hexosaminidase); Sandhoff disease (a deficiency in both alpha and beta subunit of beta-hexosaminidase); GM1 gangliosidosis (type I or type II); Fabry disease (a deficiency in alpha galactosidase); metachromatic leukodystrophy (a deficiency of aryl sulfatase A); Pompe disease (a deficiency of acid maltase); fucosidosis (a deficiency of fucosidase); alpha-mannosidosis (a deficiency of alpha-mannosidase); beta-mannosidosis (a deficiency of beta-mannosidase), ceroid lipofuscinosis, and Gaucher disease (types I, II and III; a deficiency in glucocerebrosidase), as well as disorders such as Hermansky-Pudlak syndrome; Amaurotic idiocy; Tangier disease; aspartylglucosaminuria; congenital disorder of glycosylation, type Ia; Chediak-Higashi syndrome; macular dystrophy, corneal, 1; cystinosis, nephropathic; Fanconi-Bickel syndrome; Farber lipogranulomatosis; fibromatosis; geleophysic dysplasia; glycogen storage disease I; glycogen storage disease Ib; glycogen storage disease Ic; glycogen storage disease III; glycogen storage disease IV; glycogen storage disease V; glycogen storage disease VI; glycogen storage disease VII; glycogen storage disease 0; immunoosseous dysplasia, Schimke type; lipidosis; lipase b; mucolipidosis II; mucolipidosis II, including the variant form; mucolipidosis IV; neuraminidase deficiency with beta-galactosidase deficiency; mucolipidosis I; Niemann-Pick disease (a deficiency of sphingomyelinase); Niemann-Pick disease without sphingomyelinase deficiency (a deficiency of a npc1 gene encoding a cholesterol metabolizing enzyme); Refsum disease; Sea-blue histiocyte disease; infantile sialic acid storage disorder; sialuria; multiple sulfatase deficiency; triglyceride storage disease with impaired long-chain fatty acid oxidation; Winchester disease; Wolman disease (a deficiency of cholesterol ester hydrolase); Deoxyribonuclease I-like 1 disorder; arylsulfatase E disorder; ATPase, H+ transporting, lysosomal, subunit 1 disorder; glycogen storage disease IIb; Ras-associated protein rab9 disorder; chondrodysplasia punctata 1, X-linked recessive disorder; glycogen storage disease VIII; lysosome-associated membrane protein 2 disorder; Menkes syndrome; congenital disorder of glycosylation, type Ic; and sialuria. Replacement of less than 20%, e.g., less than 10% or about 1% to 5% levels of lysosomal storage enzyme found in nondiseased mammals, may prevent, inhibit or treat neurological symptoms such as neurological degeneration in mammals.

In one embodiment, the methods described herein involve delivering to the CNS of an immunocompetent human in need of treatment a composition comprising an effective amount of a rAAV-9 vector comprising an open reading frame encoding a IDUA. Routes of administration to the CNS/brain include, but are not limited to intrathecal administration, intracranial administration, e.g., intracerebroventricular administration or lateral cerebro ventricular administration, intranasal administration, endovascular administration, and intraparenchymal administration.

Other viral vectors may be employed in the methods of the invention, e.g., viral vectors such as retrovirus, lentivirus, adenovirus, semliki forest virus or herpes simplex virus vectors.

BRIEF DESCRIPTION OF THE FIGURES

FIG. 1. Experimental design for iduronidase-deficient adult mice administered IDUA-AAV either intracerebroventricularly (ICV) (right lateral ventricle) or intrathecally (lumbar area) To prevent immune response, animals were either immunosuppressed with cyclophosphamide (CP), immunotolerized at birth by intravenous administration of human iduonidase protein (aldurazyme), or the injections (10 microliters, $3\times10^{11}$ particles) were carried out in NOD-SCID immunodeficient mice that were also iduronidase deficient. Animals were sacrificed at the indicated time post-treatment, the brains were microdissected and extracts assayed for iduronidase activity.

FIGS. 7A-E. Data are grouped according the area of the brain. A) hippocampus. B) cerebellum, C) cortex. D) striatum, and E) rest of brain.

FIG. 9. Schematic of experimental design. All mice were adult MPSI (IDUA deficient mice injected with 10 microliters ($3\times10^{11}$ particles) of AAV.

Figure 19B:
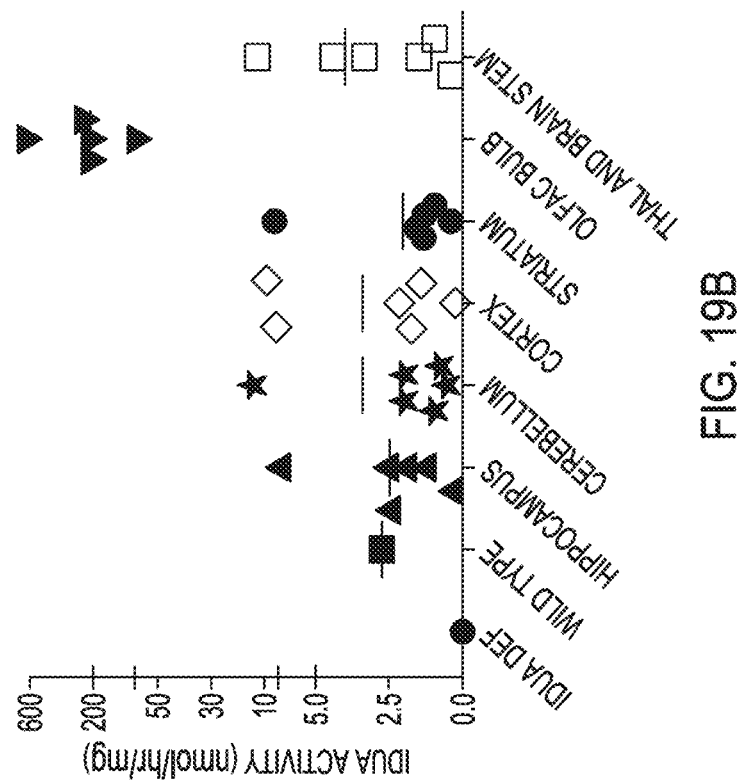
FIGS. 19A-B. Intranasal administration of AAV9/IDUA in immunocompetent, IDUA deficient animals. Adult MPS I mice were infused with AAV9/IDUA intranasally, followed by a weekly immunosuppressive regimen of cyclophosphamide. Animals were sacrificed at 12 weeks post-injection and brains were analyzed for IDUA enzyme activity.
Figure 19A:
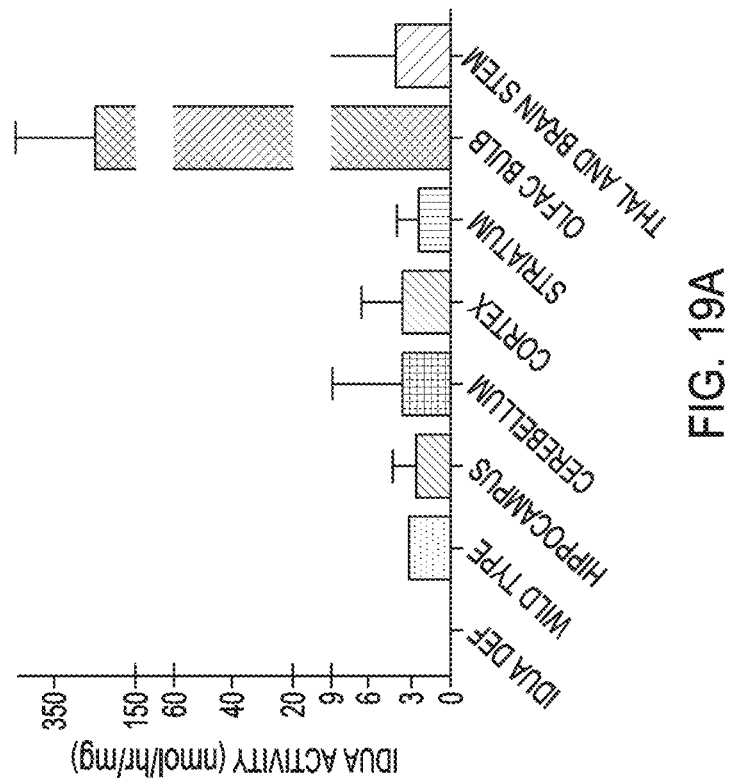
Figure 20:
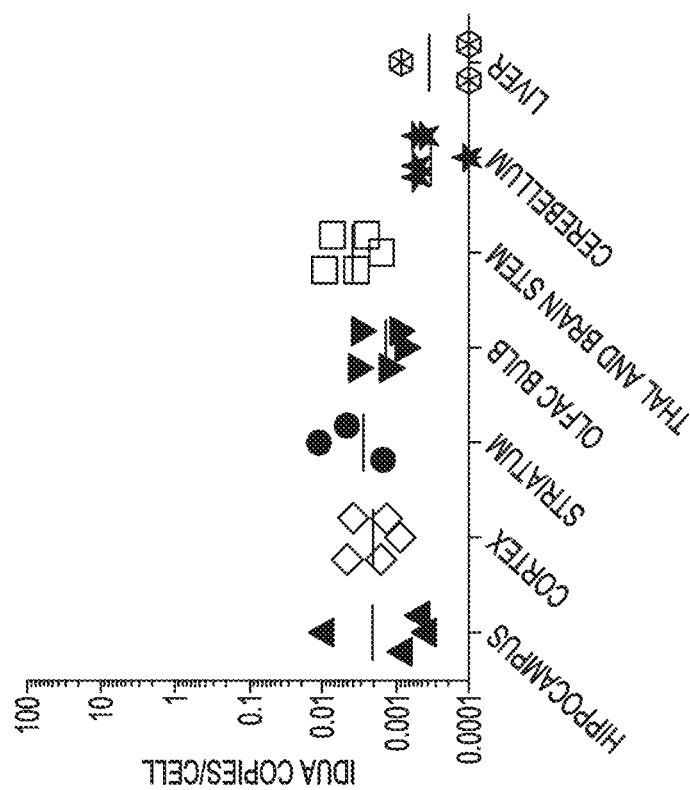
FIG. 20. IDUA vector copies in brain. Microdissected brains were analyzed for IDUA vector sequences by QPCR.

The copy numbers in intranasally injected mice correlate to the levels of enzyme in FIG. 19.

DETAILED DESCRIPTION OF THE INVENTION

Definitions

As used herein, "individual" (as in the subject of the treatment) means a mammal. Mammals include, for example, humans; non-human primates, e.g., apes and monkeys; and non-primates, e.g., dogs, cats, rats, mice, cattle, horses, sheep, and goats. Non-mammals include, for example, fish and birds.

The term "disease" or "disorder" are used interchangeably, and are used to refer to diseases or conditions wherein lack of or reduced amounts of a specific gene product, e.g., a lysosomal storage enzyme, plays a role in the disease such that a therapeutically beneficial effect can be achieved by supplementing, e.g., to at least 1% of normal levels.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, "inhibiting" means inhibition of further progression or worsening of the symptoms associated with the disorder or disease, and "preventing" refers to prevention of the symptoms associated with the disorder or disease.

As used herein, an "effective amount" or a "therapeutically effective amount" of an agent of the invention e.g., a recombinant AAV encoding a gene product, refers to an amount of the agent that alleviates, in whole or in part, symptoms associated with the disorder or condition, or halts or slows further progression or worsening of those symptoms, or prevents or provides prophylaxis for the disorder or condition, e.g., an amount that is effective to prevent, inhibit or treat in the individual one or more neurological symptoms.

In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

A "vector" as used herein refers to a macromolecule or association of macromolecules that comprises or associates with a polynucleotide and which can be used to mediate delivery of the polynucleotide to a cell, either in vitro or in vivo. Illustrative vectors include, for example, plasmids, viral vectors, liposomes and other gene delivery vehicles. The polynucleotide to be delivered, sometimes referred to as a "target polynucleotide" or "transgene," may comprise a coding sequence of interest in gene therapy (such as a gene encoding a protein of therapeutic interest) and/or a selectable or detectable marker.

"AAV" is adeno-associated virus, and may be used to refer to the virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on its binding properties, e.g., there are eleven serotypes of AAVs, AAV-1-AAV-11, including AAV-2, AAV-5, AAV-8, AAV-9 and AAV rh10, and the term encompasses pseudotypes with the same binding properties. Thus, for example, AAV-5 serotypes include AAV with the binding properties of AAV-5, e.g., a pseudotyped AAV comprising AAV-5 capsid and a rAAV genome which is not derived or obtained from AAV-5 or which genome is chimeric. The abbreviation "rAAV" refers to recombinant adeno-associated virus, also referred to as a recombinant AAV vector (or "rAAV vector").

An "AAV virus" refers to a viral particle composed of at least one AAV capsid protein and an encapsidated polynucleotide. If the particle comprises a heterologous polynucleotide (i.e., a polynucleotide other than a wild-type AAV genome such as a transgene to be delivered to a mammalian cell), it is typically referred to as "rAAV". An MV "capsid protein" includes a capsid protein of a wild-type AAV, as well as modified forms of an AAV capsid protein which are structurally and or functionally capable of packaging a rAAV genome and bind to at least one specific cellular receptor which may be different than a receptor employed by wild type AAV. A modified AAV capsid protein includes a chimeric AAV capsid protein such as one having amino acid sequences from two or more serotypes of AAV, e.g., a capsid protein formed from a portion of the capsid protein from AAV-5 fused or linked to a portion of the capsid protein from MV-2, and a AAV capsid protein having a tag or other detectable non-AAV capsid peptide or protein fused or linked to the AAV capsid protein, e.g., a portion of an antibody molecule which binds the transferrin receptor may be recombinantly fused to the AAV-2 capsid protein.

A "pseudotyped" rAAV is an infectious virus having any combination of an AAV capsid protein and an AAV genome. Capsid proteins from any AAV serotype may be employed with a rAAV genome which is derived or obtainable from a wild-type AAV genome of a different serotype or which is a chimeric genome, i.e., formed from AAV DNA from two or more different serotypes, e.g., a chimeric genome having 2 inverted terminal repeats (ITRs), each ITR from a different serotype or chimeric ITRs. The use of chimeric genomes such as those comprising ITRs from two AAV serotypes or chimeric ITRs can result in directional recombination which may further enhance the production of transcriptionally active intermolecular concatamers. Thus, the 5' and 3' ITRs within a rAAV vector of the invention may be homologous, i.e., from the same serotype, heterologous, i.e., from different serotypes, or chimeric, i.e., an ITR which has ITR sequences from more than one AAV serotype.

rAAV Vectors

Adeno-associated viruses of any serotype are suitable to prepare rAAV, since the various serotypes are functionally and structurally related, even at the genetic level. All AAV serotypes apparently exhibit similar replication properties mediated by homologous rep genes; and all generally bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to ITRs. The similar infectivity patterns also suggest that the replication functions in each serotype are under similar regulatory control. Among the various AAV serotypes, AAV2 is most commonly employed.

An AAV vector of the invention typically comprises a polynucleotide that is heterologous to AAV. The polynucleotide is typically of interest because of a capacity to provide a function to a target cell in the context of gene therapy, such as up- or down-regulation of the expression of a certain phenotype. Such a heterologous polynucleotide or "transgene," generally is of sufficient length to provide the desired function or encoding sequence.

Where transcription of the heterologous polynucleotide is desired in the intended target cell, it can be operably linked to its own or to a heterologous promoter, depending for example on the desired level and/or specificity of transcription within the target cell, as is known in the art. Various types of promoters and enhancers are suitable for use in this context. Constitutive promoters provide an ongoing level of gene transcription, and may be preferred when it is desired that the therapeutic or prophylactic polynucleotide be expressed on an ongoing basis. Inducible promoters generally exhibit low activity in the absence of the inducer, and are up-regulated in the presence of the inducer. They may be preferred when expression is desired only at certain times or at certain locations, or when it is desirable to titrate the level of expression using an inducing agent. Promoters and enhancers may also be tissue-specific: that is, they exhibit their activity only in certain cell types, presumably due to gene regulatory elements found uniquely in those cells.

Illustrative examples of promoters are the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. Inducible promoters include heavy metal ion inducible promoters (such as the mouse mammary tumor virus (mMTV) promoter or various growth hormone promoters), and the promoters from T7 phage which are active in the presence of T7 RNA polymerase. By way of illustration, examples of tissue-specific promoters include various surfactin promoters (for expression in the lung), myosin promoters (for expression in muscle), and albumin promoters (for expression in the liver). A large variety of other promoters are known and generally available in the art, and the sequences of many such promoters are available in sequence databases such as the GenBank database.

Where translation is also desired in the intended target cell, the heterologous polynucleotide will preferably also comprise control elements that facilitate translation (such as a ribosome binding site or "RBS" and a polyadenylation signal). Accordingly, the heterologous polynucleotide generally comprises at least one coding region operatively linked to a suitable promoter, and may also comprise, for example, an operatively linked enhancer, ribosome binding site and poly-A signal. The heterologous polynucleotide may comprise one encoding region, or more than one encoding regions under the control of the same or different promoters. The entire unit, containing a combination of control elements and encoding region, is often referred to as an expression cassette.

The heterologous polynucleotide is integrated by recombinant techniques into or in place of the AAV genomic coding region (i.e., in place of the AAV rep and cap genes), but is generally flanked on either side by AAV inverted terminal repeat (ITR) regions. This means that an ITR appears both upstream and downstream from the coding sequence, either in direct juxtaposition, e.g., (although not necessarily) without any intervening sequence of AAV origin in order to reduce the likelihood of recombination that might regenerate a replication-competent AAV genome. However, a single ITR may be sufficient to carry out the functions normally associated with configurations comprising two ITRs (see, for example, WO 94/13788), and vector constructs with only one ITR can thus be employed in conjunction with the packaging and production methods of the present invention.

The native promoters for rep are self-regulating, and can limit the amount of AAV particles produced. The rep gene can also be operably linked to a heterologous promoter, whether rep is provided as part of the vector construct, or separately. Any heterologous promoter that is not strongly down-regulated by rep gene expression is suitable; but inducible promoters may be preferred because constitutive expression of the rep gene can have a negative impact on the host cell. A large variety of inducible promoters are known in the art; including, by way of illustration, heavy metal ion inducible promoters (such as metallothionein promoters); steroid hormone inducible promoters (such as the MMTV promoter or growth hormone promoters); and promoters such as those from T7 phage which are active in the presence of T7 RNA polymerase. One sub-class of inducible promoters are those that are induced by the helper virus that is used to complement the replication and packaging of the rAAV vector. A number of helper-virus-inducible promoters have also been described, including the adenovirus early gene promoter which is inducible by adenovirus E1A protein; the adenovirus major late promoter; the herpesvirus promoter which is inducible by herpesvirus proteins such as VP16 or 1CP4; as well as vaccinia or poxvirus inducible promoters.

Methods for identifying and testing helper-virus-inducible promoters have been described (see, e.g., WO 96/17947). Thus, methods are known in the art to determine whether or not candidate promoters are helper-virus-inducible, and whether or not they will be useful in the generation of high efficiency packaging cells. Briefly, one such method involves replacing the p5 promoter of the MV rep gene with the putative helper-virus-inducible promoter (either known in the art or identified using well-known techniques such as linkage to promoter-less "reporter" genes). The AAV rep-cap genes (with p5 replaced), e.g., linked to a positive selectable marker such as an antibiotic resistance gene, are then stably integrated into a suitable host cell (such as the HeLa or A549 cells exemplified below). Cells that are able to grow relatively well under selection conditions (e.g., in the presence of the antibiotic) are then tested for their ability to express the rep and cap genes upon addition of a helper virus. As an initial test for rep and/or cap expression, cells can be readily screened using immunofluorescence to detect Rep and/or Cap proteins. Confirmation of packaging capabilities and efficiencies can then be determined by functional tests for replication and packaging of incoming rAAV vectors. Using this methodology, a helper-virus-inducible promoter derived from the mouse metallothionein gene has been identified as a suitable replacement for the p5 promoter, and used for producing high titers of rAAV particles (as described in WO 96/17947).

Removal of one or more AAV genes is in any case desirable, to reduce the likelihood of generating replication-competent AAV ("RCA"). Accordingly, encoding or promoter sequences for rep, cap, or both, may be removed, since the functions provided by these genes can be provided in trans.

The resultant vector is referred to as being "defective" in these functions. In order to replicate and package the vector, the missing functions are complemented with a packaging gene, or a plurality thereof, which together encode the necessary functions for the various missing rep and/or cap gene products. The packaging genes or gene cassettes are in one embodiment not flanked by AAV ITRs and in one embodiment do not share any substantial homology with the rAAV genome. Thus, in order to minimize homologous recombination during replication between the vector sequence and separately provided packaging genes, it is desirable to avoid overlap of the two polynucleotide sequences. The level of homology and corresponding frequency of recombination increase with increasing length of homologous sequences and with their level of shared identity. The level of homology that will pose a concern in a given system can be determined theoretically and confirmed experimentally, as is known in the art. Typically, however, recombination can be substantially reduced or eliminated if the overlapping sequence is less than about a 25 nucleotide sequence if it is at least 80% identical over its entire length, or less than about a 50 nucleotide sequence if it is at least 70% identical over its entire length. Of course, even lower levels of homology are preferable since they will further reduce the likelihood of recombination. It appears that, even without any overlapping homology, there is some residual frequency of generating RCA. Even further reductions in the frequency of generating RCA (e.g., by nonhomologous recombination) can be obtained by "splitting" the replication and encapsidation functions of AAV, as described by Allen et al., WO 98/27204).

The rAAV vector construct, and the complementary packaging gene constructs can be implemented in this invention in a number of different forms. Viral particles, plasmids, and stably transformed host cells can all be used to introduce such constructs into the packaging cell, either transiently or stably.

In certain embodiments of this invention, the AAV vector and complementary packaging gene(s), if any, are provided in the form of bacterial plasmids, AAV particles, or any combination thereof. In other embodiments, either the AAV vector sequence, the packaging gene(s), or both, are provided in the form of genetically altered (preferably inheritably altered) eukaryotic cells. The development of host cells inheritably altered to express the AAV vector sequence, AAV packaging genes, or both, provides an established source of the material that is expressed at a reliable level.

A variety of different genetically altered cells can thus be used in the context of this invention. By way of illustration, a mammalian host cell may be used with at least one intact copy of a stably integrated rAAV vector. An AAV packaging plasmid comprising at least an AAV rep gene operably linked to a promoter can be used to supply replication functions (as described in U.S. Pat. No. 5,658,776). Alternatively, a stable mammalian cell line with an AAV rep gene operably linked to a promoter can be used to supply replication functions (see, e.g., Trempe et al., WO 95/13392); Burstein et al. (WO 98/23018); and Johnson et al. (U.S. Pat. No. 5,656,785). The AAV cap gene, providing the encapsidation proteins as described above, can be provided together with an AAV rep gene or separately (see, e.g., the above-referenced applications and patents as well as Allen et al. (WO 98/27204). Other combinations are possible and included within the scope of this invention.

Pathways for Delivery

Despite the immense network of the cerebral vasculature, systemic delivery of therapeutics to the central nervous system (CNS) is not effective for greater than 98% of small molecules and for nearly 100% of large molecules (Partridge, 2005). The lack of effectiveness is due to the presence of the blood-brain barrier (BBB), which prevents most foreign substances, even many beneficial therapeutics, from entering the brain from the circulating blood. While certain small molecule, peptide, and protein therapeutics given systemically reach the brain parenchyma by crossing the BBB (Banks, 2008), generally high systemic doses are needed to achieve therapeutic levels, which can lead to adverse effects in the body. Therapeutics can be introduced directly into the CNS by intracerebroventricular or intraparenchymal injections. Intranasal delivery bypasses the BBB and targets therapeutics directly to the CNS utilizing pathways along olfactory and trigeminal nerves innervating the nasal passages (Frey I I, 2002; Thorne et al., 2004; Dhanda et al., 2005).

Any route of rAAV administration may be employed so long as that route and the amount administered are prophylactically or therapeutically useful. In one example, routes of administration to the CNS include intrathecal and intracranial. Intracranial administration may be to the cisterna magna or ventricle. The term "cisterna magna" is intended to include access to the space around and below the cerebellum via the opening between the skull and the top of the spine. The term "cerebral ventricle" is intended to include the cavities in the brain that are continuous with the central canal of the spinal cord. Intracranial administration is via injection or infusion and suitable dose ranges for intracranial administration are generally about $10^3$ to $10^{15}$ infectious units of viral vector per microliter delivered in 1 to 3000 microliters of single injection volume. For instance, viral genomes or infectious units of vector per micro liter would generally contain about $10^4$, $10^5$, $10^6$, $10^7$, $10^8$, $10^9$, $10^{10}$, $10^{11}$, $10^{12}$, $10^{13}$, or $10^{14}$ viral genomes or infectious units of viral vector delivered in about 10, 50, 100, 200, 500, 1000, or 2000 microliters. It should be understood that the aforementioned dosage is merely an exemplary dosage and those of skill in the art will understand that this dosage may be varied. Effective doses may be extrapolated from dose-responsive curves derived from in vitro or in vivo test systems.

The AAV delivered in the intrathecal methods of treatment of the present invention may be administered through any convenient route commonly used for intrathecal administration. For example, the intrathecal administration may be via a slow infusion of the formulation for about an hour. Intrathecal administration is via injection or infusion and suitable dose ranges for intrathecal administration are generally about $10^3$ to $10^{15}$ infectious units of viral vector per microliter delivered in, for example, 1 to 3000 microliters or 0.5 to 15 milliliters of single injection volume. For instance, viral genomes or infectious units of vector per microliter would generally contain about $10^4$, $10^5$, $10^6$, $10^7$, $10^8$, $10^9$, $10^{10}$, $10^{11}$, $10^{12}$, $10^{13}$, or $10^{14}$ viral genomes or infectious units of viral vector.

The therapy, if a lysosomal storage enzyme such as IDUA is expressed, results in the normalization of lysosomal storage granules in the neuronal and/or meningeal tissue of the subjects as discussed above. It is contemplated that the deposition of storage granules is ameliorated from neuronal and glial tissue, thereby alleviating the developmental delay and regression seen in individuals suffering with lysosomal storage disease. Other effects of the therapy may include the normalization of lysosomal storage granules in the cerebral meninges near the arachnoid granulation, the presence of which in lysosomal storage disease result in high pressure hydrocephalus. The methods of the invention also may be used in treating spinal cord compression that results from the presence of lysosomal storage granules in the cervical meninges near the cord at C1-05 or elsewhere in the spinal cord. The methods of the invention also are directed to the treatment of cysts that are caused by the perivascular storage of lysosomal storage granules around the vessels of the brain. In other embodiments, the therapy also may advantageously result in normalization of liver volume and urinary glycosaminoglycan excretion, reduction in spleen size and apnea/hypopnea events, increase in height and growth velocity in prepubertal subjects, increase in shoulder flexion and elbow and knee extension, and reduction in tricuspid regurgitation or pulmonic regurgitation.

The intrathecal administration of the present invention may comprise introducing the composition into the lumbar area. Any such administration may be via a bolus injection. Depending on the severity of the symptoms and the responsiveness of the subject to the therapy, the bolus injection may be administered once per week, once per month, once every 6 months or annually. In other embodiments, the intrathecal administration is achieved by use of an infusion pump. Those of skill in the art are aware of devices that may be used to effect intrathecal administration of a composition. The composition may be intrathecally given, for example, by a single injection, or continuous infusion. It should be understood that the dosage treatment may be in the form of a single dose administration or multiple doses.

As used herein, the term "intrathecal administration" is intended to include delivering a pharmaceutical composition directly into the cerebrospinal fluid of a subject, by techniques including lateral cerebroventricular injection through a burrhole or cisternal or lumbar puncture or the like. The term "lumbar region" is intended to include the area between the third and fourth lumbar (lower back) vertebrae and, more inclusively, the L2-S1 region of the spine.

Administration of a composition in accordance with the present invention to any of the above mentioned sites can be achieved by direct injection of the composition or by the use of infusion pumps. For injection, the composition can be formulated in liquid solutions, e.g., y in physiologically compatible buffers such as Hank's solution, Ringer's solution or phosphate buffer. In addition, the enzyme may be formulated in solid form and re-dissolved or suspended immediately prior to use. Lyophilized forms are also included. The injection can be, for example, in the form of a bolus injection or continuous infusion (e.g., using infusion pumps) of the enzyme.

In one embodiment of the invention, the rAAV is administered by lateral cerebro-ventricular injection into the brain of a subject. The injection can be made, for example, through a burr hole made in the subject's skull. In another embodiment, the enzyme and/or other pharmaceutical formulation is administered through a surgically inserted shunt into the cerebral ventricle of a subject. For example, the injection can be made into the lateral ventricles, which are larger, even though injection into the third and fourth smaller ventricles can also be made. In yet another embodiment, the compositions used in the present invention are administered by injection into the cisterna magna or lumbar area of a subject.

While the exact mechanisms underlying intranasal drug delivery to the CNS are not entirely understood, an accumulating body of evidence demonstrates that pathways involving nerves connecting the nasal passages to the brain and spinal cord are important. In addition, pathways involving the vasculature, cerebrospinal fluid, and lymphatic system have been implicated in the transport of molecules from the nasal cavity to the CNS. It is likely that a combination of these pathways is responsible, although one pathway may predominate, depending on the properties of the therapeutic, the characteristics of the formulation, and the delivery device used.

Therapeutics can rapidly gain access to the CNS following intranasal administration along olfactory nerve pathways leading from the nasal cavity directly to the CNS. Olfactory nerve pathways are a major component of intranasal delivery, evidenced by the fact that fluorescent tracers are associated with olfactory nerves as they traverse the cribriform plate (Jansson et al., 2002), drug concentrations in the olfactory bulbs are generally among the highest CNS concentrations observed (Thorne et al., 2004; Banks et al., 2004; Graff et al., 2005a); Nonaka et al., 2008; Ross et al., 2004; Ross et al., 2008; Thorne et al., 2008), and a strong, positive correlation exists between concentrations in the olfactory epithelium and olfactory bulbs (Dhuria et al., 2009a).

Olfactory pathways arise in the upper portion of the nasal passages, in the olfactory region, where olfactory receptor neurons (ORNs) are interspersed among supporting cells (sustentacular cells), microvillar cells, and basal cells. ORNs mediate the sense of smell by conveying sensory information from the peripheral environment to the CNS (Clerico et al., 2003). Beneath the epithelium, the lamina propria contains mucus secreting Bowman's glands, axons, blood vessels, lymphatic vessels, and connective tissue. The dendrites of ORNs extend into the mucous layer of the olfactory epithelium, while axons of these bipolar neurons extend centrally through the lamina propria and through perforations in the cribriform plate of the ethmoid bone, which separates the nasal and cranial cavities. The axons of ORNs pass through the subarachnoid space containing CSF and terminate on mitral cells in the olfactory bulbs. From there, neural projections extend to multiple brain regions including the olfactory tract, anterior olfactory nucleus, piriform cortex, amygdala, and hypothalamus (Buck, 2000). In addition to ORNs, chemosensory neurons located at the anterior tip of the nasal cavity in the Grueneberg ganglion lead into the olfactory bulbs (Fuss et al., 2005; Koos et al., 2005).

The unique characteristics of the ORNs contribute to a dynamic cellular environment critical for intranasal delivery to the CNS. Due to the direct contact with toxins in the external environment, ORNs regenerate every 3-4 weeks from basal cells residing in the olfactory epithelium (Mackay-Sim, 2003). Special Schwann cell-like cells called olfactory ensheathing cells (OECs) envelope the axons of ORNs and have an important role in axonal regeneration, regrowth, and remyelination (Field et al., 2003; Li et al., 2005a; Li et al., 2005b). The OECs create continuous, fluid-filled perineurial channels that, interestingly, remain open, despite the degeneration and regeneration of ORNs (Williams et al., 2004).

Given the unique environment of the olfactory epithelium, it is possible for intranasally administered therapeutics to reach the CNS via extracellular or intracellular mechanisms of transport along olfactory nerves. Extracellular transport mechanisms involve the rapid movement of molecules between cells in the nasal epithelium, requiring only several minutes to 30 minutes for a drug to reach the olfactory bulbs and other areas of the CNS after intranasal administration (Frey I I, 2002; Balin et al., 1986). Transport likely involves bulk flow mechanisms (Thorne et al., 2004; Thorne et al., 2001) within the channels created by the OECs. Drugs may also be propelled within these channels by the structural changes that occur during depolarization and axonal propagation of the action potential in adjacent axons (Luzzati et al., 2004). Intracellular transport mechanisms involve the uptake of molecules into ORNs by passive diffusion, receptor-mediated endocytosis or adsorptive endocytosis, followed by slower axonal transport, taking several hours to days for a drug to appear in the olfactory bulbs and other brain areas (Baker et al., 1986; Broadwell et al., 1985; Kristensson et al., 1971). Intracellular transport in ORNs has been demonstrated for small, lipophilic molecules such as gold particles (de Lorenzo, 1970; Gopinath et al., 1978), aluminum salts (Perl et al., 1987), and for substances with receptors on ORNs such as WGA-HRP (Thorne et al., 1995; Baker et al., 1986; Itaya et al., 1986; Shipley, 1985). Intracellular mechanisms, while important for certain therapeutics, are not likely to be the predominant mode of transport into the CNS. While some large molecules, such as galanin-like peptide (CALF), exhibit saturable transport pathways into the CNS (Nonaka et al., 2008), for other large molecules such as NGF and insulin-like growth factor-I (IGF-I), intranasal delivery into the brain is nonsaturable and not receptor mediated (Thorne et al., 2004; Chen et al., 1998; Zhao et al., 2004), An often overlooked but important pathway connecting the nasal passages to the CNS involves the trigeminal nerve, which innervates the respiratory and olfactory epithelium of the nasal passages and enters the CNS in the pons (Clerico et al., 2003; Graff et al., 2003). Interestingly, a small portion of the trigeminal nerve also terminates in the olfactory bulbs (Schaefer et al., 2002). The cellular composition of the respiratory region of the nasal passages is different from that of the olfactory region, with ciliated epithelial cells distributed among mucus secreting goblet cells. These cells contribute to mucociliary clearance mechanisms that remove mucus along with foreign substances from the nasal cavity to the nasopharynx. The trigeminal nerve conveys sensory information from the nasal cavity, the oral cavity, the eyelids, and the cornea, to the CNS via the ophthalmic division (V1), the maxillary division (V2), or the mandibular division (V3) of the trigeminal nerve (Clerico et al., 2003; Gray, 1978). Branches from the ophthalmic division of the trigeminal nerve provide innervation to the dorsal nasal mucosa and the anterior portion of the nose, while branches of the maxillary division provide innervation to the lateral walls of the nasal mucosa. The mandibular division of the trigeminal nerve extends to the lower jaw and teeth, with no direct neural inputs to the nasal cavity. The three branches of the trigeminal nerve come together at the trigeminal ganglion and extend centrally to enter the brain at the level of the pons, terminating in the spinal trigeminal nuclei in the brainstem. A unique feature of the trigeminal nerve is that it enters the brain from the respiratory epithelium of the nasal passages at two sites: (1) through the anterior lacerated foramen near the pons and (2) through the cribriform plate near the olfactory bulbs, creating entry points into both caudal and rostral brain areas following intranasal administration. It is also likely that other nerves that innervate the face and head, such as the facial nerve, or other sensory structures in the nasal cavity, such as the Grueneberg ganglion, may provide entry points for intranasally applied therapeutics into the CNS.

Traditionally, the intranasal route of administration has been utilized to deliver drugs to the systemic circulation via absorption into the capillary blood vessels underlying the nasal mucosa. The nasal mucosa is highly vascular, receiving its blood supply from branches of the maxillary, ophthalmic and facial arteries, which arise from the carotid artery (Clerico et al., 2003; Cauna, 1982). The olfactory mucosa receives blood from small branches of the ophthalmic artery, whereas the respiratory mucosa receives blood from a large caliber arterial branch of the maxillary artery (DeSesso, 1993). The relative density of blood vessels is greater in the respiratory mucosa compared to the olfactory mucosa, making the former region an ideal site for absorption into the blood (DeSesso, 1993). The vasculature in the respiratory region contains a mix of continuous and fenestrated endothelia (Grevers et al., 1987; Van Diest et al., 1979), allowing both small and large molecules to enter the systemic circulation following nasal administration.

Delivery to the CNS following absorption into the systemic circulation and subsequent transport across the BBB is possible, especially for small, lipophilic drugs, which more easily enter the blood stream and cross the BBB compared to large, hydrophilic therapeutics such as peptides and proteins.

Increasing evidence is emerging suggesting that mechanisms involving channels associated with blood vessels, or perivascular channels, are involved in intranasal drug delivery to the CNS. Perivascular spaces are bound by the outermost layer of blood vessels and the basement membrane of the surrounding tissue (Pollock et al., 1997). These perivascular spaces act as a lymphatic system for the brain, where neuron-derived substances are cleared from brain interstitial fluid by entering perivascular channels associated with cerebral blood vessels. Perivascular transport is due to bulk flow mechanisms, as opposed to diffusion alone (Cserr et al., 1981; Groothuis et al., 2007), and arterial pulsations are also a driving force for perivascular transport (Rennels et al., 1985; Rennels et al., 1985). Intranasally applied drugs can move into perivascular spaces in the nasal passages or after reaching the brain and the widespread distribution observed within the CNS could be due to perivascular transport mechanisms (Thorne et al., 2004).

Pathways connecting the subarachnoid space containing CSF, perineurial spaces encompassing olfactory nerves, and the nasal lymphatics are important for CSF drainage and these same pathways provide access for intranasally applied therapeutics to the CSF and other areas of the CNS. Several studies document that tracers injected into the CSF in the cerebral ventricles or subarachnoid space drain to the underside of the olfactory bulbs into channels associated with olfactory nerves traversing the cribriform plate and reach the nasal lymphatic system and cervical lymph nodes (Bradbury et al., 1983; Hatterer et al., 2006; Johnston et al., 2004a); Kida et al., 1993; Walter et al., 2006a; Walter et al., 2006b). Drugs can access the CNS via these same pathways after intranasal administration, moving from the nasal passages to the CSF to the brain interstitial spaces and perivascular spaces for distribution throughout the brain. These drainage pathways are significant in a number of animal species (sheep, rabbits, and rats) accounting for approximately 50% of CSF clearance (Bradbury et al., 1981; Boulton et al., 1999; Boulton et al., 1996; Cserr et al., 1992). Pathways between the nasal passages and the CSF are still important and functional in humans, evidenced by the fact that therapeutics are directly delivered to the CSF following intranasal delivery, without entering the blood to an appreciable extent (Born et al., 2002). A number of intranasal studies demonstrate that drugs gain direct access to the CSF from the nasal cavity, followed by subsequent distribution to the brain and spinal cord. Many intranasally applied molecules rapidly enter the CSF, and this transport is dependent on the lipophilicity, molecular weight, and degree of ionization of the molecules (Dhanda et al., 2005; Born et al., 2002; Kumar et al., 1974; Sakane et al., 1995; Sakane et al., 1994; Wang et al., 2007). Assessing distribution into the CSF can provide information on the mechanism of intranasal delivery.

Optimal delivery to the CNS along neural pathways is associated with delivery of the agent to the upper third of the nasal cavity (Hanson et al., 2008). Although a supine position may be employed another position for targeting the olfactory region is with the "praying to Mecca" position, with the head down-and-forward. A supine position with the head angle at 70° or 90° may be suitable for efficient delivery to the CSF using a tube inserted into the nostrils to deliver the drug via intranasal administration (van den Berg et al., (2002)).

For intranasal drug administration nose drops may be administered over a period of 10-20 minutes to alternating nostrils every 1-2 minutes to allow the solution to be absorbed into the nasal epithelium (Thorne et al., 2004; Capsoni et al., 2002; Ross et al., 2004; Ross et al., 2008; Dhuria et al., 2009a; Dhuria et al., 2009b; Francis et al., 2008; Martinez et al., 2008). This noninvasive method does not involve inserting the device into the nostril. Instead, drops are placed at the opening of the nostril, allowing the individual to sniff the drop into the nasal cavity. Other administration methods in anesthetized individual involve sealing the esophagus and inserting a breathing tube into the trachea to prevent the nasal formulation from being swallowed and to eliminate issues related to respiratory distress (Chow et al., 1999; Chow et al., 2001; Fliedner et al., 2006; Dahlin et al., 2001). Flexible tubing can be inserted into the nostrils for localized delivery of a small volume of the drug solution to the respiratory or olfactory epithelia, depending on the length of the tubing (Chow et al., 1999; Van den Berg et al., 2003; van den Berg et al., 2004a; Banks et al., 2004; van den Berg et al., 2002; Vyas et al., 2006a; Charlton et al., 2007a; Gao et al., 2007a).

Nasal delivery devices, such as sprays, nose droppers or needle-less syringes, may be employed to target the agent to different regions of the nasal cavity. OptiMist™ is a breath actuated device that targets liquid or powder nasal formulations to the nasal cavity, including the olfactory region, without deposition in the lungs or esophagus (Djupesland et al., 2006). The ViaNase™ device can also be used to target a nasal spray to the olfactory and respiratory epithelia of the nasal cavity. Nasal drops tend to deposit on the nasal floor and are subjected to rapid mucociliary clearance, while nasal sprays are distributed to the middle meatus of the nasal mucosa (Scheibe et al., 2008).

The immune suppressant or immunotolerizing agent may be administered by any route including parenterally. In one embodiment, the immune suppressant or immunotolerizing agent may be administered by subcutaneous, intramuscular, or intravenous injection, orally, intrathecally, intracranially, or intranasally, or by sustained release, e.g., using a subcutaneous implant. The immune suppressant or immunotolerizing agent may be dissolved or dispersed in a liquid carrier vehicle. For parenteral administration, the active material may be suitably admixed with an acceptable vehicle, e.g., of the vegetable oil variety such as peanut oil, cottonseed oil and the like. Other parenteral vehicles such as organic compositions using solketal, glycerol, formal, and aqueous parenteral formulations may also be used. For parenteral application by injection, compositions may comprise an aqueous solution of a water soluble pharmaceutically acceptable salt of the active acids according to the invention, desirably in a concentration of 0.01-10%, and optionally also a stabilizing agent and/or buffer substances in aqueous solution. Dosage units of the solution may advantageously be enclosed in ampules.

The composition, e.g., rAAV containing composition, immune suppressant containing composition or immunotolerizing composition, may be in the form of an injectable unit dose. Examples of carriers or diluents usable for preparing such injectable doses include diluents such as water, ethyl alcohol, macrogol, propylene glycol, ethoxylated isostearyl alcohol, polyoxyisostearyl alcohol and polyoxyethylene sorbitan fatty acid esters, pH adjusting agents or buffers such as sodium citrate, sodium acetate and sodium phosphate, stabilizers such as sodium pyrosulfite, EDTA, thioglycolic acid and thiolactic acid, isotonic agents such as sodium chloride and glucose, local anesthetics such as procaine hydrochloride and lidocaine hydrochloride. Furthermore usual solubilizing agents and analgesics may be added. Injections can be prepared by adding such carriers to the enzyme or other active, following procedures well known to those of skill in the art. A thorough discussion of pharmaceutically acceptable excipients is available in REMINGTON'S PHARMACEUTICAL SCIENCES (Mack Pub. Co., N.J. 1991). The pharmaceutically acceptable formulations can easily be suspended in aqueous vehicles and introduced through conventional hypodermic needles or using infusion pumps. Prior to introduction, the formulations can be sterilized with, preferably, gamma radiation or electron beam sterilization.

When the immune suppressant or immunotolerizing agent is administered in the form of a subcutaneous implant, the compound is suspended or dissolved in a slowly dispersed material known to those skilled in the art, or administered in a device which slowly releases the active material through the use of a constant driving force such as an osmotic pump. In such cases, administration over an extended period of time is possible.

The dosage at which the immune suppressant or immunotolerizing agent containing composition is administered may vary within a wide range and will depend on various factors such as the severity of the disease, the age of the patient, etc., and may have to be individually adjusted. A possible range for the amount which may be administered per day is about 0.1 mg to about 2000 mg or about 1 mg to about 2000 mg. The compositions containing the immune suppressant or immunotolerizing agent may suitably be formulated so that they provide doses within these ranges, either as single dosage units or as multiple dosage units. In addition to containing an immune suppressant, the subject formulations may contain one or more rAAV encoding a therapeutic gene product.

Compositions described herein may be employed in combination with another medicament. The compositions can appear in conventional forms, for example, aerosols, solutions, suspensions, or topical applications, or in lyophilized form.

Typical compositions include a rAAV, an immune suppressant, a permeation enhancer, or a combination thereof, and a pharmaceutically acceptable excipient which can be a carrier or a diluent. For example, the active agent(s) may be mixed with a carrier, or diluted by a carrier, or enclosed within a carrier. When the active agent is mixed with a carrier, or when the carrier serves as a diluent, it can be solid, semi-solid, or liquid material that acts as a vehicle, excipient, or medium for the active agent. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active agent(s).

Such additives can include wetting agents, emulsifying and suspending agents, salt for influencing osmotic pressure, buffers and/or coloring substances preserving agents, sweetening agents or flavoring agents. The compositions can also be sterilized if desired.

If a liquid carrier is used, the preparation can be in the form of a liquid such as an aqueous liquid suspension or solution. Acceptable solvents or vehicles include sterilized water, Ringer's solution, or an isotonic aqueous saline solution.

The agent(s) may be provided as a powder suitable for reconstitution with an appropriate solution as described above. Examples of these include, but are not limited to, freeze dried, rotary dried or spray dried powders, amorphous powders, granules, precipitates, or particulates. The composition can optionally contain stabilizers, pH modifiers, surfactants, bioavailability modifiers and combinations of these. A unit dosage form can be in individual containers or in multi-dose containers.

Compositions contemplated by the present invention may include, for example, micelles or liposomes, or some other encapsulated form, or can be administered in an extended release form to provide a prolonged storage and/or delivery effect, e.g., using biodegradable polymers, e.g., polylactide-polyglycolide. Examples of other biodegradable polymers include poly(orthoesters) and poly(anhydrides).

Polymeric nanoparticles, e.g., comprised of a hydrophobic core of polylactic acid (PLA) and a hydrophilic shell of methoxy-poly(ethylene glycol) (MPEG), may have improved solubility and targeting to the CNS. Regional differences in targeting between the microemulsion and nanoparticle formulations may be due to differences in particle size.

Liposomes are very simple structures consisting of one or more lipid bilayers of amphiphilic lipids, i.e., phospholipids or cholesterol. The lipophilic moiety of the bilayers is turned towards each other and creates an inner hydrophobic environment in the membrane. Liposomes are suitable drug carriers for some lipophilic drugs which can be associated with the non-polar parts of lipid bilayers if they fit in size and geometry. The size of liposomes varies from 20 nm to few μm.

Mixed micelles are efficient detergent structures which are composed of bile salts, phospholipids, tri, di- and mono-glycerides, fatty acids, free cholesterol and fat soluble micronutrients. As long-chain phospholipids are known to form bilayers when dispersed in water, the preferred phase of short chain analogues is the spherical micellar phase. A micellar solution is a thermodynamically stable system formed spontaneously in water and organic solvents. The interaction between micelles and hydrophobic/lipophilic drugs leads to the formation of mixed micelles (MM), often called swallen micelles, too. In the human body, they incorporate hydrophobic compounds with low aqueous solubility and act as a reservoir for products of digestion, e.g. monoglycerides.

Lipid microparticles includes lipid nano- and microspheres. Microspheres are generally defined as small spherical particles made of any material which are sized from about 0.2 to 100 μm. Smaller spheres below 200 nm are usually called nanospheres. Lipid microspheres are homogeneous oil/water microemulsions similar to commercially available fat emulsions, and are prepared by an intensive sonication procedure or high pressure emulsifying methods (grinding methods). The natural surfactant lecithin lowers the surface tension of the liquid, thus acting as an emulsifier to form a stable emulsion. The structure and composition of lipid nanospheres is similar to those of lipid microspheres, but with a smaller diameter.

Polymeric nanoparticles serve as carriers for a broad variety of ingredients. The active components may be either dissolved in the polymetric matrix or entrapped or adsorbed onto the particle surface. Polymers suitable for the preparation of organic nanoparticles include cellulose derivatives and polyesters such as poly(lactic acid), poly(glycolic acid) and their copolymer. Due to their small size, their large surface area/volume ratio and the possibility of functionalization of the interface, polymeric nanoparticles are ideal carrier and release systems. If the particle size is below 50 nm, they are no longer recognized as particles by many biological and also synthetic barrier layers, but act similar to molecularly disperse systems.

Thus, the composition of the invention can be formulated to provide quick, sustained, controlled, or delayed release, or any combination thereof, of the active agent after administration to the individual by employing procedures well known in the art. In one embodiment, the enzyme is in an isotonic or hypotonic solution. In one embodiment, for enzymes that are not water soluble, a lipid based delivery vehicle may be employed, e.g., a microemulsion such as that described in WO 2008/049588, the disclosure of which is incorporated by reference herein, or liposomes.

In one embodiment, the preparation can contain an agent, dissolved or suspended in a liquid carrier, such as an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens. For example, in addition to solubility, efficient delivery to the CNS following intranasal administration may be dependent on membrane permeability. For enzymes where paracellular transport is hindered due to size and polarity, improving membrane permeability may enhance extracellular mechanisms of transport to the CNS along olfactory and trigeminal nerves. One approach to modifying membrane permeability within the nasal epithelium is by using permeation enhancers, such as surfactants, e.g., lauroylcarnitine (LC), bile salts, lipids, cyclodextrins, polymers, or tight junction modifiers.

Generally, the active agents are dispensed in unit dosage form including the active ingredient together with a pharmaceutically acceptable carrier per unit dosage. Usually, dosage forms suitable for nasal administration include from about 125 μg to about 125 mg, e.g., from about 250 μg to about 50 mg, or from about 2.5 mg to about 25 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

The invention will be described by the following non-limiting examples.

Example I

AAV Vector-Mediated Iduronidase Gene Delivery in a Murine Model of Mucopolysaccharidosis Type I: Comparing Different Routes of Delivery to the CNS Mucopolysaccharidosis type I (MPS I) is an inherited metabolic disorder caused by deficiency of the lysosomal enzyme alpha-L-iduronidase (IDUA). Systemic and abnormal accumulation of glycosaminoglycans is associated with growth delay, organomegaly, skeletal dysplasia, and cardiopulmonary disease. Individuals with the most severe form of the disease (Hurler syndrome) suffer from neurodegeneration, mental retardation, and early death. The two current treatments for MPSI (hematopoietic stem cell transplantation and enzyme replacement therapy) cannot effectively treat all central nervous system (CNS) manifestations of the disease.

Figure 18:
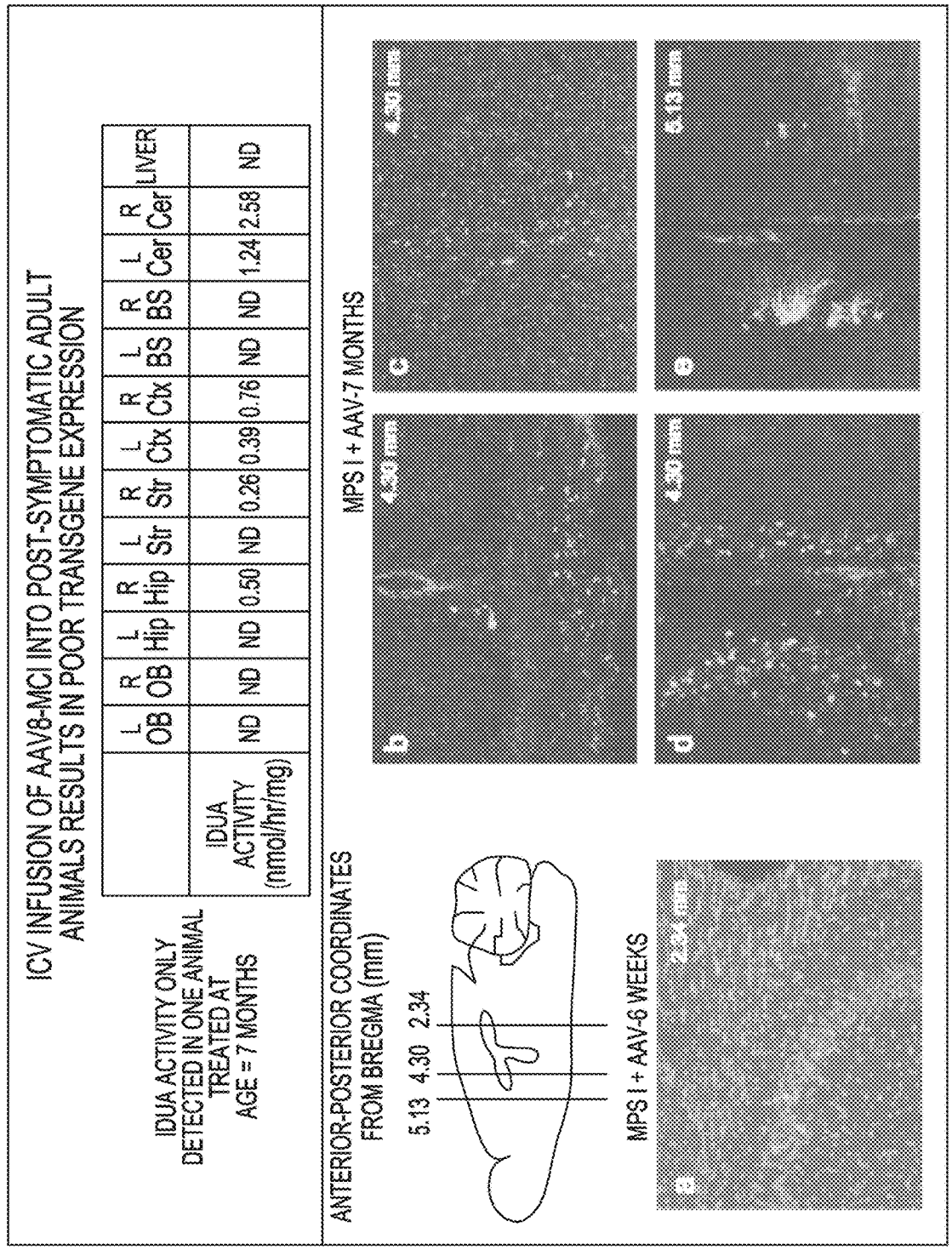
FIG. 18. ICV infusion of AAV8-MCI into adult animals.

With respect to gene therapy, it was previously demonstrated that intravascular delivery of AAV-9 in adult mice does not achieve widespread direct neuronal targeting (see Foust et al, 2009). Previous work also showed that direct injection of AAV8-IDUA into the CNS of adult IDUA-deficient mice resulted in a low frequency or a poor level of transgene expression (see FIG. 18). The following examples, which use a pre-clinical model for the treatment of MPSI, surprisingly demonstrate that direct injection of AAV9-IDUA into the CNS of immunocompetent adult IDUA-deficient mice resulted in IDUA enzyme expression and activity that is the same or higher than IDUA enzyme expression and activity in wild-type adult mice (see FIG. 15, infra).

Methods

AAV9-IDUA Preparation.

The AAV-IDUA vector construct (MCI) has been previously described (Wolf et al., 2011) (mCags promoter). AAV-IDUA plasmid DNA was packaged into AAV9 virions at the University of Florida Vector Core, yielding a titer of $3 \times 10^{13}$ vector genomes per milliliter.

ICV Infusions.

Adult Idua−/− mice were anesthetized using a cocktail of ketamine and xylazine (100 mg ketamine+10 mg xylazine per kg) and placed on a stereotactic frame. Ten microliters of AAV9-IDUA were infused into the right-side lateral ventricle (stereotactic coordinates AP 0.4, ML 0.8, DV 2.4 mm from bregma) using a Hamilton syringe. The animals were returned to their cages on heating pads for recovery.

Intrathecal Infusions.

Infusions into young adult mice were carried out by injection of 10 µL AAV vector containing solution between the L5 and L6 vertebrae 20 minutes after intravenous injection of 0.2 mL 25% mannitol.

Immunotolerization.

Newborn IDUA deficient mice were injected through the facial temporal vein with 5 µL containing 5.8 µg of recombinant iduronidase protein (Aldurazyme), and then the animals were returned to their cage.

Cyclophosphamide Immunosuppression.

For immunosuppression, animals were administered cyclophosphamide once per week at a dose of 120 mg/kg starting one day after infusion with AAV9-IDUA vector.

Animals.

Animals were anesthetized with ketamine/xylazine (100 mg ketamine+10 mg xylazine per kg) and transcardially perfused with 70 mL PBS prior to sacrifice. Brains were harvested and microdissected on ice into cerebellum, hippocampus, striatum, cortex, and brainstem/thalamus ("rest"). The samples were frozen on dry ice and then stored at −80° C. Samples were thawed and homogenized in 1 mL of PBS using a motorized pestle and permeabilized with 0.1% Triton X-100. IDUA activity was determined by fluorometric assay using 4MU-iduronide as the substrate. Activity is expressed in units (percent substrate converted to product per minute) per mg protein as determined by Bradford assay (BioRad).

Tissues.

Tissue homogenates were clarified by centrifugation for 3 minutes at 13,000 rpm using an Eppendorf tabletop centrifuge model 5415D (Eppendorf) and incubated overnight with proteinase K, DNase1, and Rnase. GAG concentration was determined using the Blyscan Sulfated Glycosaminoglycan Assay (Accurate Chemical) according to the manufacturer's instructions.

Results

FIG. 1 shows the results for iduronidase-deficient mice that were administered AAV either intracerebroventricularly (ICV) or intrathecally (IT). To prevent immune response, animals were either immunosuppressed with cyclophosphamide (CP), immunotolerized at birth by intravenous administration of human iduonidase protein (aldurazyme), or the injections were carried out in NOD-SCID immunodeficient mice that were also iduronidase deficient. Animals were sacrificed at the indicated time post-treatment, the brains were microdissected and extracts assayed for iduronidase activity.

Figure 2B:
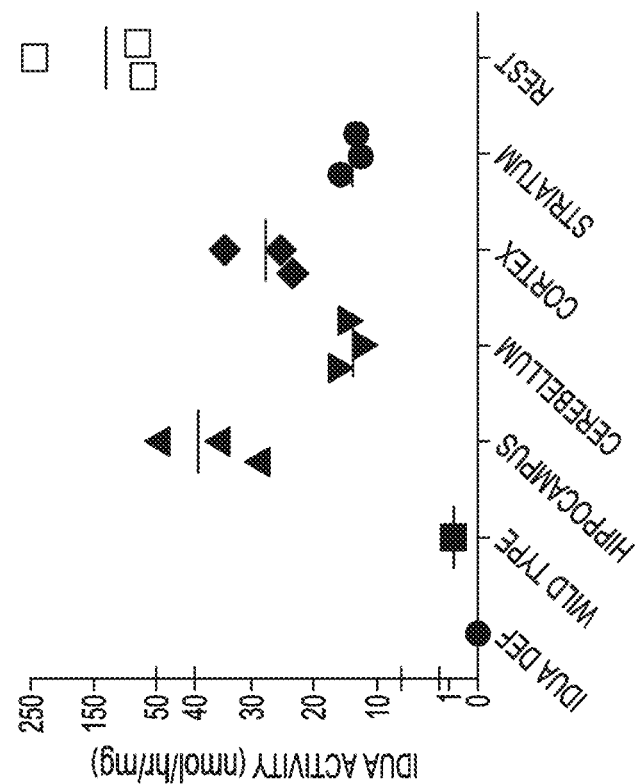
FIGS. 2A-B. IDUA activity in immunodeficient, IDUA deficient animals after ICV injection.
Figure 2A:
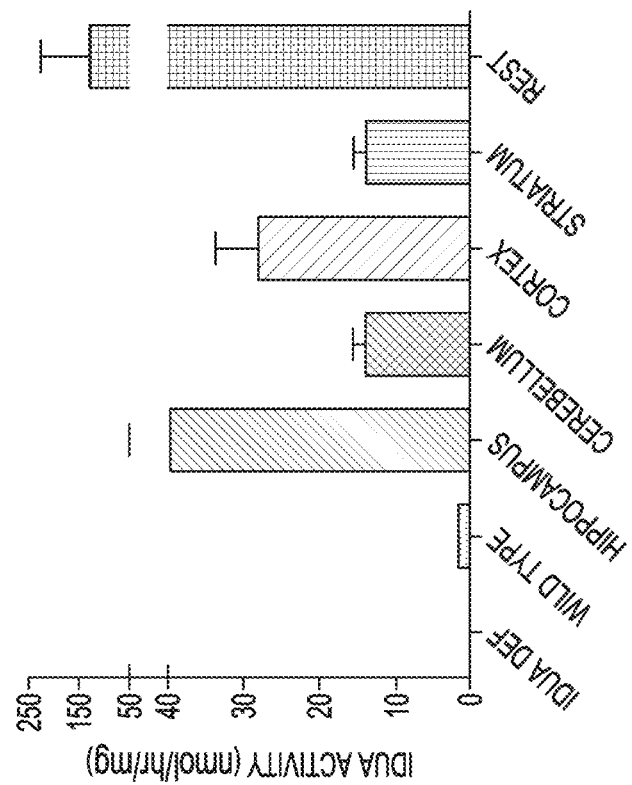

FIG. 2 illustrates data for immunodeficient, IDUA deficient animals injected ICV with AAV-IDUA vector. Those animals exhibited high levels of IDUA expression (10 to 100 times wild type) in all areas of the brain, with the highest level observed in the brain stem and thalamus ("rest").

Figure 3B:
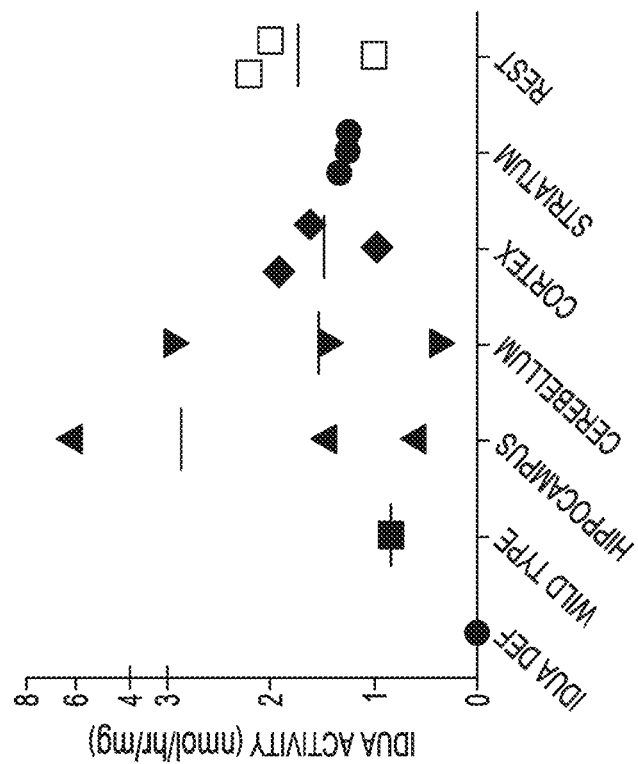
FIGS. 3A-B. IDUA activity in immunocompetent animals administered AAV vector by ICV route and treated with cyclophosphamide.
Figure 3A:
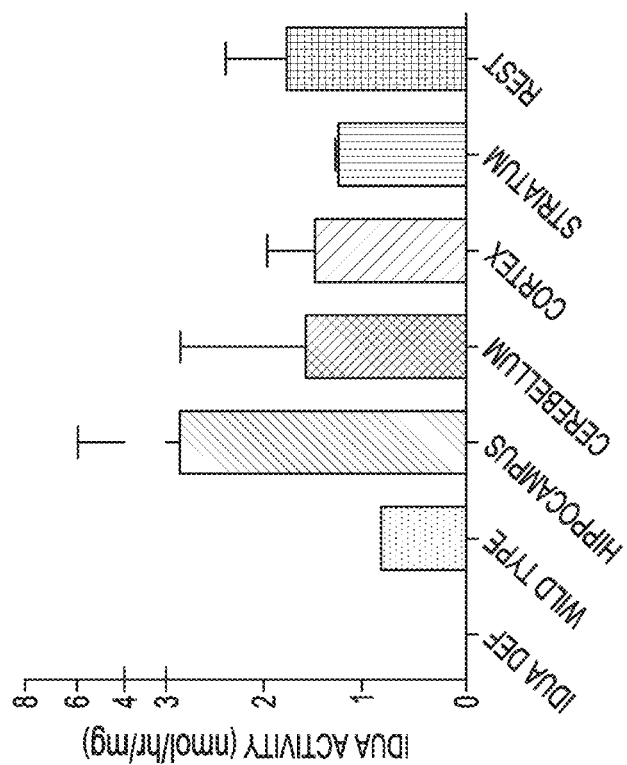

Immunosuppressed animals administered AAV vector by ICV route had a relatively lower level of enzyme in the brain compared to the immunodeficent animals (FIG. 3). Note that immunosuppression may have been compromised in these animals because CP was withdrawn 2 weeks before sacrifice due to poor health.

Figure 4B:
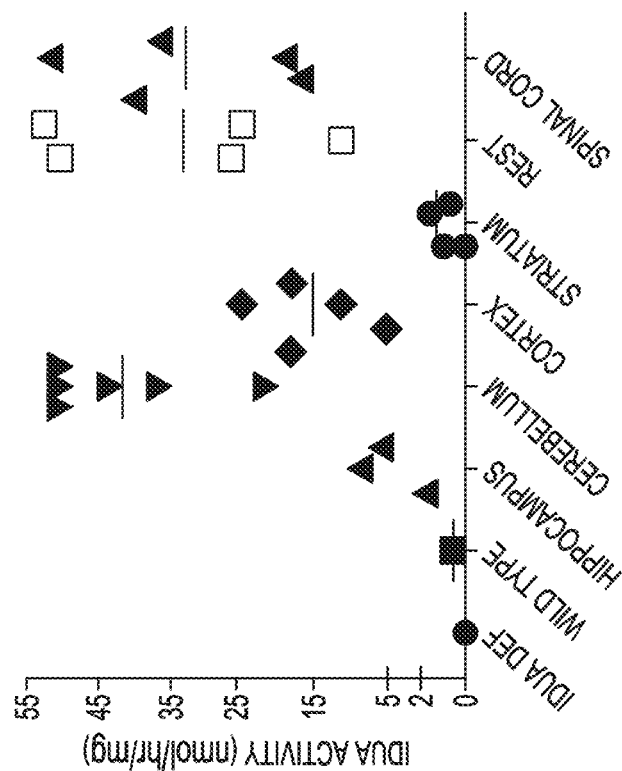
FIGS. 4A-B. IDUA activity in immunocompetent animals administered AAV vector by IT route and treated with cyclophosphamide.
Figure 4A:
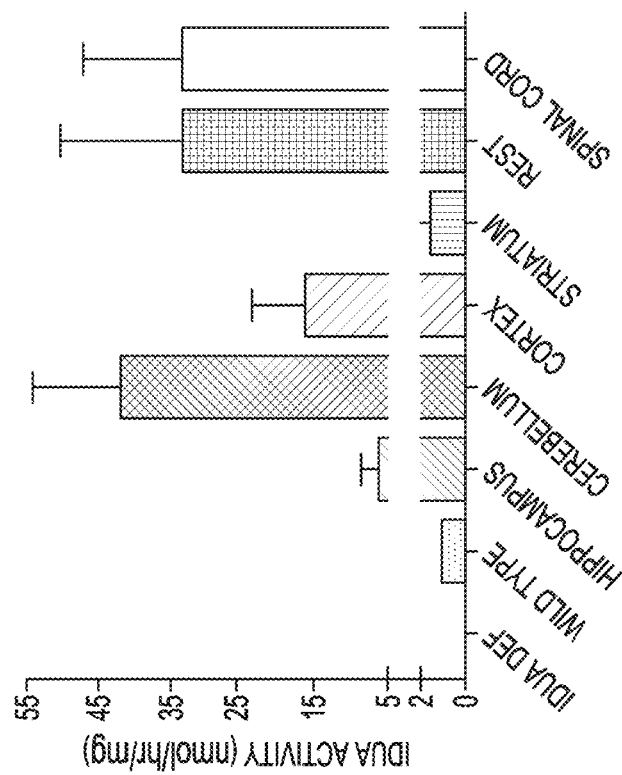
Figure 5B:
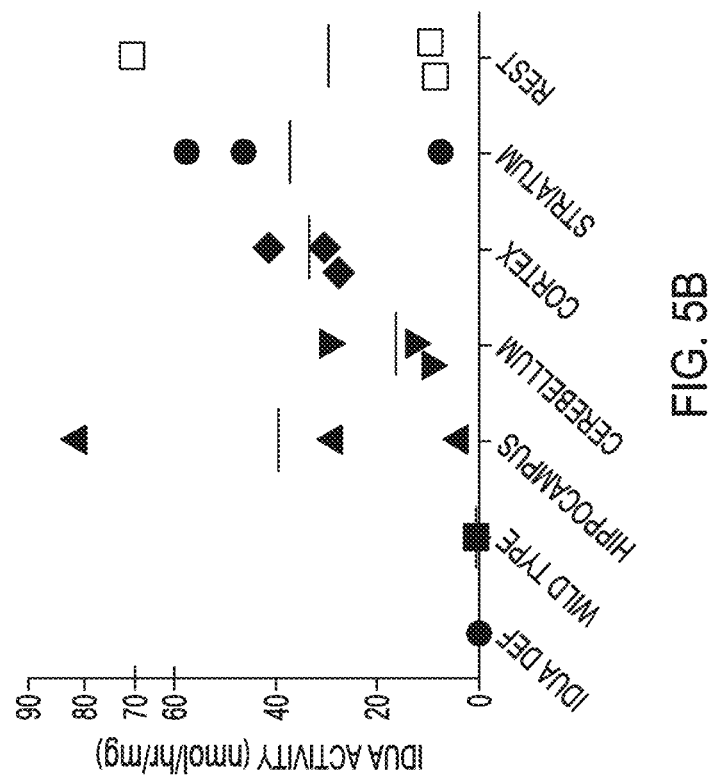
FIGS. 5A-B. IDUA activity in immunotolerized immunocompetent animals administered AAV vector ICV.
Figure 5A:
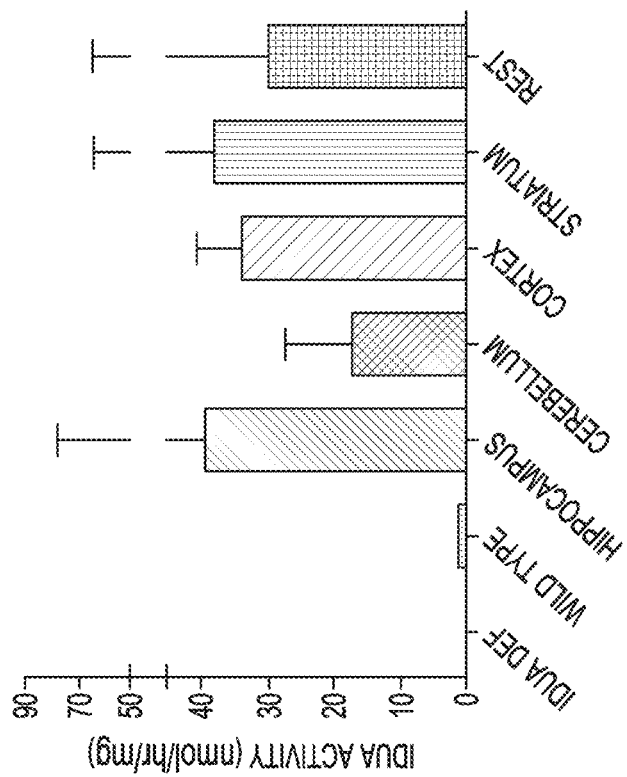

FIG. 4 shows data for immunosuppressed animals administered AAV vector by the IT route. Immunotolerized animals administered AAV vector ICV exhibited widespread IDUA activity in all parts of the brain (FIG. 5), similar to that observed in the immunodeficient animals, indicating the effectiveness of the immunotolerization procedure.

Figure 6:
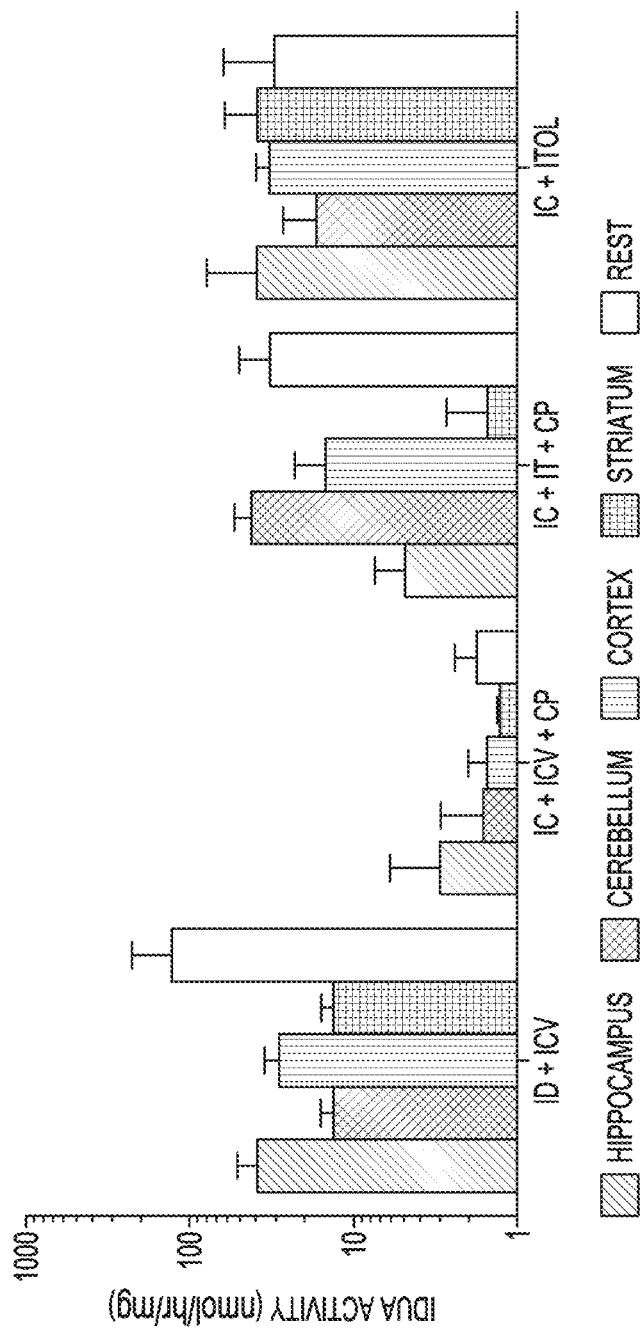
FIG. 6. Compilation of all mean levels of IDUA activity for side-by-side comparison.
Figure 8A:
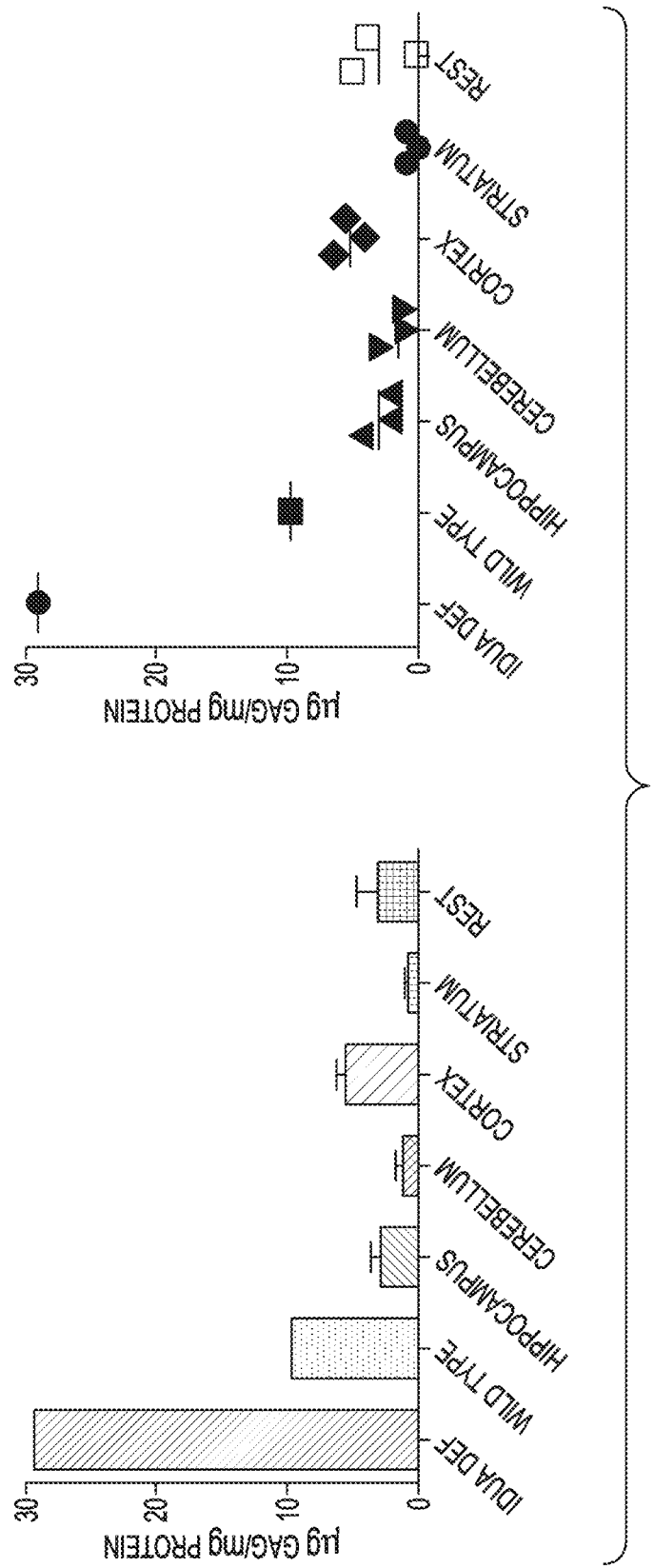
FIGS. 8A-D. Assay for GAG storage material in the different sections of the brain for all four of the test groups. A) Immunodeficient mice. ICV administration. B) Immunocompetent mice, ICV administration and CP administration. C) Immunocompetent mice, ICV administration and aldurazyme administration. D) Immunocompetent mice. IT administration and CP administration.
Figure 8B:
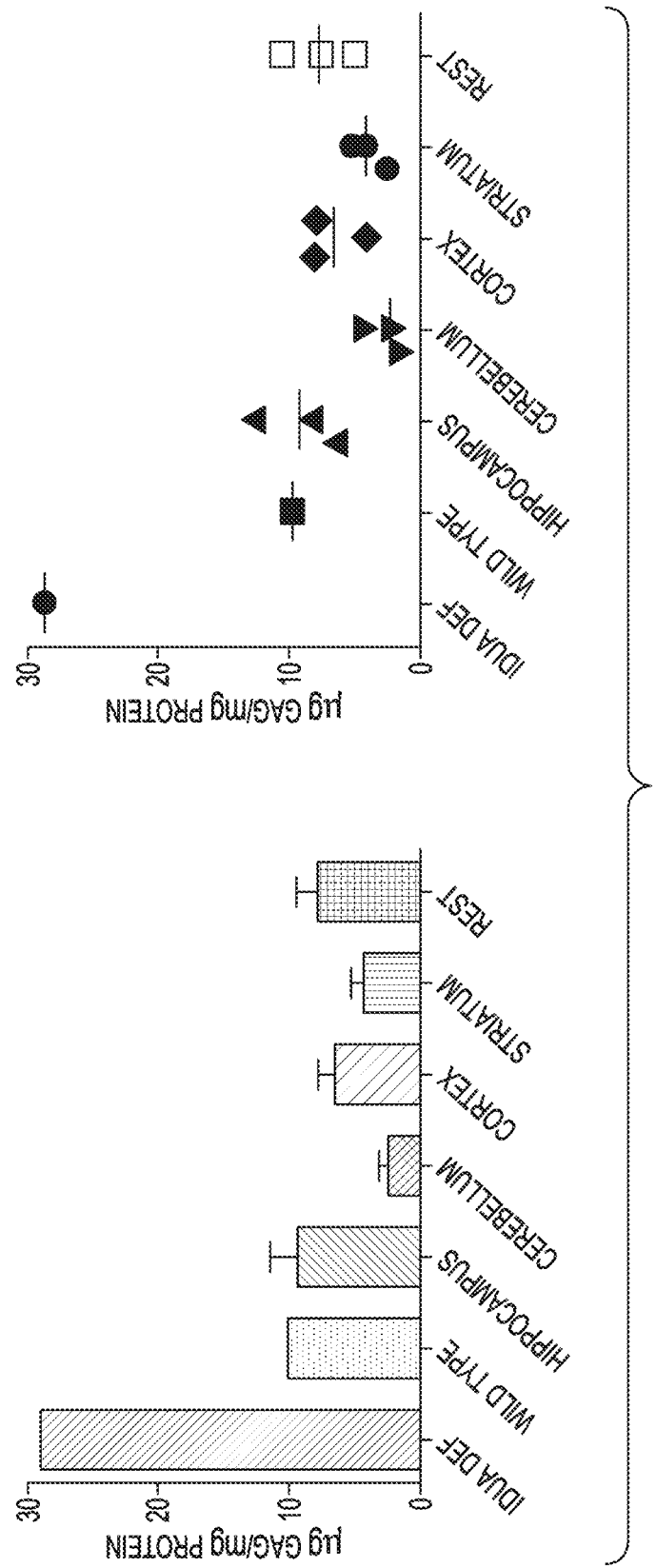
Figure 8C:
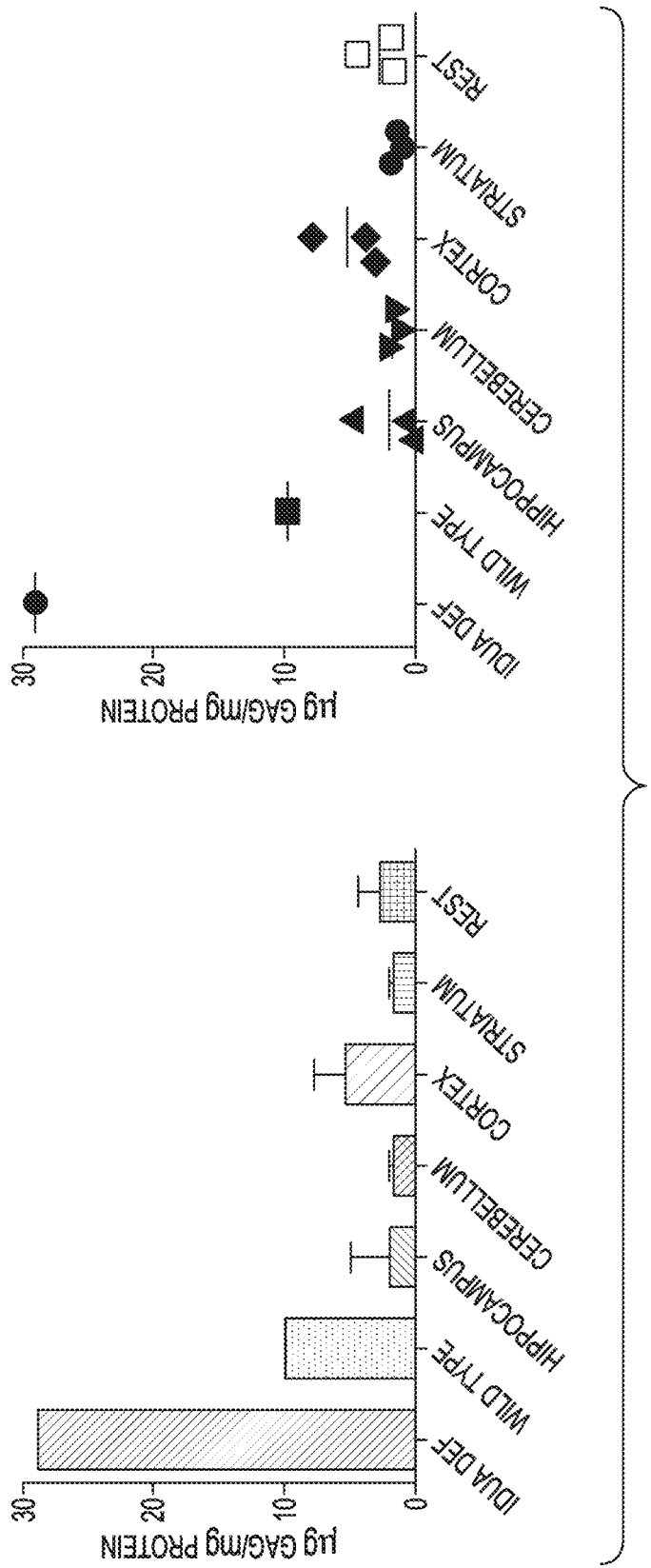
Figure 8D:
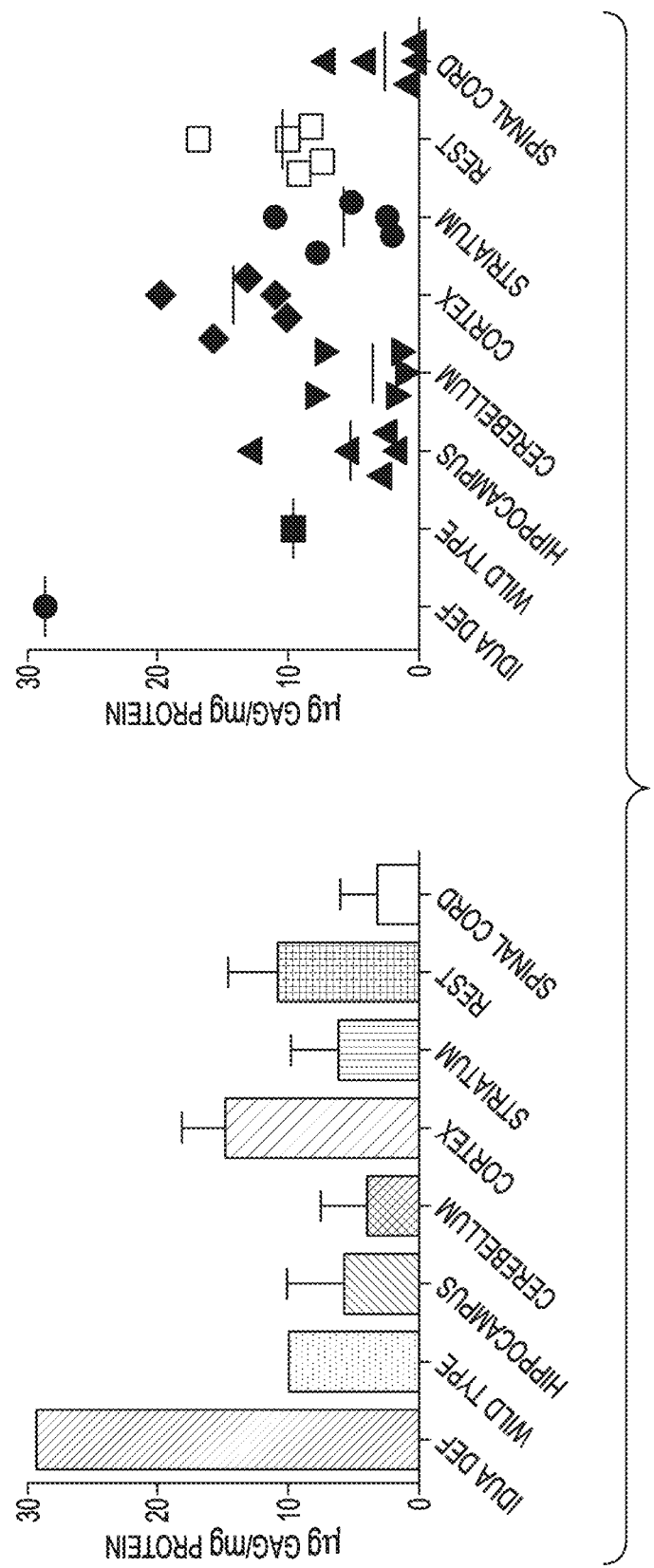

FIG. 6 is a compilation of all mean levels of IDUA activity for side-by-side comparison, and FIG. 7 is data grouped according the area of the brain.

GAG storage material was assayed in the different sections of the brain for all four of the test groups. For each group, the mean of each portion of the brain is shown on the left, the values for each of the individual animals is shown on the right (FIG. 8). IDUA deficient animals (far left) contained high levels of GAG compared to wild type animals (magenta bar). GAG levels were at wild-type or lower than wild type for all portions of the brain in all groups of AAV-treated animals. GAG levels were slightly although not significantly higher than wild-type in cortex and brainstem of animals administered AAV9-IDUA intrathecally.

CONCLUSIONS

The results show high and widespread distribution of IDUA in the brain regardless of the route of delivery (ICV or IT) although IDUA expression in striatum and hippocampus was lower in animals injected IT versus ICV. There appears to be an immune response since immune deficient mice have higher levels of expression than immunocompetent mice. With regard to ICV injection, when CP was withdrawn early, IDUA expression is lower. In addition, immunotolerization was effective in restoring high levels of enzyme activity. Further, GAG levels were restored to normal in all treated experimental groups of mice.

Example II

Methods

AAV9IDUA Preparation.

AAV-IDUA plasmid was packaged into AAV9 virions at either the University of Florida vector core, or the University of Pennsylvania vector core, yielding a titer of $1-3\times10^{13}$ vector genomes per milliliter.

ICV Infusions.

See Example I.

Intrathecal Infusions.

See Example I.

Immunotolerization.

As in Example I except: for multiple tolerizations, newborn IDUA deficient mice were injected with the first dose of Aldurazyme in the facial temporal vein, followed by 6 weekly injections administered intraperitoneally.

Cyclophosphamide Immunosuppression.

See Example I.

Animals.

Animals were anesthetized with ketamine/xylazine (100 mg ketamine+10 mg xylazine per kg) and transcardially perfused with 70 mL PBS prior to sacrifice. Brains were harvested and microdissected on ice into cerebellum, hippocampus, striatum, cortex, and brainstem/thalamus ("rest"). The samples were frozen on dry ice and then stored at −80° C.

Tissue IDUA Activity.

Tissue samples were thawed and homogenized in saline in a tissue homogenizer. Tissue homogenates were clarified by centrifugation at 15,000 rpm in a benchtop Eppendorf centrifuge at 4° C. for 15 minutes. Tissue lysates (supernatant) were collected and analyzed for IDUA activity and GAG storage levels.

Tissue GAG Levels.

Tissue lysates were incubated overnight with Proteinase K, RNase and DNase. GAG levels were analyzed using the Blyscan Sulfated Glycosaminoglycan Assay according to the manufacturer's instructions.

IDUA Vector Copies.

Tissue homogenates were used for DNA isolation and subsequent QPCR, as described in Wolf et al. (2011).

Results

FIG. 9 illustrates the experimental design and groups. Animals were administered AAV9IDUA vector either by intracerebroventricular (ICV) or intrathecal (IT) infusion. Vector administration was carried out in NOD-SCID immunodeficient (ID) mice that were also IDUA deficient, or in IDUA deficient mice that were either immunosuppressed with cyclophosphamide (CP), or immunotolerized at birth by a single or multiple injections of human iduronidase protein (Aldurazyme). The times of treatment with vector and sacrifice are as indicated in FIG. 9. All vector administrations were carried out in adult animals ranging in age from 3-4.5 months. Animals were injected with 10 µL of vector at a dose of $3\times10^{11}$ vector genomes per 10 microliters.

Figure 10B:
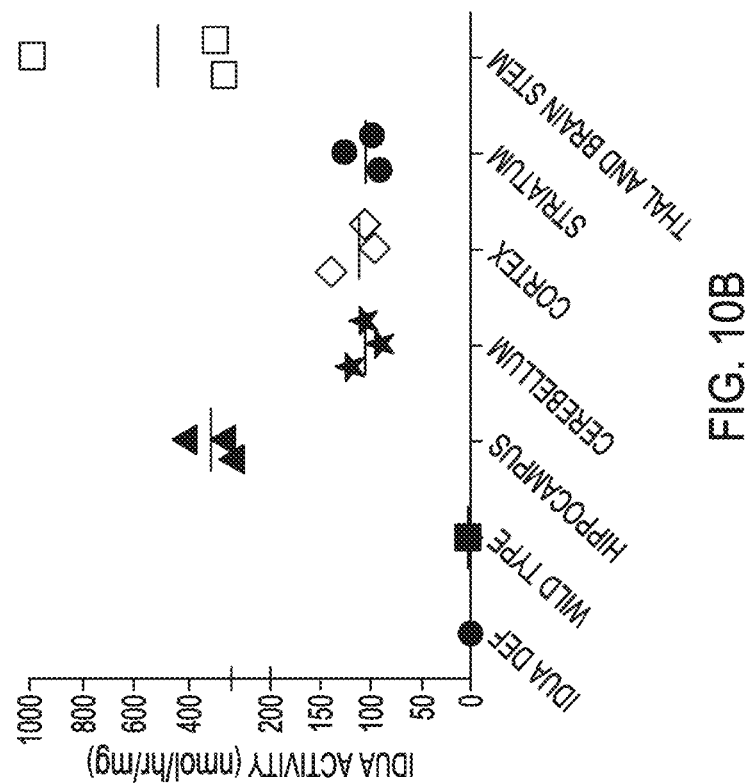
FIGS. 10A-B. Intracranial infusion of AAV9IDUA into immunodeficient MPS I mice. Adult animals were injected with $10^{11}$ vector genomes and evaluated for iduronidase expression in the brain after 10 weeks. Enzyme activity levels in the brain were significantly higher than in the brains of wild type animals, and ranged from 30- to 300-fold higher than wild type.
Figure 10A:
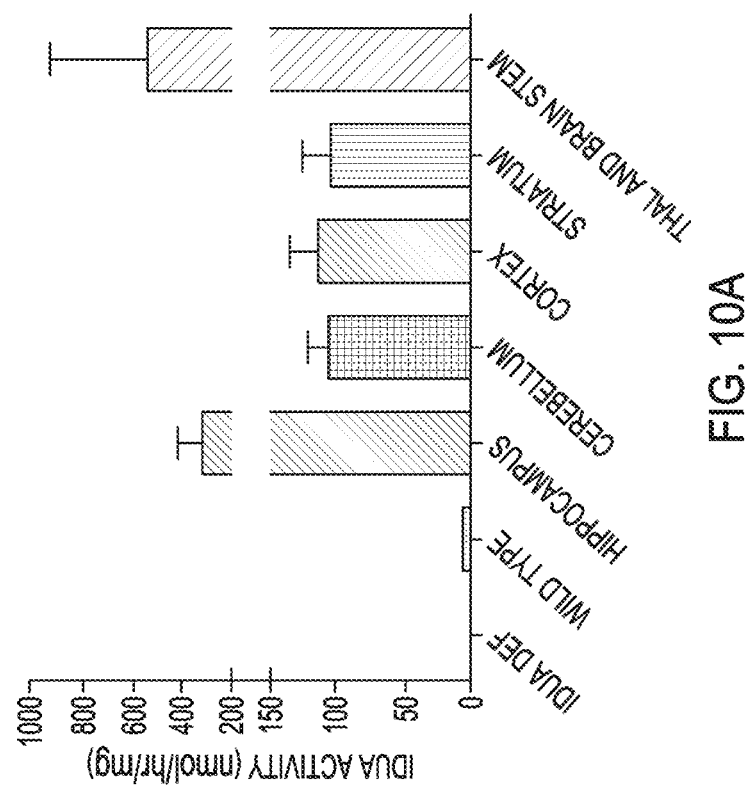

FIG. 10 shows IDUA enzyme activities in intracranially infused, immunodeficient, IDUA deficient mice. High levels of enzyme activity were seen in all areas of the brain, ranging from 30- to 300-fold higher than wild type levels. Highest enzyme expressions were seen in thalamus and brain stem, and in the hippocampus.

Figure 11B:
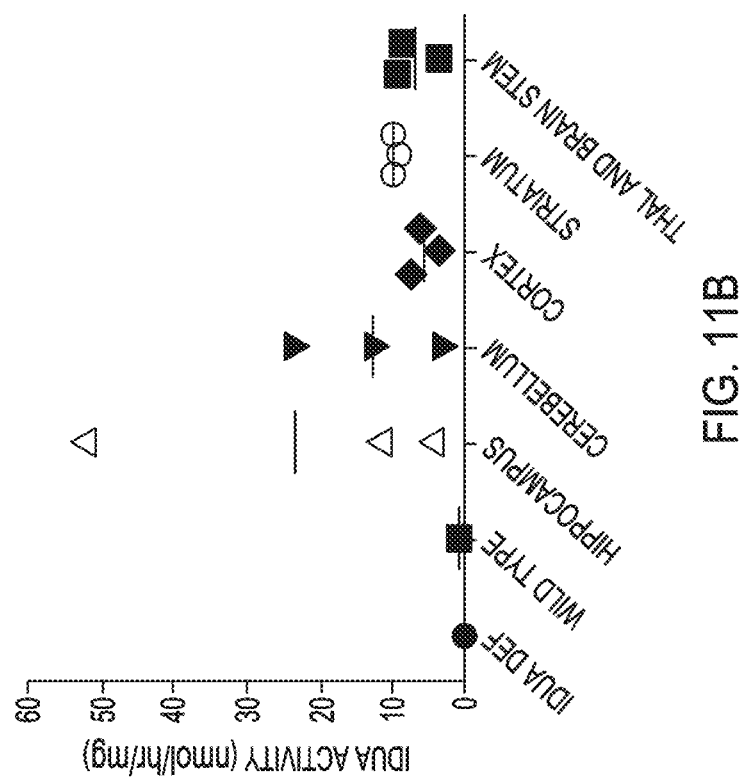
FIGS. 11A-B. Intracranial administration of AAV9IDUA in immunocompetent, IDUA deficient mice. Adult animals were injected with $10^{11}$ vector genomes, and immunosuppressed by weekly injection of cyclophosphamide (CP). CP injections were terminated at 6 weeks post vector injection due to poor health, and the animals were sacrificed at 8 weeks post-injection. Brains were microdissected and assayed for IDUA enzyme activity.
Figure 11A:
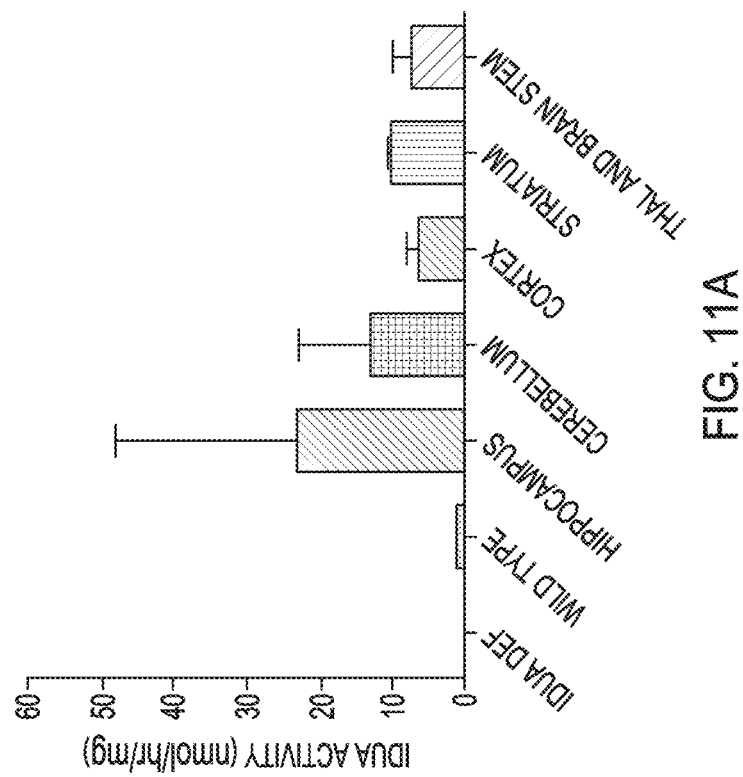

Animals that were injected intracranially and immunosuppressed with cyclophosphamide (CP) demonstrated significantly lower levels of enzyme activity than other groups (FIG. 11). However, CP administration in this case had to be withdrawn 2 weeks prior to sacrifice due to poor health of the animals.

Figure 12B:
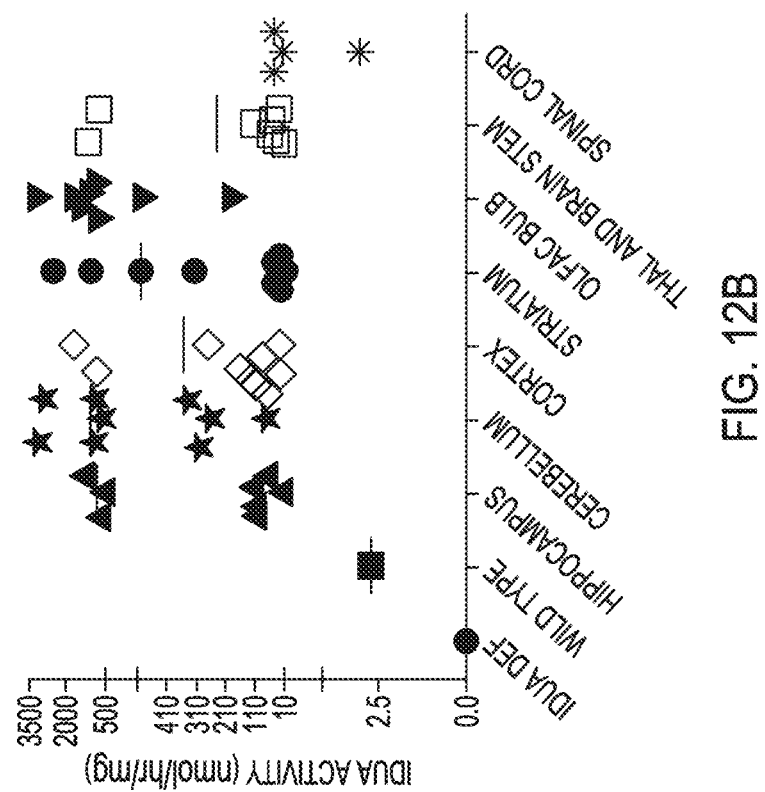
FIGS. 12A-B. Intracranial infusion of AAV9IDUA into immunotolerized MPS I mice. MPS 1 mice were tolerized with either a single dose of Aldurazyme at birth or multiple doses administered weekly, starting at birth. Mice were infused with vector at 4 months, and sacrificed at 11 weeks after injection. Brains were microdissected and analyzed for iduronidase expression. Enzyme activities ranged from an average of 10- to 1000-fold higher than wild type levels.
Figure 12A:
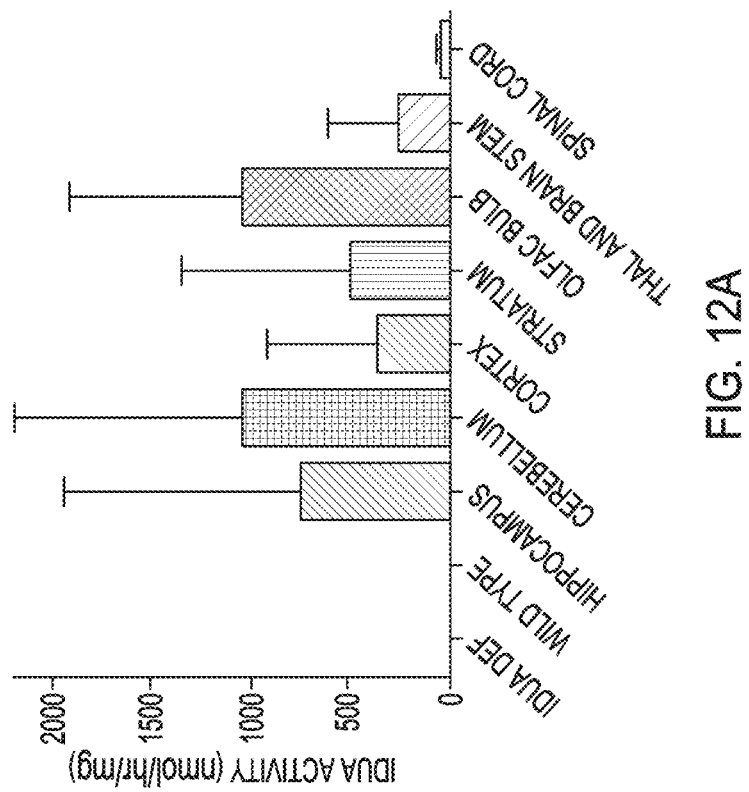

IDUA enzyme levels in animals tolerized at birth with IDUA protein (Aldurazyme) and administered vector intracranially are depicted in FIG. 12. All animals showed high enzyme levels in all parts of the brain that ranged from 10- to 1000-fold higher than wild type levels, similar to levels achieved in immunodeficient animals, indicating the effectiveness of the immunotolerization procedure.

Figure 13B:
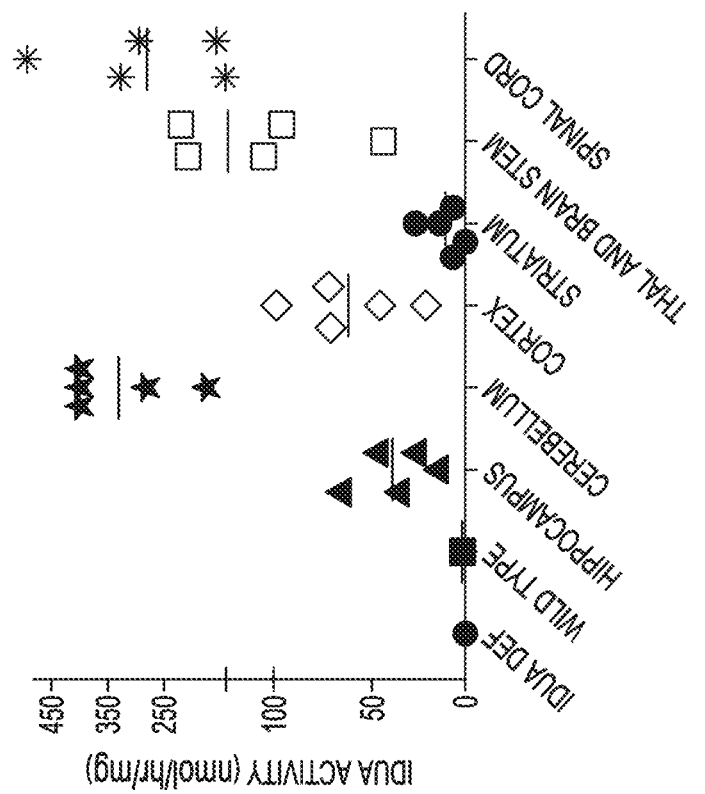
FIGS. 13A-B. Intrathecal administration of AAV9IDUA in immunocompetent, IDUA deficient animals. Adult MPS I mice were injected with AAV9IDUA intrathecally, followed by a weekly immunosuppressive regimen of cyclophosphamide. Animals were sacrificed at 11 weeks post-injection, and then brains and spinal cords were analyzed for IDUA enzyme activity.
Figure 13A:
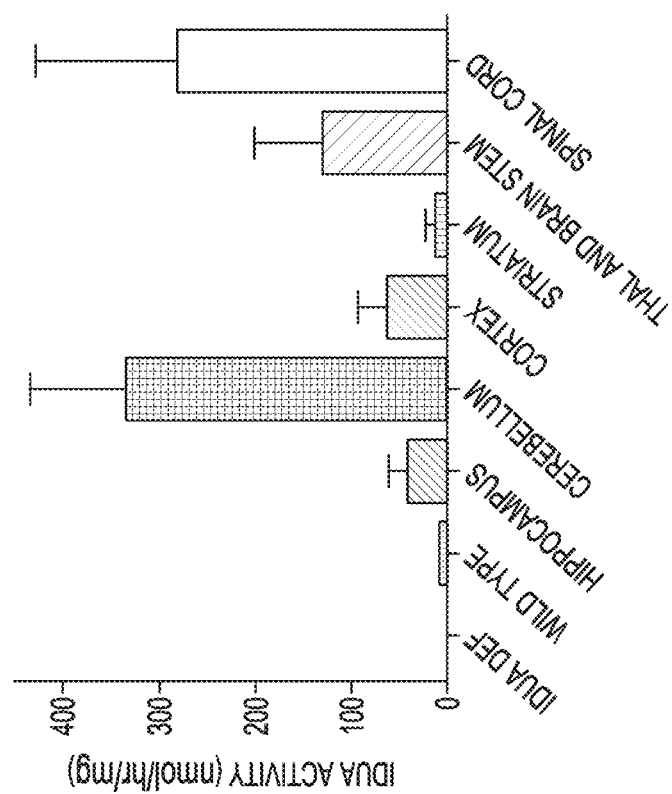

FIG. 13 depicts IDUA enzyme levels in mice that were injected intrathecally and administered CP on a weekly basis. Elevated levels of IDUA were observed in all parts of the brain, especially in the cerebellum and the spinal cord. Levels of enzyme were the lowest in the striatum and hippocampus with activities at wild type levels.

Figure 14B:
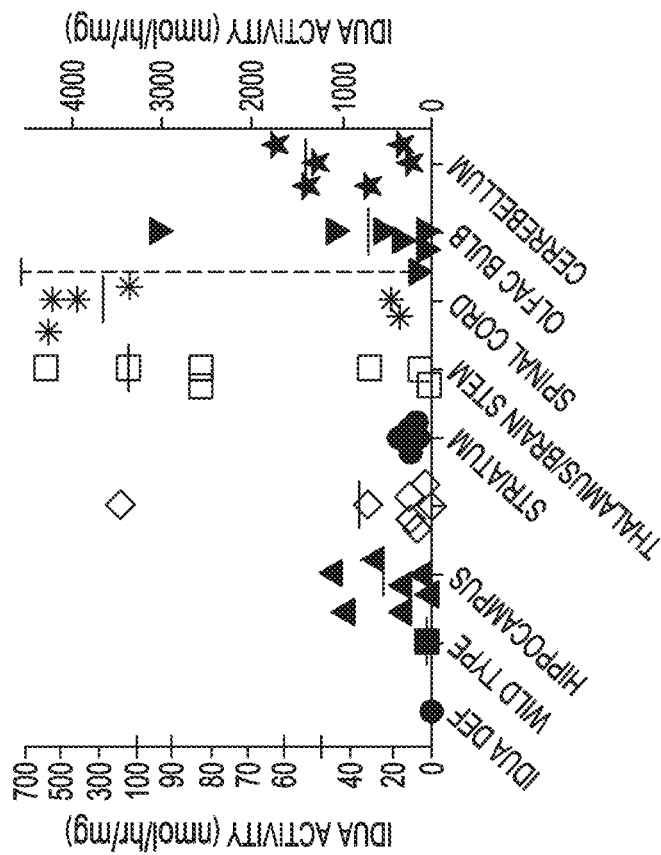
FIGS. 14A-B. Intrathecal infusion of AAV9IDUA in immunotolerized MPS I mice. IDUA deficient animals were tolerized at birth with a single dose of Aldurazyme or multiple doses administered weekly starting at birth. At 4 months of age animals were infused intrathecally with AAV0IDUA vector, and at 10 weeks post-injection animals were sacrificed, brains microdissected and assayed for iduronidase activity. There was restoration of enzyme activity in all parts of the brain, with activities in the cerebellum ranging from 200- to 1500-fold higher than wild type levels. Levels of enzyme activity in the olfactory bulb and cerebellum (to the right of the dashed line) correspond to the right Y-axis.
Figure 14A:
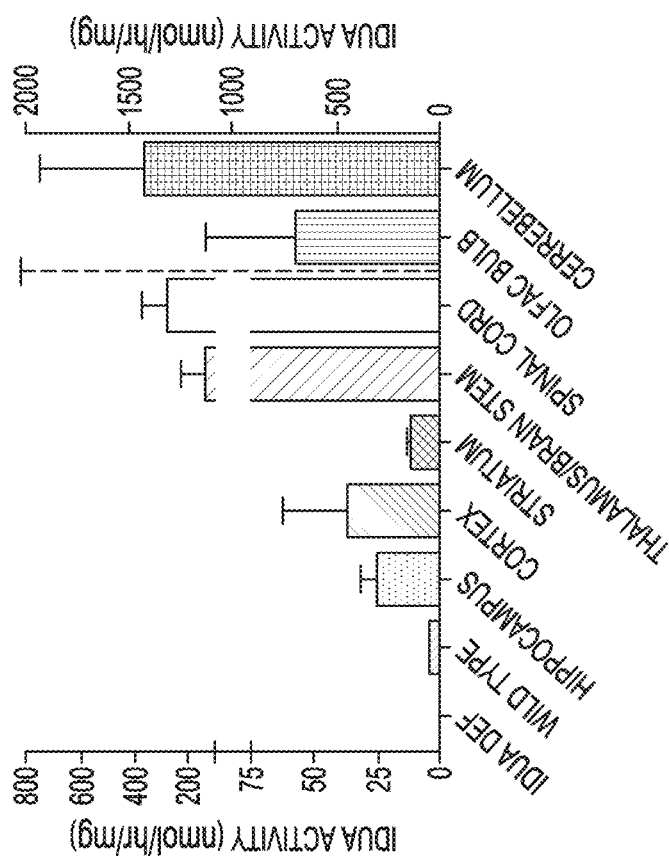

IDUA deficient mice were tolerized with Aldurazyme as described, and injected with vector intrathecally (FIG. 14). There was widespread IDUA enzyme activity in all parts of the brain, with highest levels of activity in the brain stem and thalamus, olfactory bulb, spinal cord and the cerebellum. Similar to the data in FIG. 13, the lowest levels of enzyme activity were seen in the striatum, cortex and hippocampus.

Figure 15B:
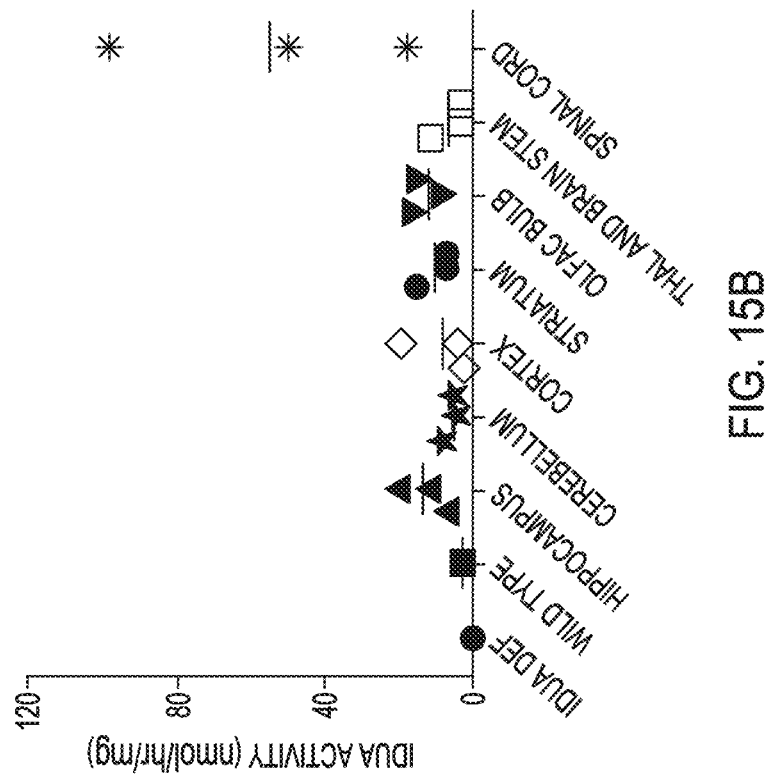
FIGS. 15A-B. Intrathecal infusion of AAV9IDUA in immunocompetent MPS I animals. Control MPS I animals were injected with AAV9IDUA vector, but were not immunosuppressed nor immunotolerized. Animals were sacrificed at 11 weeks after vector injection, and then their brains were assayed for iduronidase activity. Enzyme levels were restored to wild type levels in all parts of the brain, but were significantly lower than in animals that were either immunosuppressed or immunotolerized.
Figure 15A:
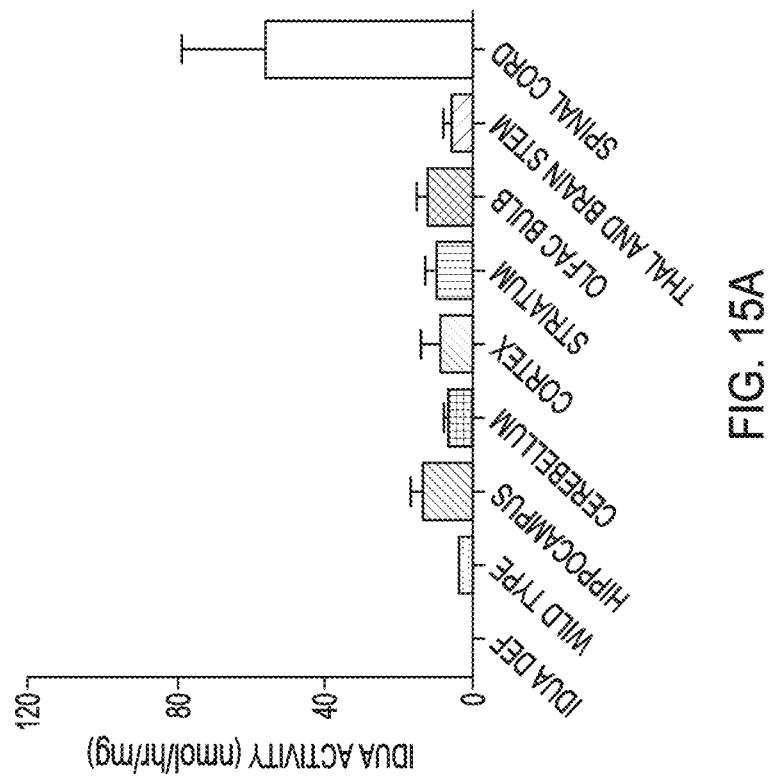

Control immunocompetent IDUA deficient animals were infused with vector intrathecally, without immunosuppression or immunotolerization (FIG. 15). The results indicate that although enzyme activities were at wild type levels or slightly higher, they are significantly lower than what was observed in animals that underwent immunomodulation. The decreases in enzyme levels were especially significant in the cerebellum, olfactory bulb and thalamus and brain stem, areas that expressed the highest levels of enzyme in immunomodulated animals.

Animals were assayed for GAG storage material, as shown in FIG. 15. All groups demonstrated clearance of GAG storage, with GAG levels similar to that observed in wild type animals. Animals that were immunosuppressed and injected with AAV-IDUA vector intrathecally had GAG levels in the cortex that were slightly higher than wild type, but still much lower than untreated IDUA deficient mice.

Figure 16:
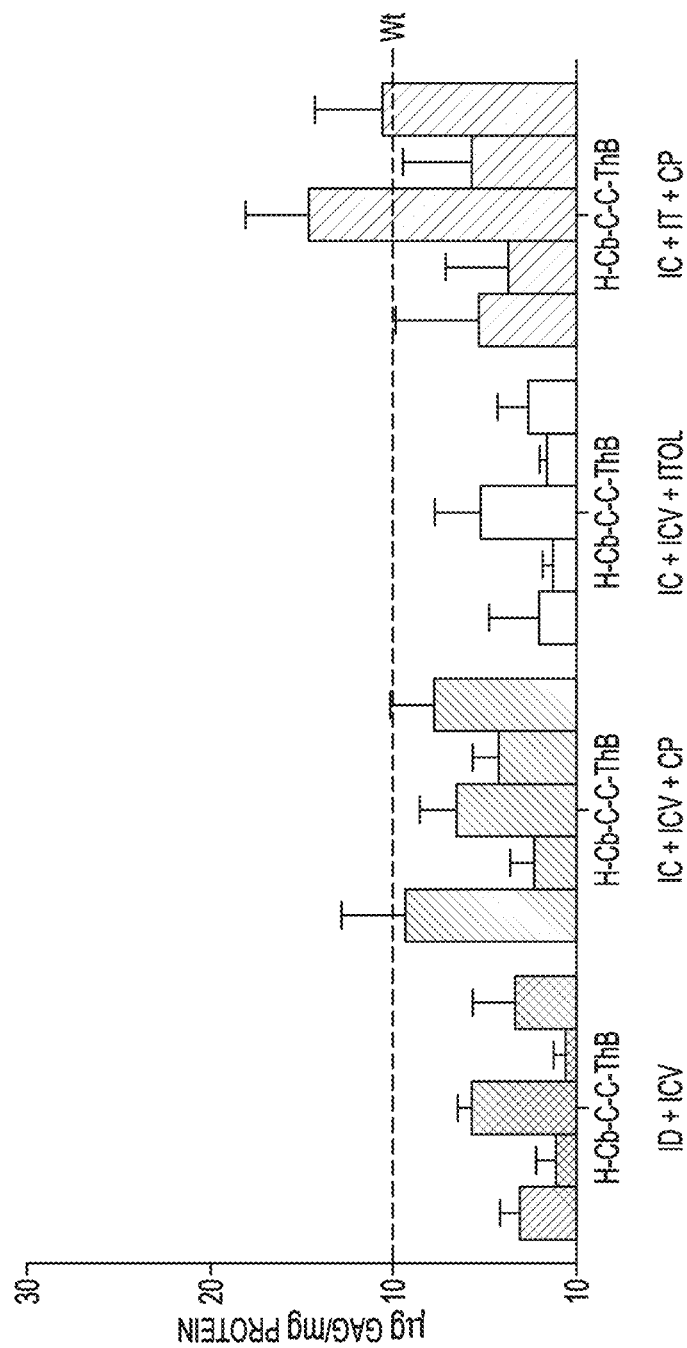
FIG. 16. Normalization of glycosaminoglycan (GAG) levels following intracranial or intrathecal AAV9 infusion. AAV0IDUA was injected intracranially or intrathecally into immunodeficient, immunosuppressed or immunotolerized MPS I mice as indicated. Animals were sacrificed 8-11 weeks after injection, then the brains were microdissected and analyzed for GAG levels. GAG storage was restored to wild type levels or close to wild type in all groups analyzed. H=hippocampus, Cb=cerebellum, C=cortex, S=striatum, ThB=thalamus and brain stem.
Figure 17B:
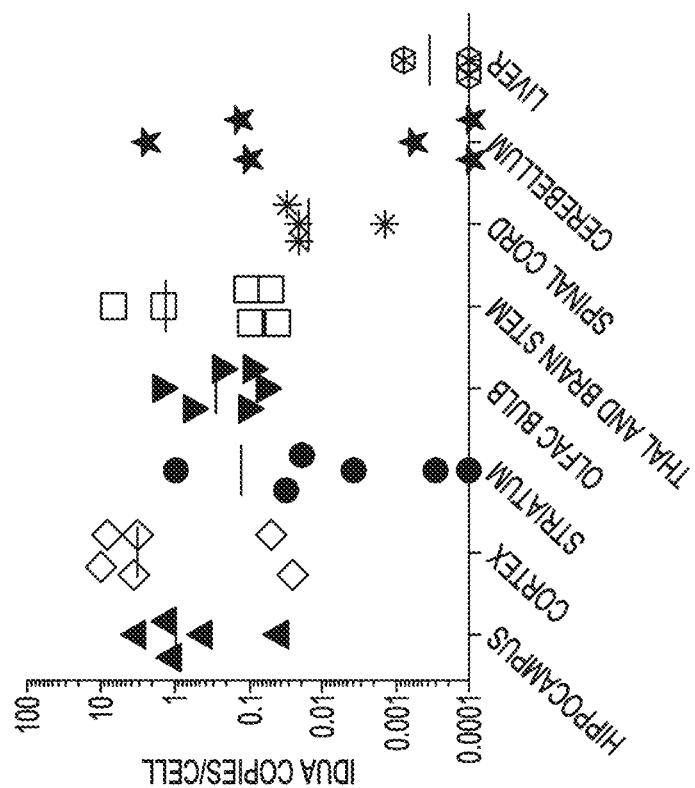
FIGS. 17A-B. IDUA vector copies in brain. Microdissected brains were analyzed for IDUA vector sequences by QPCR. The copy numbers in intracranially (A) and intrathecally (B) injected mice correlate to the levels of enzyme activity depicted in FIGS. 11 and 13.
Figure 17A:
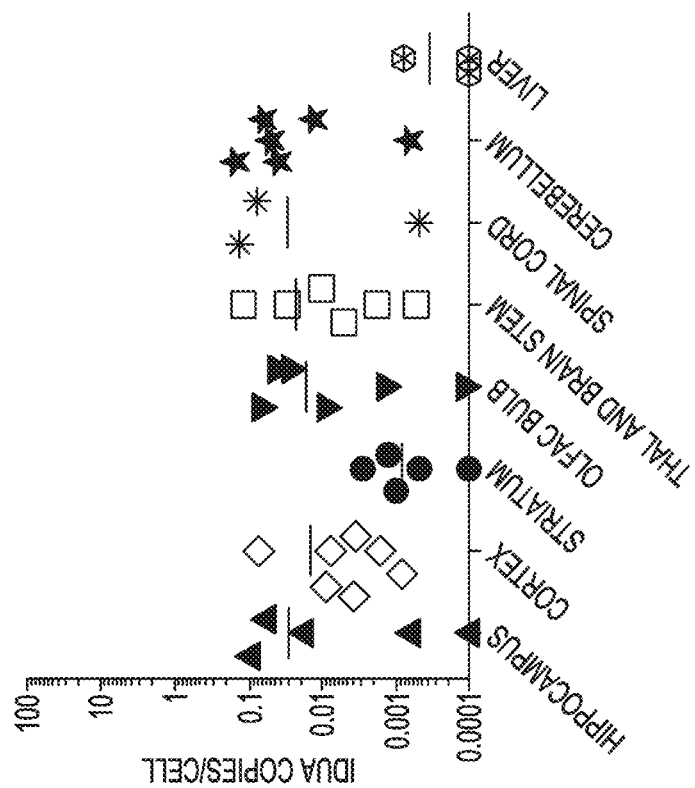

The presence of AAV9IDUA vector in animals that were immunotolerized and injected with vector either intracranially or intrathecally was evaluated by QPCR, as illustrated in FIG. 16. IDUA copies per cell were higher in animals infused intracranially in comparison with animals infused intrathecally, which is consistent with the higher level of enzyme activity seen in animals injected intracranially.

CONCLUSIONS

High, widespread, and therapeutic levels of IDUA were observed in all areas of the brain after intracerebroventricular and intrathecal routes of AAV9IDUA administration in adult mice Enzyme activities were restored to wild type levels or slightly higher in immunocompetent IDUA deficient animals infused with AAV-IDUA intrathecally. Significantly higher levels of IDUA enzyme were observed for both routes of vector injection in animals immunotolerized starting at birth by administration of IDUA protein.

Example III

Adult immunocompetent IDUA deficient mice (12 weeks old) were anesthetized with ketamine/xylazine, followed by intranasal infusion of AAV9IDUA vector. Vector was administered by applying eight 3 µL drops with a micropipette to the intranasal cavity, alternating between nostrils, at 2 minute intervals between each application. A total of $2.4-7\times10^{11}$ vector genomes was administered to each adult animal, depending on source of vector. Animals were immunosuppressed with 120 mg/kg cyclophosphamide administered weekly, starting the day after vector administration. Mice were sacrificed at 12 weeks post vector infusion, animals were assayed for IDUA enzyme expression and vector copies in the brain.

REFERENCES

Al-Ghananeem et al., *AAPS Pharm. Sci. Tech.*, 3:E5 (2002).
Bagger et al., *Eur. J. Pharm. Sci.*, 21:235-242 (2004b).
Bagger et al., *Int. J. Pharm.*, 269:311-322 (2004a).
Baker et al., *Exp. Brain Res.*, 63:461 (1986).
Balin et al., *J. Comp. Neurol.*, 251:260-280 (1986).
Banks et al., *J. Drug Target*, 17:91-97 (2009).
Banks et al., *J. Pharmacol. Exp. Ther.*, 309:469 (2004).
Banks, *Biopolymers*, 90:589 (2008).
Barakat et al., *J. Pharm. Pharmacol.*, 58:63 (2006).
Barbier et al., *Mol. Genet. Metab.*, 110:303 (2013).
Baumgartner et al., *Neuron.*, 58:639 (2008).
Benedict et al., *Neuroendocrinology*, 86:136 (2007b).
Benedict et al., *Neuropsychopharmacology*, 32:239 (2007a).
Benedict et al., *Psychoneuroendocrinology*, 29:1326 (2004).
Bjoraker et al., *J. Dev. Behav. Ped.*, 27:290 (2006).
Blits et al., *J. Neuros. Methods*, 185:257 (2010).
Born et al., *Nat. Neurosci.*, 5:514 (2002).
Boulton et al., *Am. J. Physiol.*, 276:R818 (1999).
Boulton et al., *Neuropathol. Appl. Neurobiol.*, 22:325 (1996).
Bradbury et al., *Am. J. Physiol.*, 240:F329 (1981).
Bradbury et al., *J. Physiol.*, 339:519 (1983).
Brady, *Ann. Rev. Med.*, 57:283 (2006).
Broadwell et al., *J. Comp. Neurol.*, 242:632 (1985).
Broekman et al., *Neuroscience*, 138:501 (2006).
Buck, In: Kandel E R, Schwartz J H, Jessell T M, editors. Principles of neural science. 4th edition. New York: McGraw-Hill Companies. pp. 625-652 (2000).
Buxer et al., *J. Neurochem.*, 56:1012 (1991).
Cai et al., *Sichuan Da Xue Xue Bao Yi Xue Ban*, 39:438 (2008).
Capsoni et al., *Proc. Natl. Acad. Sci. USA*, 99:12432 (2002).
Carare et al., *Neuropathol. Appl. Neurobiol.*, 34:131 (2008).
Cauna, In: Proctor D F, Andersen I, editors. Amsterdam: Elsevier Biomedical Press. pp. 45-69 (1982).
Charlton et al., *Int. J. Pharm.*, 338:94 (2007b).
Charlton et al., *J. Drug Target*, 15:370 (2007a).
Charlton et al., *Pharm. Res.*, 25:1531 (2008).
Chen et al., *J. Alzheimers Dis.*, 1:35 (1998).
Chen et al., *J. Pharm. Sci.*, 95:1364 (2006).
Chow et al., *J. Pharm. Sci.*, 88:754 (1999).
Chow et al., *J. Pharm. Sci.*, 90:1729 (2001).
Clerico et al., In: Doty R L, editor. Handbook of olfaction and gustation. 2nd edition. New York: Marcel Dekker, Inc. pp. 1-16 (2003).
Costantino et al., *Int. J. Pharm.*, 337:1 (2007).
Cserr et al., *Am. J. Physiol.*, 240:F319 (1981).
Cserr et al., *Brain Pathol.*, 2:269 (1992).
Dahlin et al., *Eur. J. Pharm. Sci.*, 14:75 (2001).
Danhof et al., American Association of Pharmaceutical Scientists Annual Meeting, Atlanta, GA (2008).
Danielyan et al., *Eur. J. Cell. Biol.*, 88:315 (2009).
Davis et al., *Clin. Pharmacokinet.*, 42:1107 (2003).
de Lorenzo, In: Wolstenholme G E W, Knight J, editors. Taste and smell in vertebrates. London: Churchill. pp. 151-175 (1970).
De Rosa et al., *Proc. Natl. Acad. Sci. USA*, 102:3811 (2005).
DeSesso, *Qual. Assur.*, 2:213 (1993).
deSouza et al., *Eur. Neuropsychopharmacol.*, 19:53 (2009).
Dhanda et al., *Drug Del. Tech.*, 5:64 (2005).
Dhuria et al., *J. Pharm. Sci.*, 98:2501 (2009b).
Dhuria et al., *J. Pharmaceutical Sciences*, 99:1654 (2010).
Dhuria et al., *J. Pharmacol. Exp. Ther.*, 328:312 (2009a).
Diano et al., *J. Clin. Invest.*, 118:26 (2008).
Dickson et al., *Mol. Gen. Metab.*, 91:61 (2007).
Djupesland et al., *Laryngoscope*, 116:466 (2006).
Domes et al., *Biol. Psychiatry*, 61:731 (2007b).
Domes et al., *Biol. Psychiatry*, 62:1187 (2007a).
Dufes et al., *Int. J. Pharm.*, 255:87 (2003).
Einer-Jensen et al., *Exp. Brain Res.*, 130:216 (2000b).
Einer-Jensen et al., *Pharmacol. Toxicol.*, 87:276 (2000a).
Einer-Jensen et al., *Reproduction*, 129:9 (2005).
Ellinwood et al., *Mol. Genet. Metab.*, 91:239 (2007).
Fehm et al., *J. Clin. Endocrinol. Metab.*, 86:1144 (2001).
Field et al., *J. Neurocytol.*, 32:317 (2003).
Fliedner et al., *Endocrinology*, 17:2088 (2006).
Foust et al., *Nat. Biotech.*, 27:5 (2009)).
Francis et al., *Brain*, 131:3311 (2008).
Fratantoni et al., *Science*, 162:570 (1968).
Frey et al., *Drug Delivery*, 4:87 (1997).
Frey I I, *Drug Del. Tech.*, 2:46 (2002).
Fuss et al., *Eur. J. Neurosci.*, 22:2649 (2005).
Gao et al., *Biomaterials*, 27:3482 (2006).
Gao et al., *Int. J. Pharm.*, 340:207 (2007a).
Gao et al., *J. Control Release*, 121:156 (2007b).
Gopinath et al., *Current Ther. Res.*, 23:596 (1978).
Gozes et al., *Curr. Alzheimer Res.*, 4:507 (2007).
Graff et al., *Pharm. Res.*, 20:1225 (2003).
Graff et al., *Pharm. Res.*, 22:235 (2005a).
Graff et al., *Pharm. Res.*, 22:86 (2005b).
Gray, 15th revised edition (Classic Collectors edition). New York: Bounty Books (1978).
Grevers et al., *Arch. Otorhinolaryngol.*, 244:55 (1987).
Groothuis et al., *J. Cereb. Blood Flow Metab.*, 27:43 (2007).
Gross et al., *J. Anat.*, 135:83 (1982).
Guastella et al., *Biol. Psychiatry*, 63:3 (2008).
Hadaczek et al., *Mol. Ther.*, 14:69 (2006).
Hallschmid et al., *Regul. Pept.*, 149:79 (2008).
Han et al., *J. Mol. Med.*, 85:75 (2007).
Hanson et al., *BMC Neurosci.*, 9:S5 (2008).
Hanson et al., *Drug Del. Tech.*, 4:66 (2004).
Hanson et al., San Diego, CA: Society for Neuroscience (2007).
Hanson et al., In: EPO, editor. Biopharm and HealthPartners Research Foundation (2008).
Hartung et al., *J. Am. Soc. Gene Ther.*, 9:866 (2004).
Hartung et al., *Mol. Thera.*, 9:869 (2004).
Hashizume et al., *Neuro. Oncol.*, 10:112 (2008).
Hatterer et al., *Blood*, 107:806 (2006).
Herati et al., *J. Gene Med.*, 10:972 (2008).
Hess et al., *Exp. Neuro.*, 186:134 (2004).
Horvat et al., *Eur. J. Pharm. Biopharm.*, 72:252 (2009).
Hussar et al., *Chem. Senses*, 27:7 (2002).
Ilium, *J. Control Release*, 87:187 (2003).
Ilium, *J. Pharm. Pharmacol.*, 56:3 (2004).
Itaya et al., *Brain Res.*, 398:397 (1986).
Jansson et al., *J. Drug Target*, 10:379 (2002).
Jogani et al., *Alzheimer Dis. Assoc. Disord.*, 22:116 (2008).
Johnston et al., *Cerebrospinal Fluid Res.*, 1:2 (2004).
Kakkis et al., *Mol. Gen. Met.*, 83:163 (2004).
Kandimalla et al., *J. Pharm. Sci.*, 94:613 (2005b).
Kandimalla et al., *Pharm. Res.*, 22:1121 (2005a).
Kida et al., *Neuropathol. Appl. Neurobiol.*, 19:480 (1993).
Kirsch et al., *J. Neurosci.*, 25:11489 (2005).
Klein et al., *J. Am. Soc. Gene Ther.*, 13:517 (2006).
Koos et al., *Neuroreport*, 16:1929 (2005).
Kosfeld et al., *Nature*, 435:673 (2005).
Kristensson et al., *Acta Neuropathol* (Bed), 19:145 (1971).

Krivit, *Springer Seminars in Immunopathology*, 26:119 (2004).
Kumar et al., *Curr. Sci.*, 43:435 (1974).
Kumar et al., *Int. J. Pharm.*, 358:285 (2008).
Li et al., *Chin. J. Physiol.*, 48:7 (2005c).
Li et al., *Glia*, 52:245 (2005a).
Li et al., *J. Neurocytol.*, 34:343 (2005b).
Loftus et al., *Neuroscience*, 139:1061 (2006).
Luzzati et al., *J. Mol. Biol.*, 343:199 (2004).
Mackay-Sim, In: Doty R L, editor. Handbook of olfaction and gustation. 2nd edition. New York: Marcel Dekker, Inc. pp. 93-113 (2003).
Martinez et al., *Neuroscience*, 157:908 (2008).
Minn et al., *J. Drug Target*, 10:285 (2002).
Miragall et al., *J. Comp. Neurol.*, 341:433 (1994).
Muenzer, *J. Pediatrics*, 144:S27 (2004).
Munoz-Rojas et al., *Am. J. Med. Gen.*, 146A:2538 (2008).
Neufeld and Muenzer, In A. L. B. C. R. Scriver, W. S. Sly, et al (ed.), McGraw Hill, NY, pg. 3421 (2001).
Nonaka et al., *J. Pharmacol. Exp. Ther.*, 325:513 (2008).
Ohlfest et al., *Blood*, 105:2691 (2005).
Orchard et al., *J. Pediatrics*, 151:340 (2007).
Owens et al., *Diabet. Med.*, 20:886 (2003).
Pan et al., *Brain Res.*, 1188:241 (2008).
Pardridge, *NeuroRx*, 2:3 (2005).
Parker et al., *Psychoneuroendocrinology*, 30:924 (2005).
Pastores, *Exp. Opin. Biol. Ther.*, 8:1003 (2008).
Perl et al., *Lancet*, 1:1028 (1987).
Peters et al., *Bone Marrow Transpl.*, 31:229 (2003).
Pollock et al., *J. Anat.*, 191:337 (1997).
Raghavan et al., *J. Laryngol. Otol.*, 114:456 (2000).
Reger et al., *J. Alzheimers Dis.*, 13:323 (2008a).
Reger et al., *Neurobiol. Aging*, 27:451 (2006).
Reger et al., *Neurology*, 70:440 (2008b).
Rennels et al., *Adv. Neurol.*, 52:431 (1990).
Rennels et al., *Brain Res.*, 326:47 (1985).
Reolon et al., *Brain Res.*, 1076:225 (2006).
Rimmele et al., *J. Neurosci.*, 29:38 (2009).
Ross et al., *J. Neuroimmunol.*, 151:66 (2004).
Ross et al., *Neurosci. Lett.*, 439: 30 (2008).
Sakane et al., *J. Pharm. Pharmacol.*, 46:378 (1994).
Sakane et al., *J. Pharm. Pharmacol.*, 47:379 (1995).
Sarkar, *Pharm. Res.*, 9:1 (1992).
Schaefer et al., *J. Comp. Neurol.*, 444:221 (2002).
Scheibe et al., *Arch. Otolaryngol. Head Neck Surg.*, 134:643 (2008).
Schley et al., *J. Theor. Biol.*, 238:962 (2006).
Schulz et al., *Endocrinology*, 145:2696 (2004).
Scott et al., *Am. J. Hum. Genet.*, 53:973 (1993).
Shimizu et al., *Int. J. Obes.* (*Lond*), 29:858 (2005).
Shipley, *Brain Res. Bull.*, 15:129 (1985).
Skipor et al., *Reprod. Biol.*, 3:143 (2003).
Steen et al., *J. Alzheimers Dis.*, 7:63 (2005).
Stefanczyk-Krzymowska et al., *Exp. Physiol.*, 85:801 (2000).
Takano et al., *J. Histochem. Cytochem.*, 53:611 (2005).
Thorne et al., *Brain Res.*, 692:278 (1995).
Thorne et al., *Clin. Pharmacokinet.*, 40:907 (2001).
Thorne et al., *Neuroscience*, 127:481 (2004).
Thorne et al., *Neuroscience*, 152:785 (2008).
Thorne, R G. 2002. The nasal pathways for drug delivery to the central nervous system: Studies with protein tracers and therapeutics. Doctoral Dissertation, University of Minnesota.
Unger et al., *J. Neuropath. Exp. Neuro.*, 52:460 (1993).
van den Berg et al., *Eur. J. Pharm. Biopharm.*, 58:131 (2004b).
Van den Berg et al., *J. Drug Target*, 11:325 (2003).
van den Berg et al., *J. Neurosci. Methods*, 116:99 (2002).
van den Berg et al., *Pharm. Res.*, 21:799 (2004a).
Van Diest et al., *J. Anat.*, 128:293 (1979).
Vyas et al., *AAPS PharmSciTech.*, 7:E1 (2006c).
Vyas et al., *Crit. Rev. Ther. Drug Carrier Syst.*, 23:319 (2006b).
Vyas et al., *J. Drug Target*, 13:317 (2005).
Vyas et al., *J. Pharm. Sci.*, 95:570 (2006a).
Walter et al., *Arch. Histol. Cytol.*, 69:37 (2006a).
Walter et al., *Neuropathol. Appl. Neurobiol.*, 32:388 (2006b).
Wang et al., *Cancer Chemother. Pharmacol.*, 57:97 (2006a).
Wang et al., *Eur. J. Pharm. Biopharm.*, 70:735 (2008).
Wang et al., *Int. J. Pharm.*, 317:40 (2006b).
Wang et al., *Int. J. Pharm.*, 341:20 (2007).
Watson et al., *Gene Therapy*, 16 Feb. 2006, doi:10.1038/sj.gt.3302735.
Weller et al., *Neurol. Res.*, 25:611 (2003).
Westin et al., *Eur. J. Pharm. Sci.*, 24:565 (2005).
Westin et al., *Pharm. Res.*, 23:565 (2006).
Williams et al., *J. Comp. Neurol.*, 470:50 (2004).
Wioland et al., *J. Histochem. Cytochem.*, 48:1215 (2000).
Wolf et al., *Neurobio. Dis.*, 43:123 (2011).
Xu et al., *J. Clin. Invest.*, 118:272 (2008).
Yamada et al., *Am. J. Physiol.*, 261:H1197 (1991).
Yang et al., *J. Pharm. Sci.*, 94:1577 (2005).
Zhang et al., *Acta Neuropathol.* (*Berl*), 83:233 (1992).
Zhang et al., *Acta Pharmacol. Sin.*, 25:522 (2004a).
Zhang et al., *Int. J. Pharm.*, 275:85 (2004b).
Zhang et al., *J. Drug Target*, 14:281 (2006).
Zhao et al., *Acta Pharmacol. Sin.*, 28:273 (2007).
Zhao et al., *Chin. Med. Sci. J.*, 19:257 (2004).
Zheng et al., *Mol. Genet. Metab.*, 79:233 (2003).
Ziegler and Shapiro, In J. Donders and S. Hunter (ed.), Cambridge University Press, p. 427 (2007).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to treat one or more symptoms of mucopolysaccharidosis type II (MPSII) in a human having MPSII, consisting of: administering to a cisterna *magna* of the human a composition comprising an amount of a recombinant adeno-associated virus (rAAV) 9 or rAAVrh10 vector comprising an open reading frame encoding iduronate-2-sulfatase in a physiologically compatible buffer effective to treat the one or more symptoms of MPSII.

2. The method of claim 1 wherein the human is an immunocompetent adult.

3. The method of claim 1 wherein one symptom is neurodegeneration.

4. The method of claim 1 wherein the human is immunotolerized to iduronate-2-sulfatase.

5. The method of claim 1 wherein the amount administered reduces glycosaminoglycans (GAG).

6. The method of claim 1 wherein rAAV9 is administered.

7. The method of claim 1 wherein rAAVrh10 is administered.

8. A method to treat one or more neurological symptoms of mucopolysaccharidosis type II (MPSII) in a human having MPSII, consisting of: administering to a cisterna *magna* of the human a composition comprising an amount of a recombinant adeno-associated virus (rAAV) 9 vector comprising an open reading frame encoding iduronate-2-sulfatase effective to treat the one or more symptoms of MPSII.

9. The method of claim 8 wherein one symptom is neurodegeneration.

10. The method of claim 8 wherein the human has been administered an immune suppressant.

11. The method of claim 10 wherein the immune suppressant comprises cyclophosphamide.

12. The method of claim 10 wherein the immune suppressant comprises a glucocorticoid, cytostatic agents including an alkylating agent, an anti-metabolite, a cytotoxic antibiotic, an antibody, or an agent active on immunophilin.

13. The method of claim 10 wherein the immune suppressant comprises a nitrogen mustard, nitrosourea, platinum compound, methotrexate, azathioprine, mercaptopurine, fluorouracil, dactinomycin, an anthracycline, mitomycin C, bleomycin, mithramycin, IL-2 receptor- (CD25-) or CD3-directed antibodies, anti-IL-2 antibodies, ciclosporin, tacrolimus, sirolimus, IFN-β, IFN-γ, an opioid, or TNF-α (tumor necrosis factor-alpha) binding agent.

14. The method of claim 10 wherein the immune suppressant is administered before the rAAV9 vector.

15. The method of claim 10 wherein the immune suppressant is systemically administered.

16. The method of claim 10 wherein one symptom is increased GAG and the amount administered reduces GAG.

17. A method to treat one or more symptoms of mucopolysaccharidosis type II (MPSII) in a human having MPSII, consisting of: administering to a cisterna *magna* of the human a composition comprising an amount of a recombinant adeno-associated virus (rAAV) 9 or rAAVrh10 vector comprising an open reading frame encoding iduronate-2-sulfatase effective to inhibit or treat the one or more symptoms of MPSII and administering an effective amount of an immune suppressant.

18. The method of claim 17 wherein the rAAV vector and the immune suppressant are co-administered.

19. The method of claim 17 wherein the immune suppressant is administered after the rAAV vector.

20. The method of claim 8 wherein at least one neurological symptom is treated.

21. A method to treat one or more symptoms associated with a deficiency in iduronate-2-sulfatase in a human, consisting of: providing a human with a deficiency in iduronate-2-sulfatase that is immunotolerized to iduronate-2-sulfatase; and administering to a cisterna *magna* of the human a composition comprising an amount of a rAAV9 or rAAVrh10 vector comprising an open reading frame encoding iduronate-2-sulfatase effective to treat the one or more symptoms associated with the deficiency in iduronate-2-sulfatase.

22. The method of claim 21 wherein multiple doses of the composition comprising the rAAV9 or rAAVrh10 vector are administered.

23. The method of claim 21 wherein rAAV9 is administered.

24. The method of claim 21 wherein rAAVrh10 is administered.

25. The method of claim 21 wherein one of the symptoms is increased glycosaminoglycans (GAG) and the amount administered reduces GAG.

* * * * *

UNITED STATES PATENT AND TRADEMARK OFFICE
CERTIFICATE OF CORRECTION

PATENT NO. : 12,121,567 B2
APPLICATION NO. : 15/717358
DATED : October 22, 2024
INVENTOR(S) : McIvor et al.

Page 1 of 3

It is certified that error appears in the above-identified patent and that said Letters Patent is hereby corrected as shown below:

On the Title Page

On page 3, in Column 2, under Item (56) "Other Publications", Line 68, delete "toRules" and insert --to Rules-- therefor On page 6, in Column 1, under Item (56) "Other Publications", Line 66, delete "Seria" and insert --Serial-- therefor On page 6, in Column 1, under Item (56) "Other Publications", Line 67, delete "maild" and insert --mailed-- therefor On page 8, in Column 2, under Item (56) "Other Publications", Line 55, delete "replacemnet" and insert --replacement-- therefor On page 10, in Column 2, under Item (56) "Other Publications", Line 40, delete "Treatmnet" and insert --Treatment-- therefor On page 10, in Column 2, under Item (56) "Other Publications", Line 41, delete "Anaylsis" and insert --Analysis-- therefor On page 11, in Column 1, under Item (56) "Other Publications", Line 4, delete "Reeamination" and insert --Reexamination-- therefor On page 11, in Column 2, under Item (56) "Other Publications", Line 21, delete "transplation" and insert --transplantation-- therefor On page 12, in Column 2, under Item (56) "Other Publications", Line 26, delete "malled" and insert --mailed-- therefor Signed and Sealed this
Fourteenth Day of January, 2025

Derrick Brent
*Acting Director of the United States Patent and Trademark Office*

In the Specification

In Column 4, Line 4, delete "MV" and insert --AAV-- therefor

In Column 4, Line 25, delete "MV" and insert --AAV-- therefor

In Column 4, Line 35, delete "MV" and insert --AAV-- therefor

In Column 4, Line 55, delete "MV-2," and insert --AAV-2,-- therefor

In Column 4, Line 56, delete "MV" and insert --AAV-- therefor

In Column 6, Line 3, delete "MV" and insert --AAV-- therefor

In Column 6, Line 11, delete "MV" and insert --AAV-- therefor

In Column 7, Line 34, delete "MV" and insert --AAV-- therefor

In Column 9, Line 24, after "area)", insert --.--

In Column 9, Line 46, delete "hippocampus." and insert --hippocampus,-- therefor In Column 9, Line 46, delete "cortex." and insert --cortex,-- therefor In Column 9, Line 50, delete "mice." and insert --mice,-- therefor In Column 9, Line 53, delete "mice." and insert --mice,-- therefor In Column 9, Line 56, delete "deficient" and insert --deficient)-- therefor In Column 10, Line 27, delete "AAVOIDUA" and insert --AAV9IDUA-- therefor In Column 10, Line 46, delete "AAVOIDUA" and insert --AAV9IDUA-- therefor In Column 12, Line 17, delete "MV" and insert --AAV-- therefor In Column 12, Line 28, delete "MV-2," and insert --AAV-2,-- therefor In Column 14, Line 33, delete "MV" and insert --AAV-- therefor In Column 16, Line 63, delete "C1-05" and insert --C1-C5-- therefor In Column 19, Line 9, delete "(CALF)," and insert --(GALP),-- therefor In Column 25, Line 7, delete "MPSI" and insert --MPS I-- therefor

CERTIFICATE OF CORRECTION (continued)
U.S. Pat. No. 12,121,567 B2

In Column 30, Line 53, delete "Ilium," and insert --Illum,-- therefor

In Column 30, Line 54, delete "Ilium," and insert --Illum,-- therefor

In Column 30, Line 67, delete "(Bed)," and insert --(Berl),-- therefor